US011000384B2

(12) United States Patent
Al-Jazaeri et al.

(10) Patent No.: US 11,000,384 B2
(45) Date of Patent: May 11, 2021

(54) DISTALLY EXPANDING FACET JOINT IMPLANT AND DELIVERY DEVICE

(71) Applicants: Ayman H. Al-Jazaeri, Riyadh (SA); Amro F. Al-Habib, Riyadh (SA); Sami AlEissa, Riyadh (SA)

(72) Inventors: Ayman H. Al-Jazaeri, Riyadh (SA); Amro F. Al-Habib, Riyadh (SA); Sami AlEissa, Riyadh (SA)

(*) Notice: Subject to any disclaimer, the term of this patent is extended or adjusted under 35 U.S.C. 154(b) by 12 days.

(21) Appl. No.: 16/653,010

(22) Filed: Oct. 15, 2019

(65) Prior Publication Data
US 2021/0106432 A1    Apr. 15, 2021

(51) Int. Cl.
| A61F 2/46 | (2006.01) |
| A61F 2/44 | (2006.01) |
| A61B 17/02 | (2006.01) |
| A61B 17/70 | (2006.01) |
| A61F 2/30 | (2006.01) |

(52) U.S. Cl.
CPC .......... *A61F 2/4405* (2013.01); *A61B 17/025* (2013.01); *A61B 17/7064* (2013.01); *A61F 2/4611* (2013.01); *A61B 2017/0256* (2013.01); *A61F 2002/30579* (2013.01)

(58) Field of Classification Search
CPC ........ A61F 2/44; A61F 2/4405; A61F 2/4455; A61F 2/446; A61F 2/4465; A61F 2/447; A61F 2/4611; A61B 17/025
See application file for complete search history.

(56) References Cited

U.S. PATENT DOCUMENTS

| 5,059,193 A | 10/1991 | Kuslich |
| 5,665,122 A | 9/1997 | Kambin |
| 7,753,958 B2 | 7/2010 | Gordon |
| 7,776,090 B2 | 8/2010 | Winslow |
| 8,029,540 B2 | 10/2011 | Winslow |
| 8,267,966 B2 | 9/2012 | McCormack |
| 8,361,152 B2 | 1/2013 | McCormack |
| 8,512,347 B2 | 8/2013 | McCormack |
| 8,753,345 B2 | 6/2014 | McCormack |
| 8,834,472 B2 | 9/2014 | McCormack |
| 8,845,728 B1 | 9/2014 | Samy Ahdou |
| 9,005,288 B2 | 4/2015 | McCormack |
| 9,011,492 B2 | 4/2015 | McCormack |
| 9,044,277 B2 | 6/2015 | O'Neil |
| 9,131,965 B2 | 9/2015 | Prewett |
| D745,156 S | 12/2015 | McCormack |

(Continued)

*Primary Examiner* — Si Ming Ku
(74) *Attorney, Agent, or Firm* — Neustel Law Offices

(57) ABSTRACT

A distally expanding facet joint implant and delivery device for distally distracting a facet joint. The facet joint implant generally includes an outer part and an inner part. The outer part includes a pair of opposed distally expandable facet plates connected by a hinge. The inner part includes a wedge that is selectively movable against the facet plates to distally expand and contract the facet joint implant into open and closed states. Teeth on the outer part engage indents on the inner part to maintain the facet joint implant in the distally expanded state. The outer and inner parts include outer and inner connectors, and the delivery device includes corresponding outer and inner connectors adapted to be in locked engagement with the outer and inner connectors to hold the implant and selectively cause it to distally expand and contract.

26 Claims, 33 Drawing Sheets

(56) References Cited

U.S. PATENT DOCUMENTS

| | | |
|---|---|---|
| 9,308,091 B2 | 4/2016 | Lang |
| 9,333,086 B2 | 5/2016 | McCormack |
| 9,381,049 B2 | 7/2016 | McCormack |
| 9,622,873 B2 | 4/2017 | McCormack |
| 9,629,665 B2 | 4/2017 | McCormack |
| 9,649,138 B2 | 5/2017 | Altarac |
| 10,122,239 B2 | 11/2018 | Kobayashi |
| 10,327,909 B2 | 6/2019 | Baynham |
| 2004/0215198 A1 | 10/2004 | Marnay |
| 2006/0167456 A1 | 7/2006 | Johnston |
| 2011/0035011 A1 | 2/2011 | Cain |
| 2012/0226357 A1 | 9/2012 | Varela |
| 2014/0194886 A1 | 7/2014 | Poulos |
| 2014/0257486 A1 | 9/2014 | Alheidt |
| 2014/0277460 A1 | 9/2014 | Schifano |
| 2015/0342648 A1 | 12/2015 | McCormack |
| 2015/0351923 A1 | 12/2015 | Emstad |
| 2016/0022438 A1 | 1/2016 | Lamborne |
| 2016/0338846 A1* | 11/2016 | Walker ................ A61F 2/4611 |
| 2016/0374740 A1 | 12/2016 | Donald |
| 2017/0056197 A1 | 3/2017 | Weiman |
| 2018/0116815 A1* | 5/2018 | Kuyler .................... A61F 2/28 |
| 2019/0021868 A1* | 1/2019 | Ludwig ................ A61F 2/442 |
| 2019/0133784 A1 | 5/2019 | Gunn |

\* cited by examiner

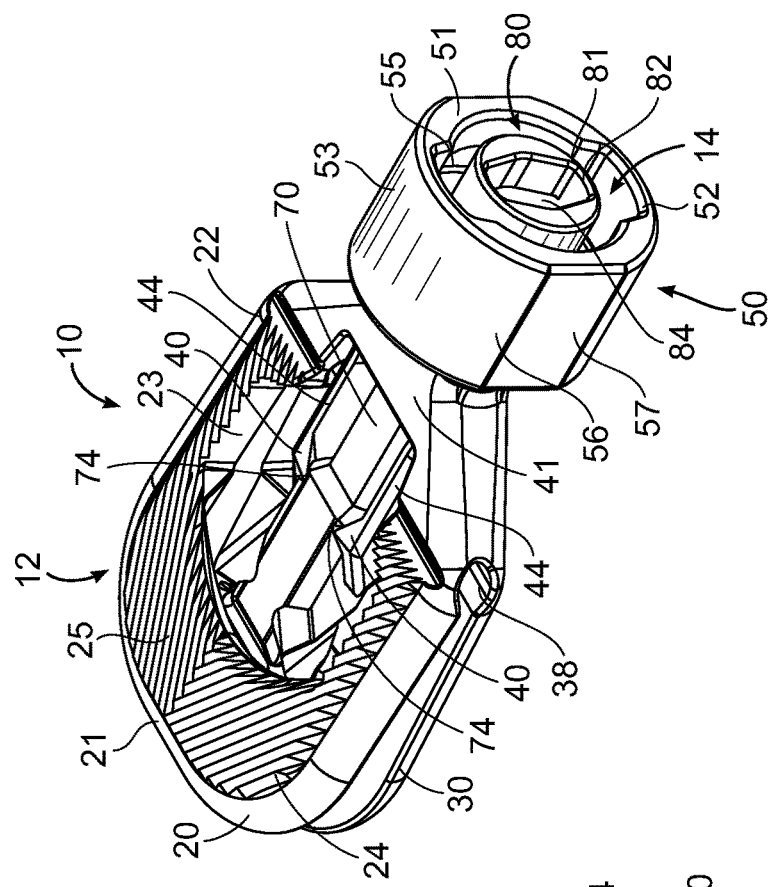
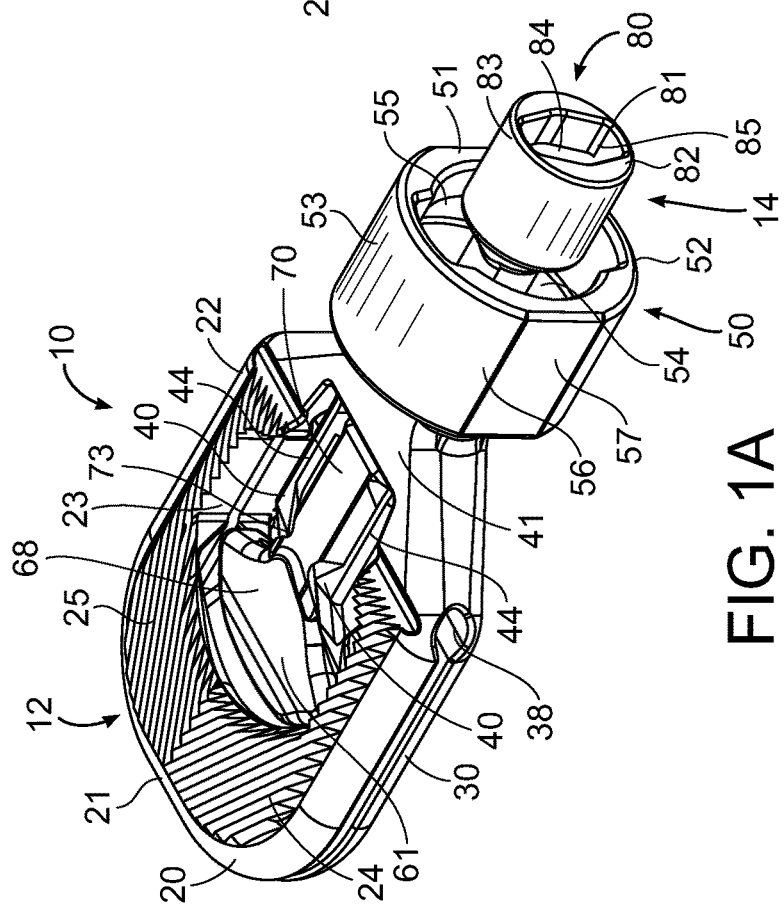
FIG. 1B
FIG. 1A

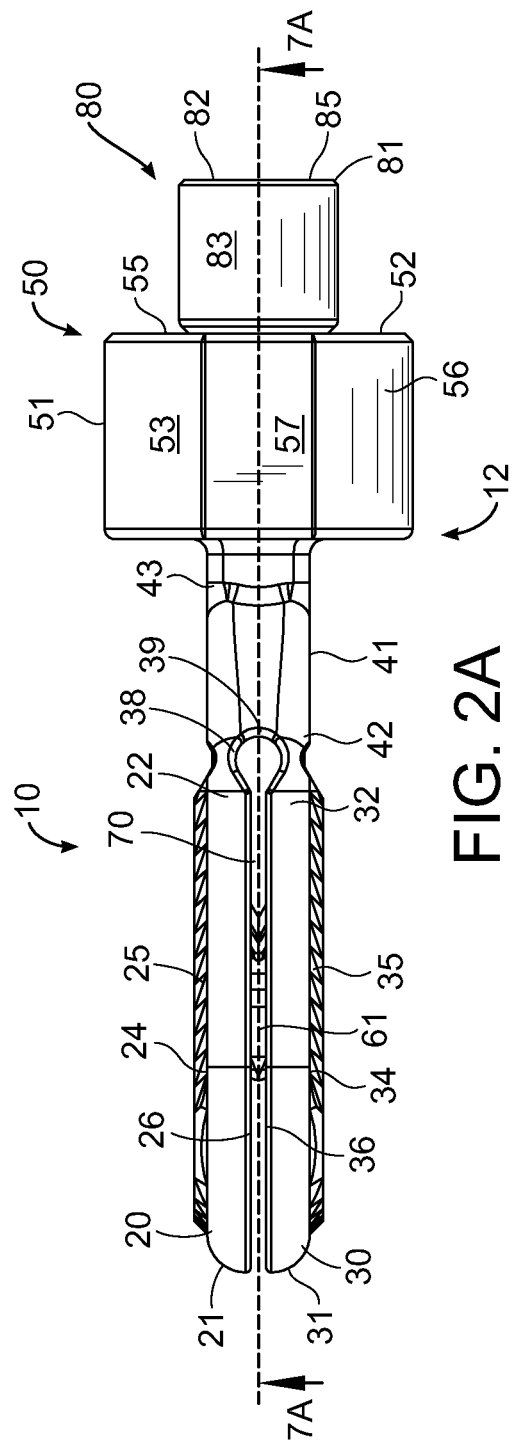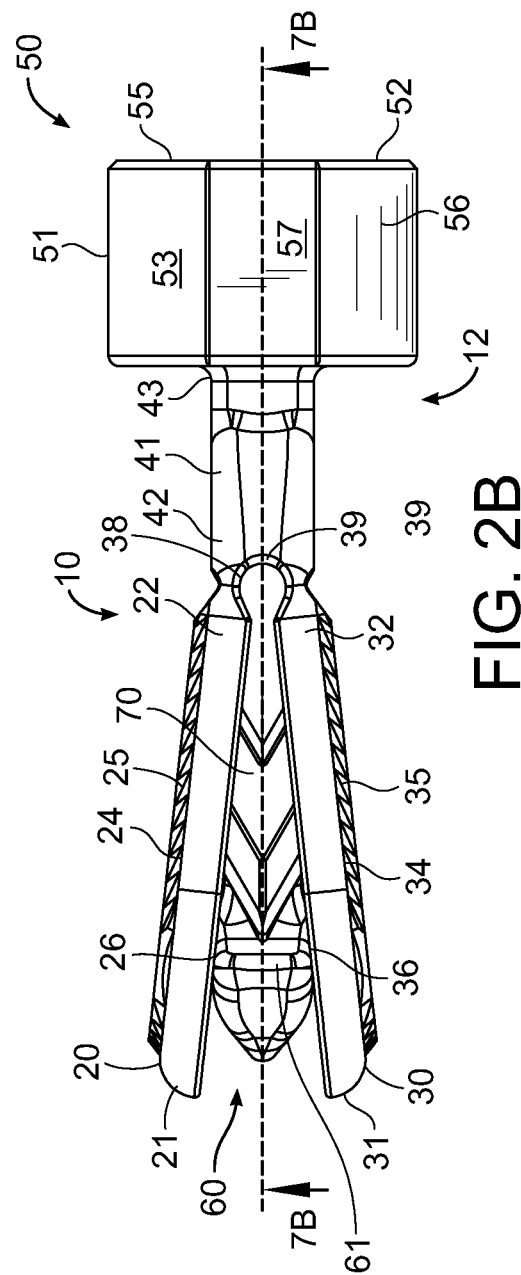

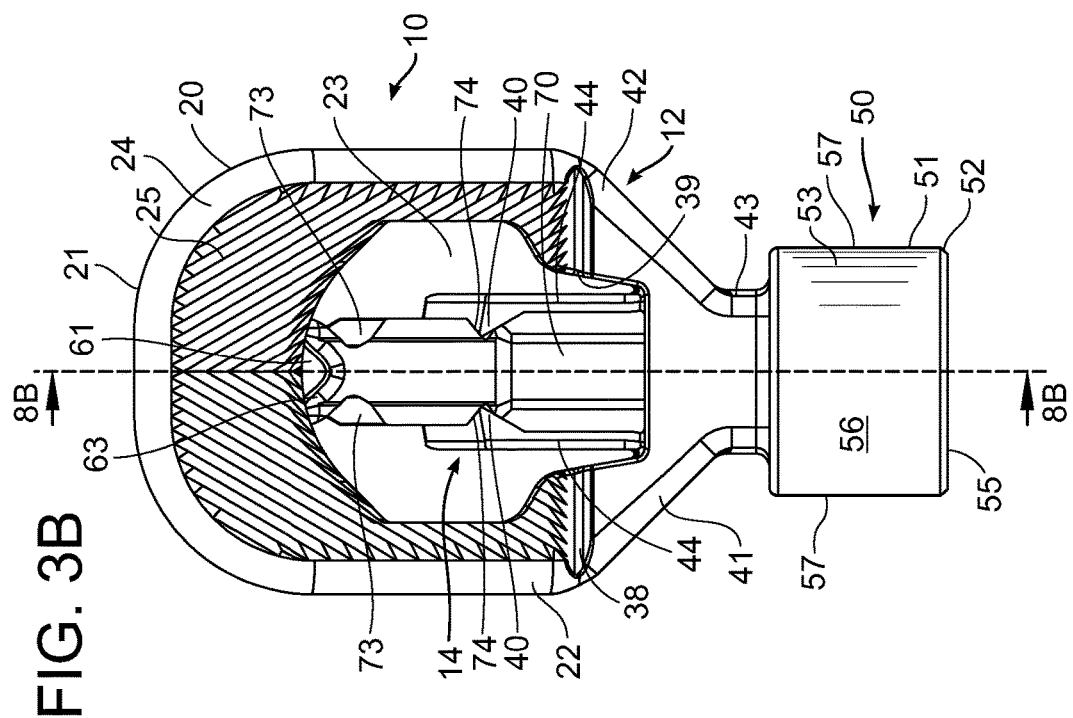
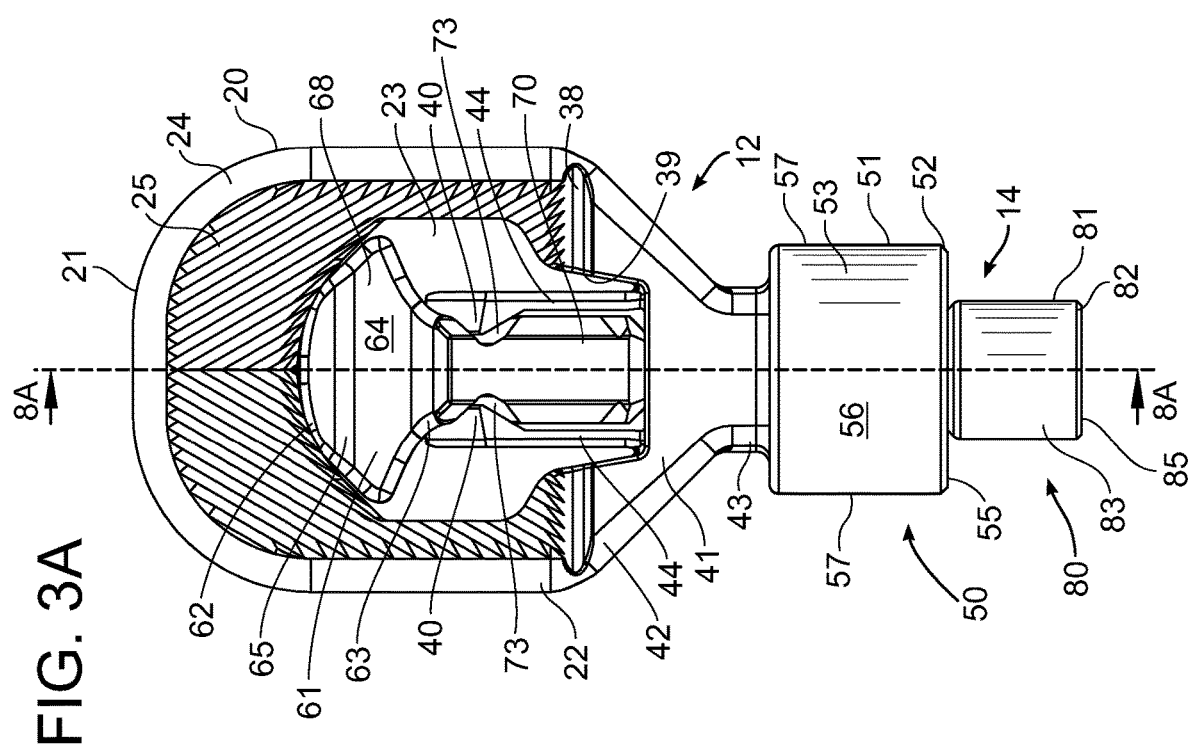

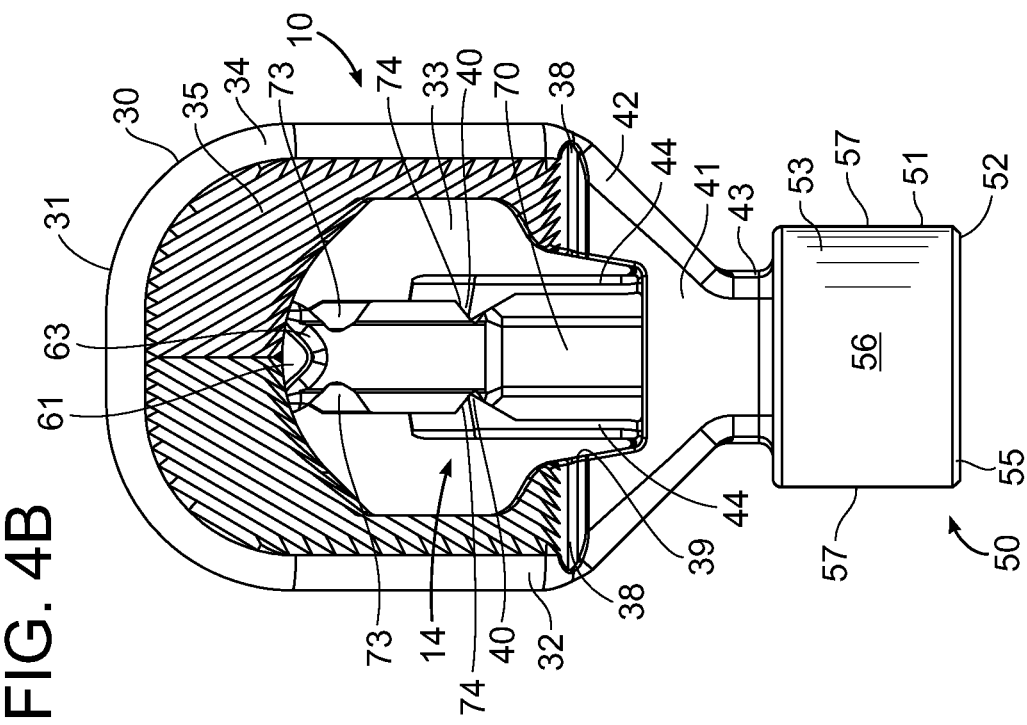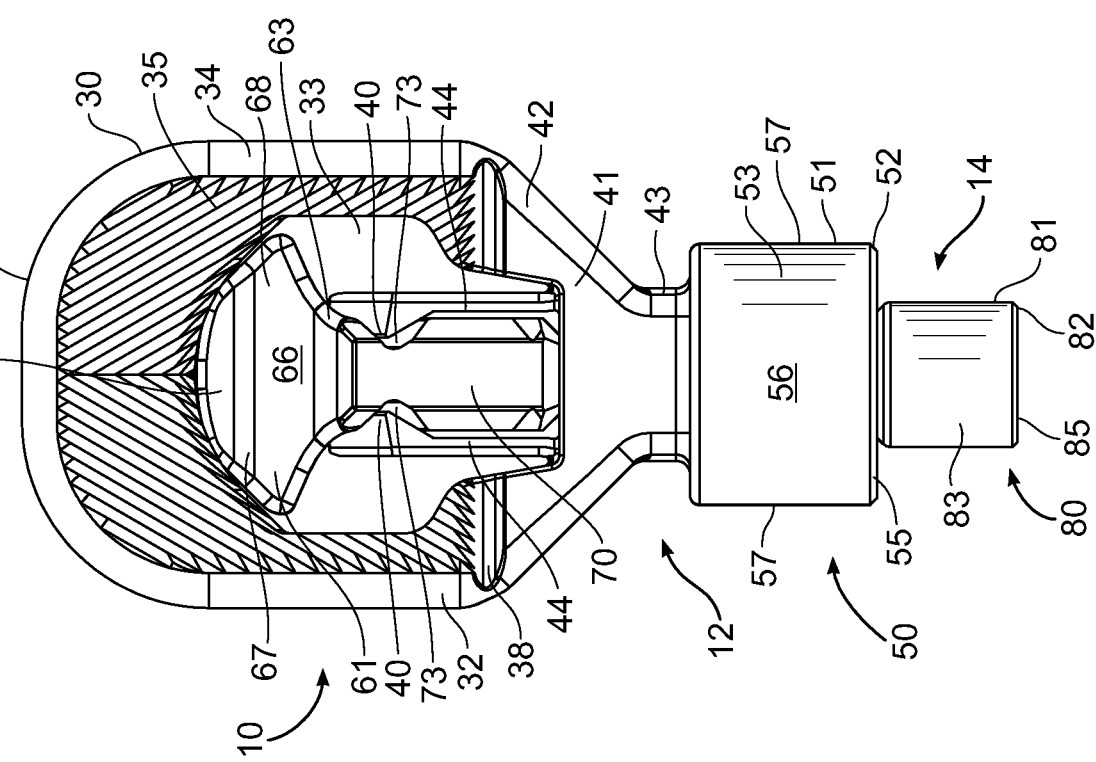

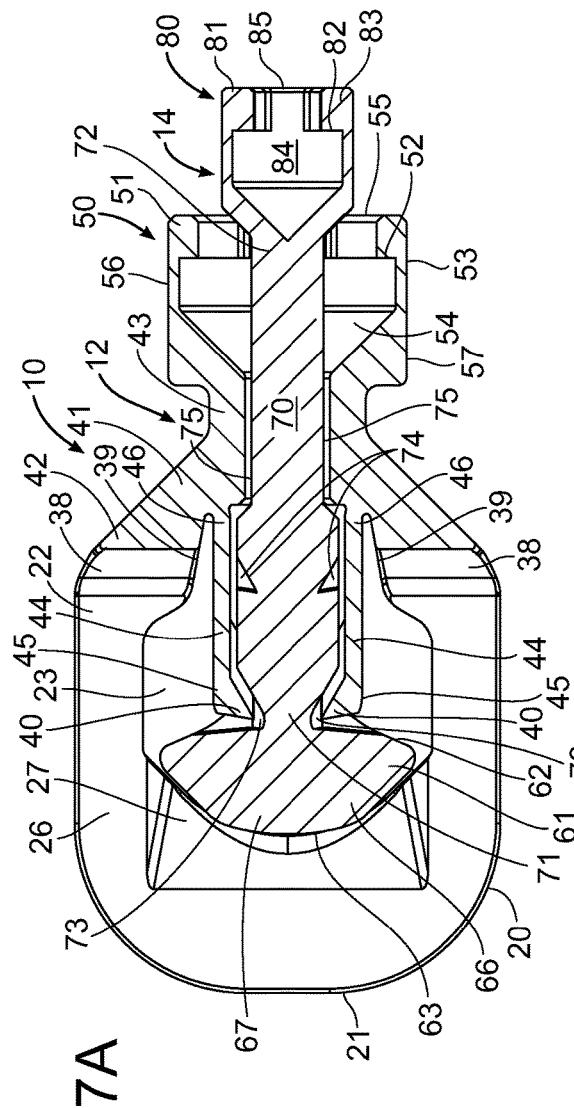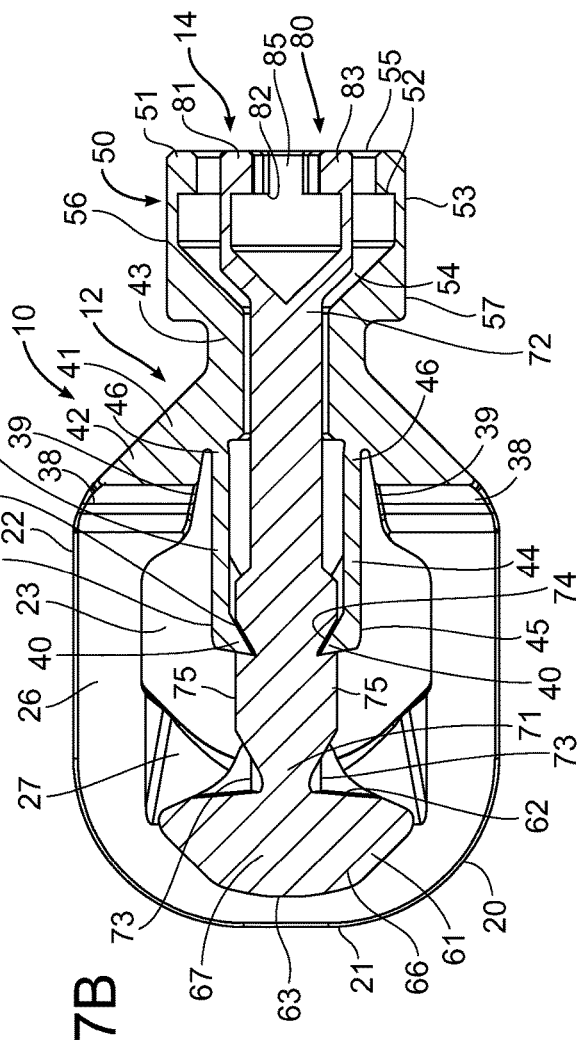

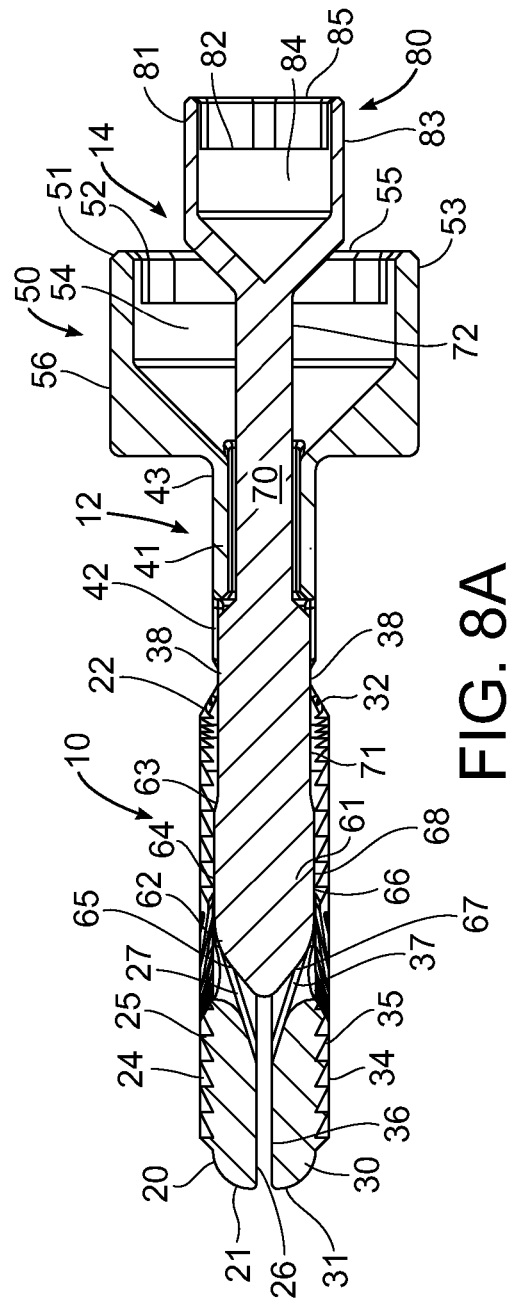
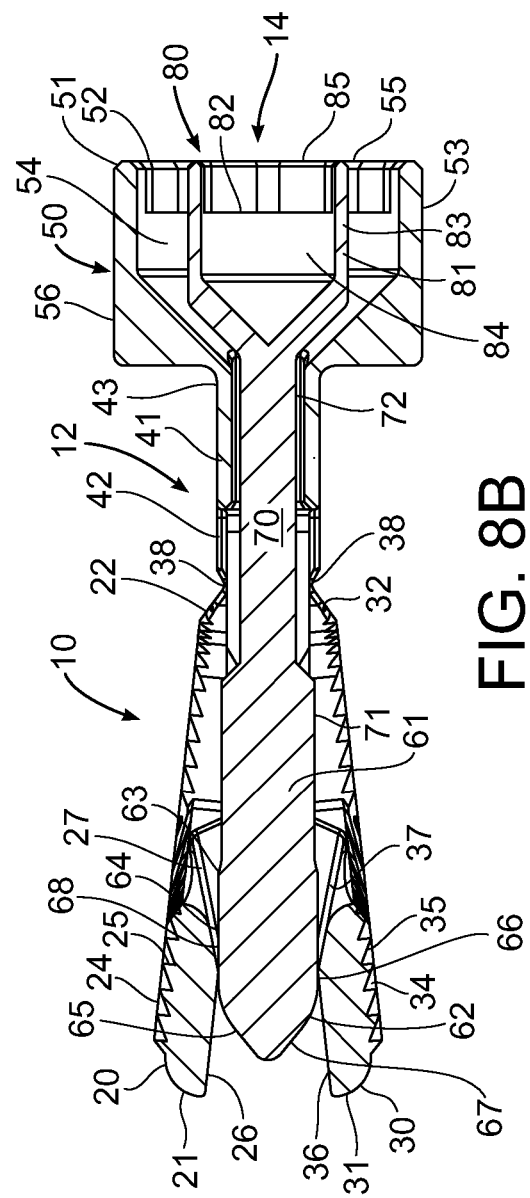

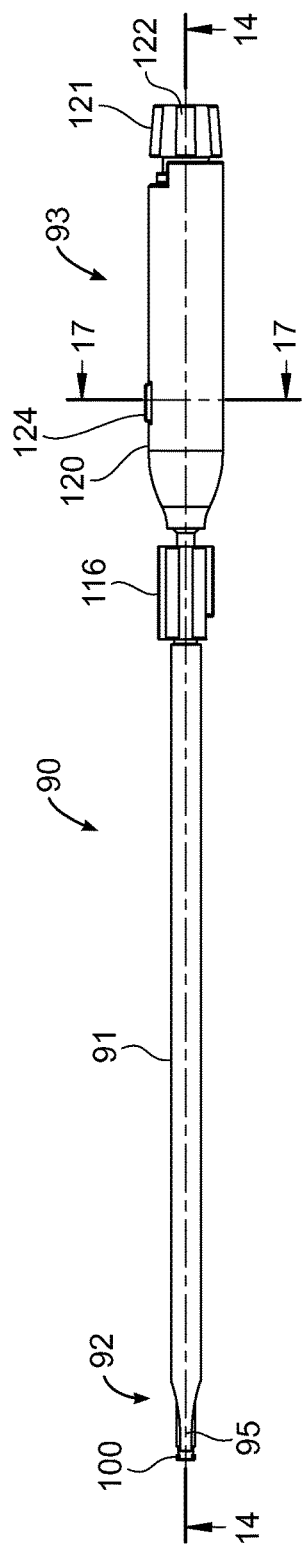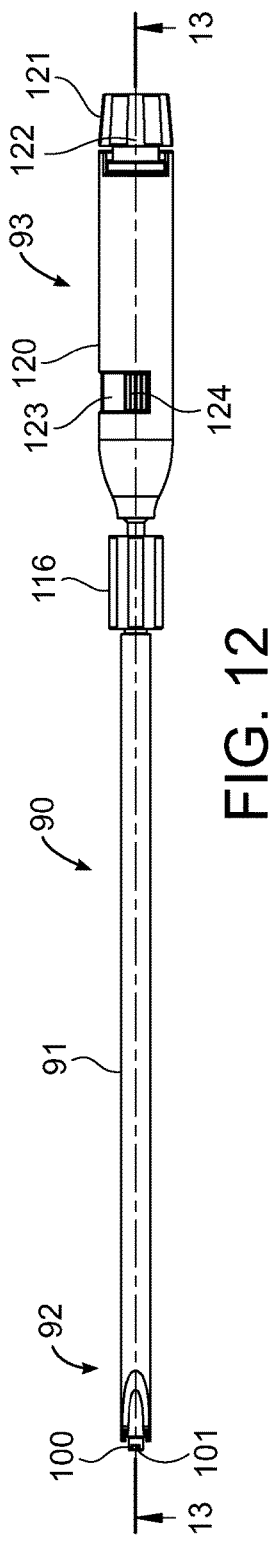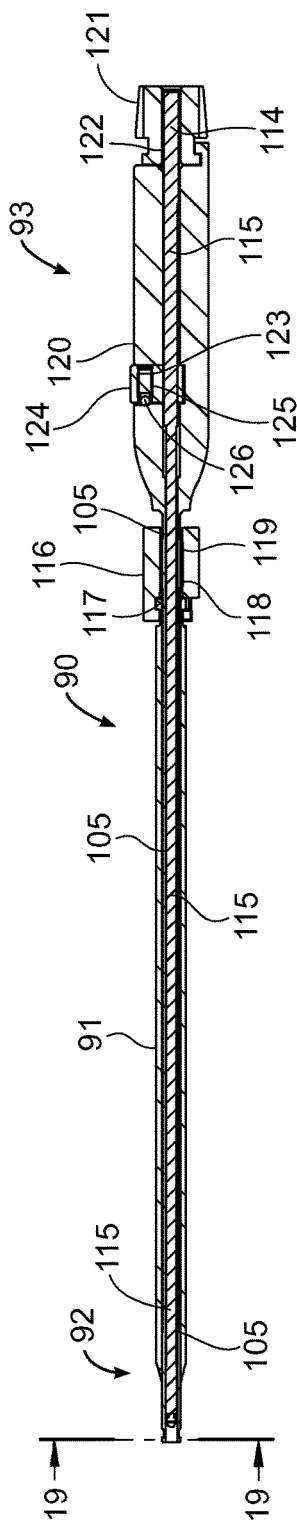

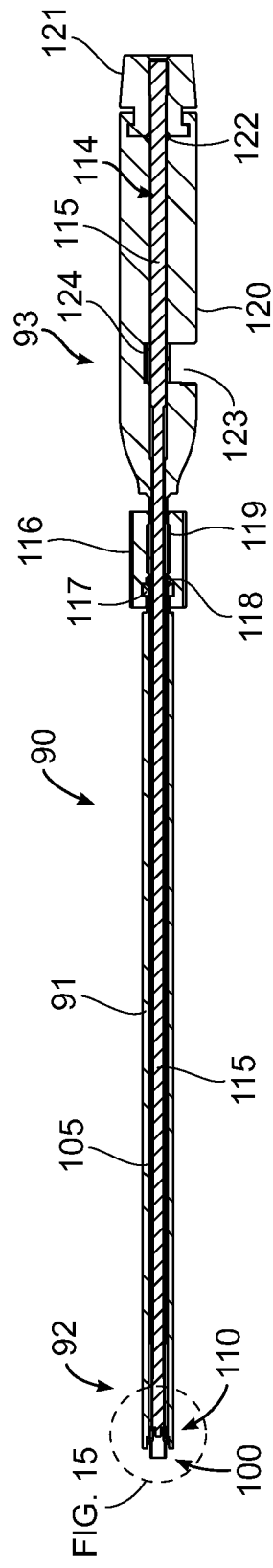
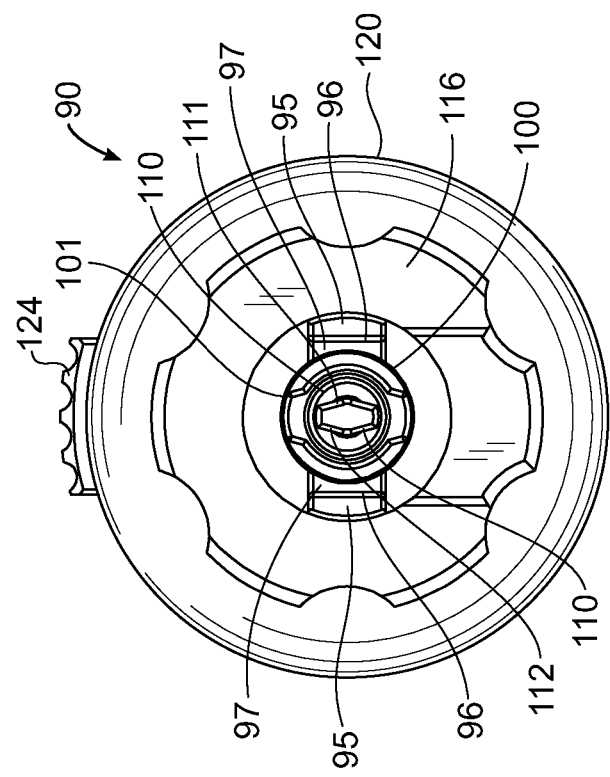
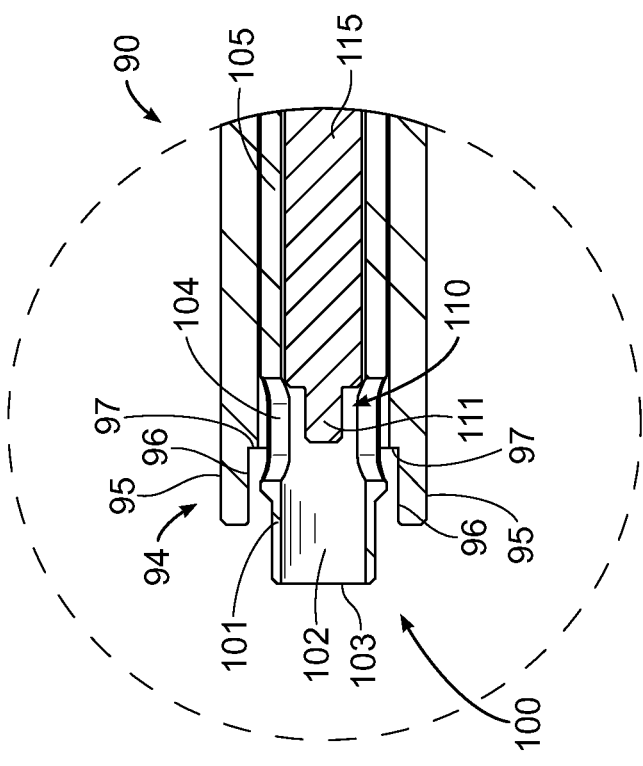
FIG. 14
FIG. 15
FIG. 16

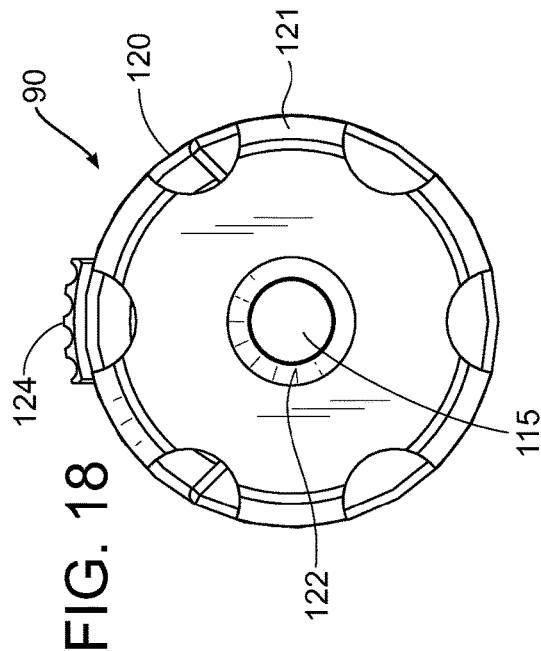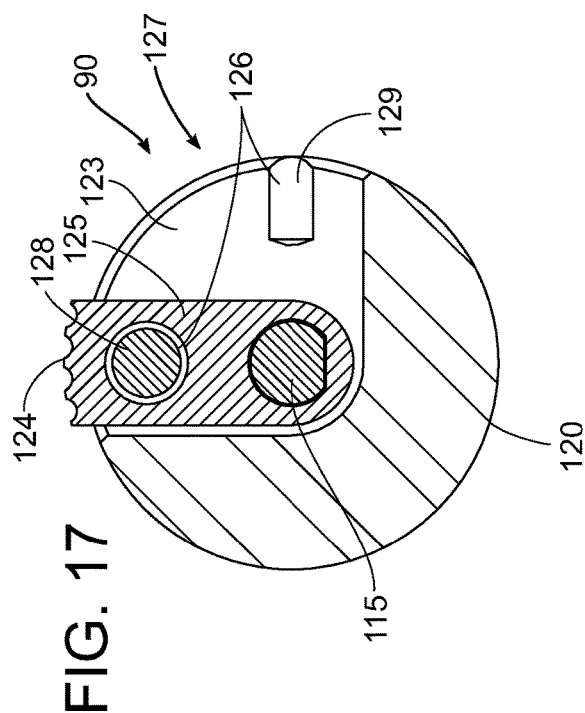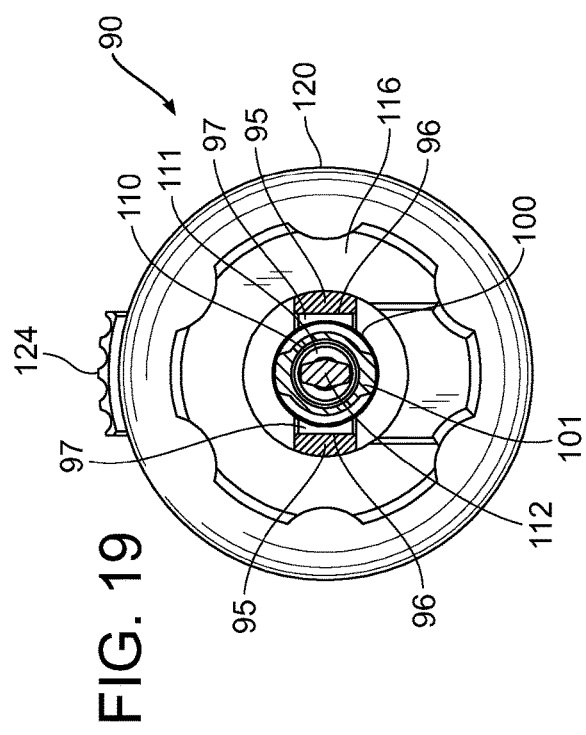

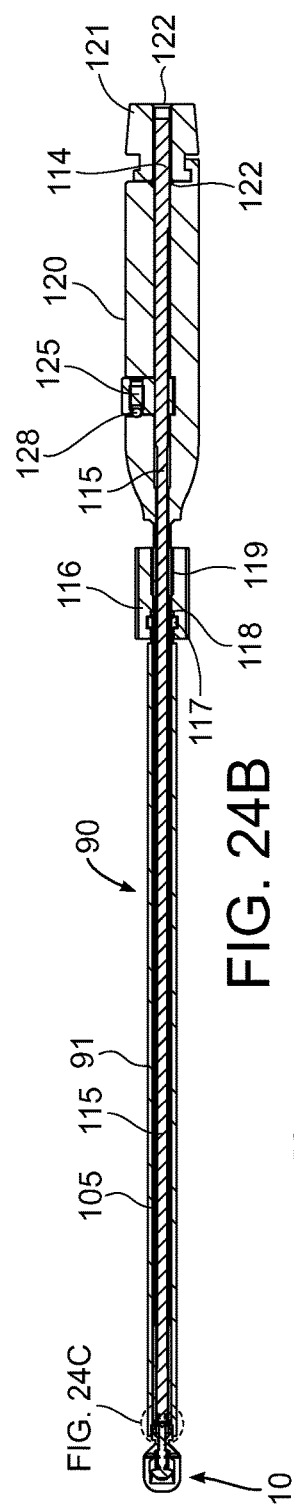
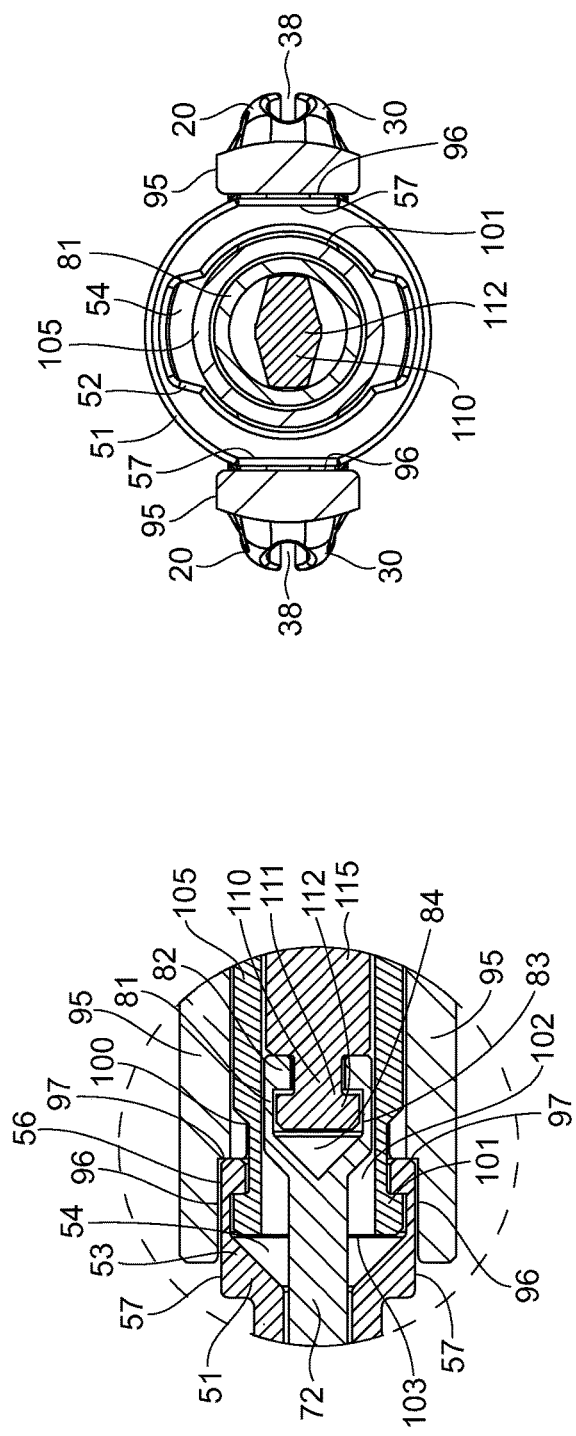
FIG. 24A  FIG. 24B  FIG. 24C  FIG. 24D

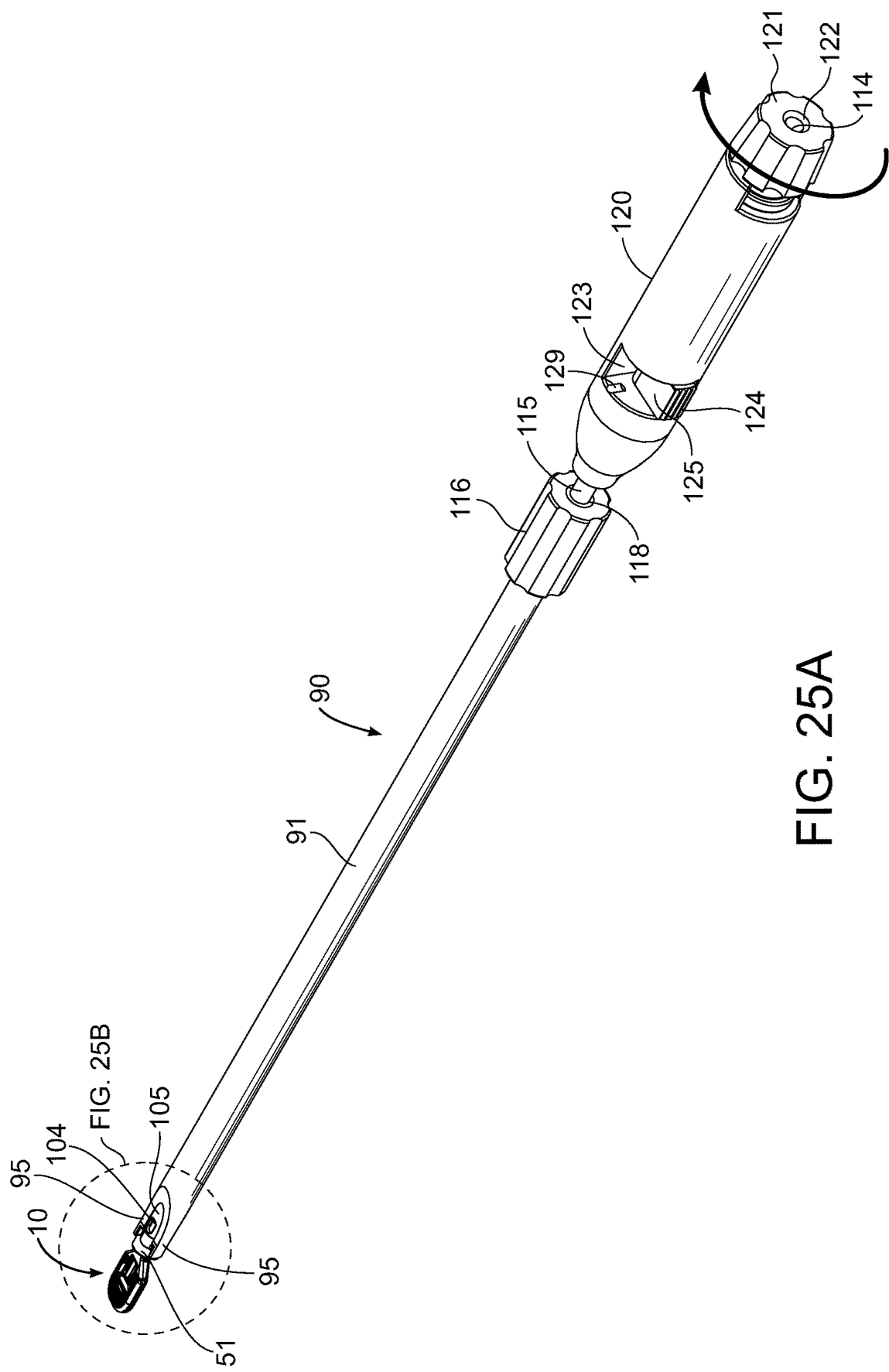

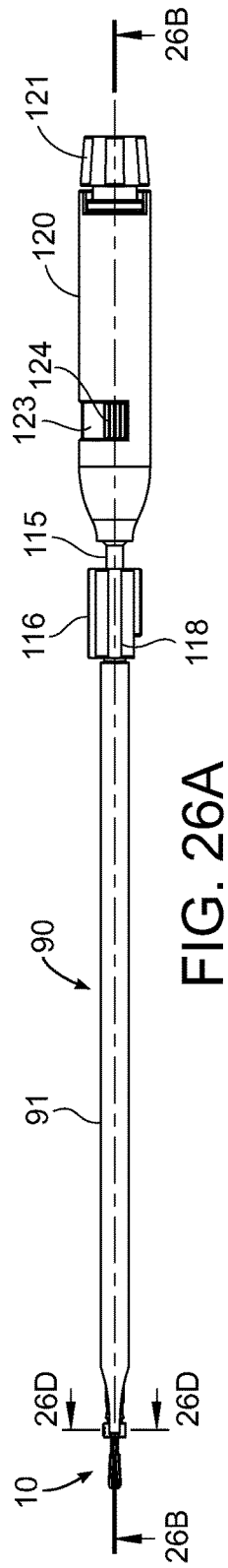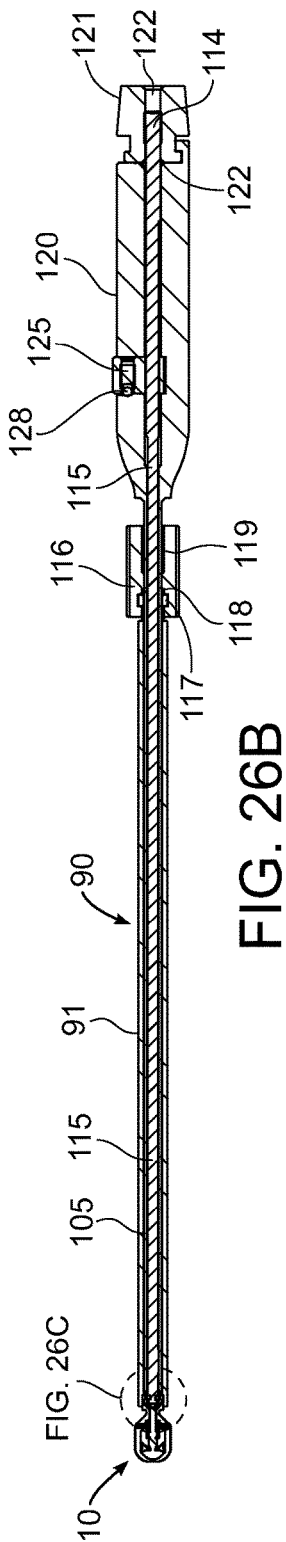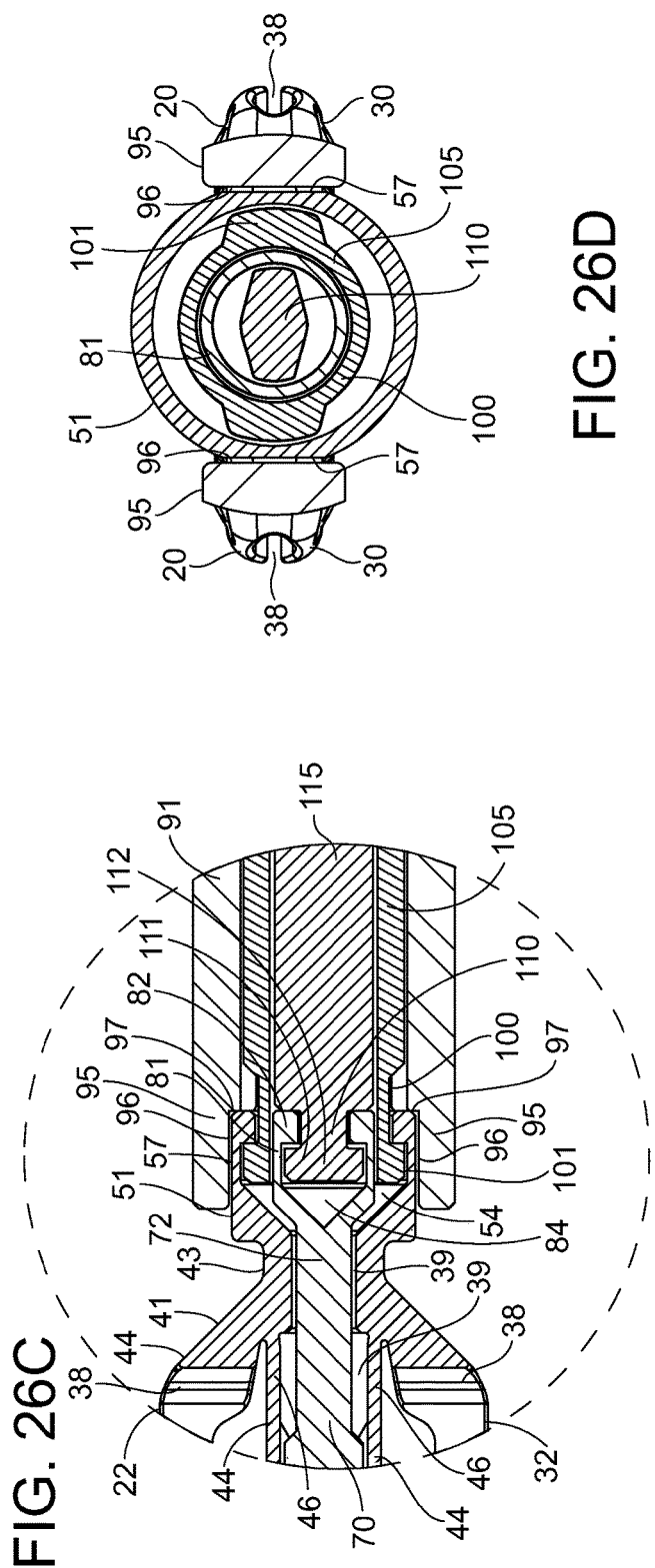
FIG. 26A  FIG. 26B  FIG. 26C  FIG. 26D

DISTALLY EXPANDING FACET JOINT IMPLANT AND DELIVERY DEVICE

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND

Field

Example embodiments in general relate to a distally expanding facet joint implant and delivery device for distracting the joint between facets of adjacent vertebrae of the spine, including cervical vertebrae, to provide nerve root decompression, maintain or improve vertebral alignment, and enhance spinal stability.

Related Art

Any discussion of the related art throughout the specification should in no way be considered as an admission that such related art is widely known or forms part of common general knowledge in the field.

Spine degeneration is a major burden to society. The current growth of the aging population is linked to a rise in cases of age-related spine joint degenerative change or arthropathy, which is a leading cause of chronic neck and back pain. The socioeconomic costs of degenerative spine disease are large. Such costs include both direct costs, such as payments for treatment of pain and neurologic disorders, and indirect costs from loss of work and frequent sick leaves.

The spinal column is composed of 33 vertebrae, separated by intervertebral discs and held together with ligaments and muscles. The spinal column provides an axial support for the human body in addition to its function as a protector to the spinal cord and its emerging nerve roots. Movement within each spine segment (adjacent superior and inferior vertebrae) is facilitated by the anteriorly located intervertebral discs and two posterior facet joints. The series of these joints between adjacent vertebrae of the spinal column permit the complex flexible movements of the spinal column.

The aging process often leads to degenerative changes that impact the structure of the spine joints. The process involves dehydration of the intervertebral discs resulting in reduction of disc height. Subsequently, friction between the joint surfaces occurs and a process of degeneration and local inflammation begins. The joints then become stiffer and the ligaments become thickened and less elastic. The overall process is collectively named spondylosis. Spondylosis leads to reduction in the size of the neural foramens (the space where the nerves emerge from the spinal cord), disc herniation, and spinal stenosis resulting in axial neck and/or back pain and neurological compromise. As the degenerative changes advance and the intervertebral foramen narrowing progresses, compression of the nerve roots can occur leading to nerve damage. Such damage often manifests itself as numbness and weakness due to motor and sensory function loss in addition to persistent pain in what is called radiculopathy. Radiculopathy resulting from damage to the cervical nerve roots is referred to more particularly as cervical radiculopathy.

The main goal in treating radiculopathy is to decompress the affected nerve. This goal can be accomplished by direct nerve decompression and removal of the compressing element, or by distracting the inter-facet joints between adjacent superior and inferior vertebrae compressing the nerve. The two approaches are frequently combined. Typically, either an anterior procedure is performed that involves the removal of the collapsed intervertebral disc and replacement with a bone or synthetic cage, or a posterior procedure that involves laminectomy with or without facetectomy (facet removal). In either case, the procedure is often coupled with the addition of instrumentation between the involved vertebrae to stabilize them and facilitate their fusion together.

With respect to the cervical spine in particular, evidence has highlighted the importance of maintaining the natural cervical spine alignment during surgical treatment of cervical radiculopathy as maintaining the natural alignment is often associated with better neurological functional outcomes. Thus, surgical treatment of the cervical spine to counteract the effects of the degenerative process must incorporate cervical alignment to achieve the most beneficial outcome.

At the same time, the current trend is to employ minimally invasive surgical approaches to treat various spinal diseases because such approaches have been demonstrated to lead to less post-operative pain, less surgical blood loss, and earlier recovery from surgery. For treatment of cervical radiculopathy, the commonly performed minimally invasive technique utilizes the posterior approach and specially designed devices to distract the facet joint by inserting an implant inside the facet joint and, consequently, relieving the nerve root compression.

A number of different facet joint implants and delivery devices have been proposed. However, to date nearly all such implants have limited success in providing optimal distraction of a facet joint and, when used in a cervical facet joint, maintaining the natural lordosis and preventing excessive kyphosis of the cervical spine.

There thus remains a need for a facet joint implant that is distally expandable to distract the facet joints of affected adjacent superior and inferior vertebrae to decompress the neural foramens and relieve the symptoms of cervical radiculopathy and, when used with a cervical facet joint, to also maintain or improve proper cervical alignment. A device that expands more anteriorly when inserted in the facet joint is more likely to achieve anterior facet joint distraction, intervertebral space distraction, and widening of the intervertebral foramen in addition to correcting existing spondylolisthesis. There also remains a need for such an implant and a delivery device that are readily usable with minimally invasive, posterior surgical techniques, and that can be used and deployed while minimizing undesirable damage to the soft tissue around the facet joint. There also remains a need for such an implant and delivery device that are less complex, easier to manipulate and use, and more readily result in the implant being properly positioned and oriented in the facet joints of affected vertebrae. There further remains a need for such an implant that is more reliable in achieving its intended function despite having a smaller size that facilitates insertion inside the relatively limited facet joint space. There further remains a need for such an implant and delivery device wherein the placement and expansion of the implant is more readily and easily reversible. There still further remains a need for such an implant that adheres effectively to the facet bones of affected vertebrae, that facilitates post-operative bone fusion, and that effectively stabilizes the spine and prevents undesirable inter-facet movement. There still further remains a need for such an implant and delivery tool that are relatively simple, easy, and inexpensive to manufacture and assemble.

The example embodiments of a distally expanding facet joint implant and delivery device described herein seek to address these needs with respect mainly for cervical facet joints.

SUMMARY

An example embodiment is directed to a distally expanding facet joint implant and delivery device. The distally expanding facet joint implant includes an outer part and an inner part. The outer part includes a first facet plate, a second facet plate, and a hinge. The first facet plate has a first distal end portion, a first proximal end portion, and a first opening between the first distal end portion and the first proximal end portion. The second facet plate has a second distal end portion, a second proximal end portion, and a second opening between the second distal end portion and the second proximal end portion. The hinge connects the first proximal end portion of the first facet plate and the second proximal end portion of the second facet plate.

The inner part is at least partially exposed in the first opening and the second opening and includes a wedge-shaped engagement structure with a third distal end portion and a third proximal end portion. The inner part is movable relative to the outer part.

When the inner part is moved toward the first distal end portion of the first facet plate and the second distal end portion of the second facet plate, the distal end portion of the wedge engages the first facet plate and the second facet plate, the first distal end portion of the first facet plate and the second distal end portion of the second facet plate move apart, and the first proximal end portion of the first facet plate and the second proximal end portion of the second facet plate rotate on the hinge in a first direction until the facet joint implant assumes a distally expanded open state.

When the inner part is moved toward the first proximal end portion of the first facet plate and the second proximal end portion of the second facet plate, the first distal end portion of the first facet plate and the second distal end portion of the second facet plate move toward each other, and the first proximal end portion of the first facet plate and the second proximal end portion of the second facet plate rotate on the hinge in a second direction until the facet joint implant assumes a distally contracted closed state.

According to one aspect of the example embodiments, the outer and inner parts comprise first and second monolithic structures and are formed in a pre-assembled arrangement.

According to another aspect of the example embodiments, the first facet plate has a first exterior surface with a first plurality of serrations or spikes and the second facet plate has a second exterior surface with a second plurality of serrations or spikes. The serrations or spikes facilitate the facet joint implant adhering to the bony surfaces of the facets adjacent to a facet joint in which it is implanted when it is in the open state.

According to another aspect of the example embodiments, the first facet plate has a first interior surface with a first sloped portion, the second facet plate has a second interior surface with a second sloped portion, and the wedge has a third exterior surface with a third sloped portion and a fourth exterior surface with a fourth sloped portion. When the inner part of the facet joint implant is moved toward the first distal end portion of the first facet plate and the second distal end portion of the second facet plate, the third sloped portion of the third exterior surface of the wedge engages the first sloped portion of the first interior surface of the first facet plate, and the fourth sloped portion of the fourth exterior surface of the wedge engages the second sloped portion of the second interior surface of the second facet plate to cause the first distal end of the first facet plate and the second distal end of the second facet plate to expand apart until the facet joint implant assumes the distally expanded open state.

According to another aspect of the example embodiments, the outer part of the facet joint implant includes a first set of teeth and the inner part of the facet joint implant includes at least a first set of indents and a second set of indents. When the facet joint implant is in the closed state, the first set of teeth engage the first set of indents and when the facet joint implant assumes the distally contracted closed state, the first set of teeth engage the second set of indents. This helps hold the facet joint implant in the open or closed position and can provide physical feedback when the facet joint implant assumes the open and closed positions.

According to yet another aspect of the example embodiments, the outer part of the facet joint implant includes a first delivery device interface and the inner part includes a second delivery device interface. The first delivery device interface includes a first connector that is configured to selectively receive, be brought into engagement with, and be brought into locked engagement with a corresponding first connector of a delivery device. When the first connector is in locked engagement with the corresponding first connector, the facet joint implant is held in a fixed position and orientation relative to the delivery device. The second delivery device interface comprises a second connector that is configured to selectively receive, be brought into engagement with, and be brought into locked engagement with a corresponding second connector of a delivery device. When the second connector is in locked engagement with the corresponding second connector, motion can be selectively imparted to the inner part of the facet joint implant relative to the outer part of the facet joint implant to distally expand and contract the facet joint implant.

The delivery device adapted for use with the distally expanding facet joint implant has a distal end portion and a proximal end portion. The delivery device includes a corresponding first connector at the distal end portion that is configured to be brought into engagement with, be inserted in, and be brought into locked engagement with the first connector of the facet joint implant and when in locked engagement to hold the facet joint implant in a fixed position and orientation relative to the delivery device. The delivery device includes a corresponding second connector at the distal end portion that is configured to be brought into engagement with, be inserted in, and be brought into locked engagement with the second connector of the facet joint implant. When the corresponding second connector is in locked engagement with the second connector of the facet joint implant, the delivery device is operable to selectively impart motion to the inner part of the facet joint implant relative to the outer part of the facet joint implant to distally expand and contract the facet joint implant.

According to another aspect of the example embodiments, the delivery device includes an outer tube control knob that is coupled to an outer tube of the delivery device. The outer tube control knob is configured and is operable to advance the outer tube relative to the corresponding first connector of the delivery device and the first connector of the facet joint implant to ensure that the corresponding first connector and the first connector are brought into engagement and locked engagement only in proper alignment, and with surfaces of the first connector in secure engagement with support surfaces on the outer tube.

According to another aspect of the example embodiments, the delivery device includes a control handle located at the proximal end portion of the delivery device. The control handle is coupled with the corresponding first connector of the delivery device and is configured and operable to selectively bring the corresponding first connector into locked engagement with the first connector of the facet joint implant.

According to another aspect of the example embodiments, the delivery device includes an inner shaft control knob located at the proximal end portion of the delivery device. The inner shaft control knob is coupled with the corresponding second connector of the delivery device and is operable to selectively bring the corresponding second connector into and out of engagement with the second connector of the facet joint implant.

According to another aspect of the example embodiments, the delivery device includes a lock switch and a lock located at the proximal end portion of the delivery device. The lock switch is coupled with the corresponding second connector of the delivery device, and is configured and operable to selectively rotate the corresponding second connector between a first position wherein the corresponding second connector is not in locked engagement with the second connector of the facet joint implant, and a second position wherein the corresponding second connector is in locked engagement with the second connector. The lock is responsive to operation of the lock switch to hold or maintain the corresponding second connector in the second position wherein the corresponding second connector is in locked engagement.

There has thus been outlined, rather broadly, some of the embodiments of the distally expanding facet joint implant and delivery device in order that the detailed description thereof may be better understood, and in order that the present contribution to the art may be better appreciated. There are additional embodiments of the distally expanding facet joint implant and delivery device that will be described hereinafter and that will form the subject matter of the claims appended hereto. In this respect, before explaining at least one embodiment of the distally expanding facet joint implant and delivery device in detail, it is to be understood that the distally expanding facet joint implant and delivery device are not limited in their application to the details of construction or to the arrangements of the components set forth in the following description or illustrated in the drawings. The distally expanding facet joint implant and delivery device are capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 1A is a perspective view of a distally expanding facet joint implant in a closed state in accordance with an example embodiment.

FIG. 1B is a perspective view of a distally expanding facet joint implant in an open state in accordance with an example embodiment.

FIG. 2A is a side view of a distally expanding facet joint implant in a closed state in accordance with an example embodiment.

FIG. 2B is a side view of a distally expanding facet joint implant in an open state in accordance with an example embodiment.

FIG. 3A is a top view of a distally expanding facet joint implant in a closed state in accordance with an example embodiment.

FIG. 3B is a top view of a distally expanding facet joint implant in an open state in accordance with an example embodiment.

FIG. 4A is a bottom view of a distally expanding facet joint implant in a closed state in accordance with an example embodiment.

FIG. 4B is a bottom view of a distally expanding facet joint implant in an open state in accordance with an example embodiment.

FIG. 7A is a top cross-sectional view of a distally expanding facet joint implant in a closed state in accordance with an example embodiment.

FIG. 7B is a top cross-sectional view of a distally expanding facet joint implant in an open state in accordance with an example embodiment.

FIG. 8A is a side cross-sectional view of a distally expanding facet joint implant in a closed state in accordance with an example embodiment.

FIG. 8B is a side cross-sectional view of a distally expanding facet joint implant in an open state in accordance with an example embodiment.

FIG. 11 is a side view of a delivery device for use with a distally expanding facet joint implant in accordance with an example embodiment.

FIG. 12 is a top view of a delivery device for use with a distally expanding facet joint implant in accordance with an example embodiment.

FIG. 13 is a side cross-sectional view of a delivery device for use with a distally expanding facet joint implant in accordance with an example embodiment.

FIG. 14 is a top cross-sectional view of a delivery device for use with a distally expanding facet joint implant in accordance with an example embodiment.

FIG. 15 is an enlarged detail side view of the distal end portion of a delivery device for use with a distally expanding facet joint implant in accordance with an example embodiment.

FIG. 16 is a distal end view of a delivery device for use with a distally expanding facet joint implant in accordance with an example embodiment.

FIG. 17 is a proximal end portion cross-sectional view of a delivery device for use with a distally expanding facet joint implant in accordance with an example embodiment.

FIG. 18 is a proximal end view of a delivery device for use with a distally expanding facet joint implant in accordance with an example embodiment.

FIG. 19 is a distal end portion cross-sectional view of a delivery device for use with a distally expanding facet joint implant in accordance with an example embodiment.

FIG. 24A is a side view of a distally expanding facet joint implant and a delivery device for use with the implant showing the delivery device and an inner part of the implant in locked engagement in accordance with an example embodiment.

FIG. 24B is a top cross-sectional view of a distally expanding facet joint implant and a delivery device for use with the implant showing the delivery device and an inner part of the implant in locked engagement in accordance with an example embodiment.

FIG. 24C is an enlarged detail view of a proximal end portion of the distally expanding facet joint implant and a distal end portion of the delivery device for use with the implant as shown in FIG. 24B showing the delivery device and the inner part of the implant in locked engagement in accordance with an example embodiment.

FIG. 24D is a cross-sectional view of a proximal end portion of the distally expanding facet joint implant and a distal end portion of the delivery device for use with the implant as shown in FIG. 24A showing the delivery device and the inner part of the implant in locked engagement in accordance with an example embodiment.

FIG. 25A is a perspective view of a distally expanding facet joint implant and a delivery device for use with the implant showing the delivery device in locked engagement with an inner part of the implant and the inner part being translated into a distally expanding outer part of the implant in accordance with an example embodiment.

FIG. 26A is a side view of a distally expanding facet joint implant and a delivery device for use with the implant showing the delivery device in locked engagement with an inner part of the implant, the inner part translated into a distally expanding outer part of the implant, and the implant in an open state in accordance with an example embodiment.

FIG. 26B is a top cross-sectional view of a distally expanding facet joint implant and a delivery device for use with the implant showing the delivery device in locked engagement with an inner part of the implant, the inner part translated into a distally expanding outer part of the implant, and the implant in an open state in accordance with an example embodiment.

FIG. 26C is an enlarged detail view of a proximal end portion of the distally expanding facet joint implant and a distal end portion of the delivery device as shown in FIG. 26B showing the delivery device in locked engagement with the inner part of the implant, the inner part translated into the distally expanding outer part of the implant, and the implant in the open state in accordance with an example embodiment.

FIG. 26D is a cross-sectional view of a proximal end portion of the distally expanding facet joint implant and a distal end portion of the delivery device for use with the implant as shown in FIG. 26A showing the delivery device in locked engagement with the inner part of the implant, the inner part translated into the outer distally expanding part of the implant, and the implant in the open state in accordance with an example embodiment.

DETAILED DESCRIPTION

Figure 5A:
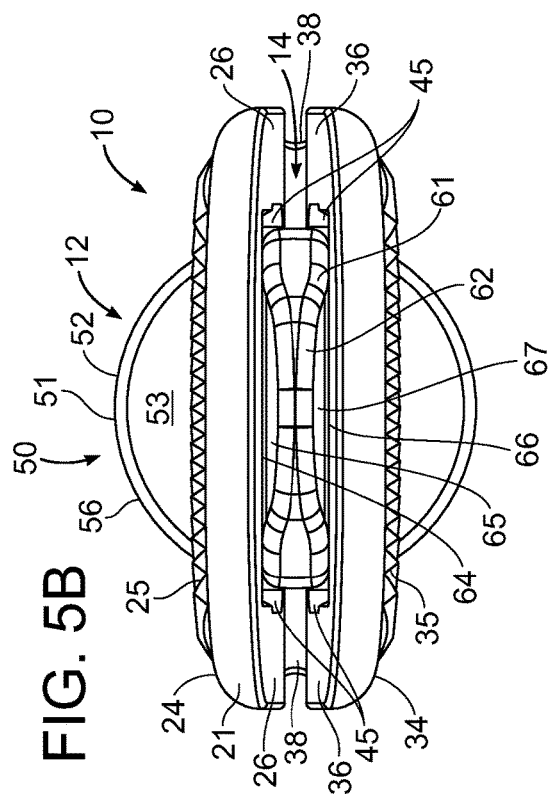
FIG. 5A is a distal end view of a distally expanding facet joint implant in a closed state in accordance with an example embodiment.
Figure 5B:
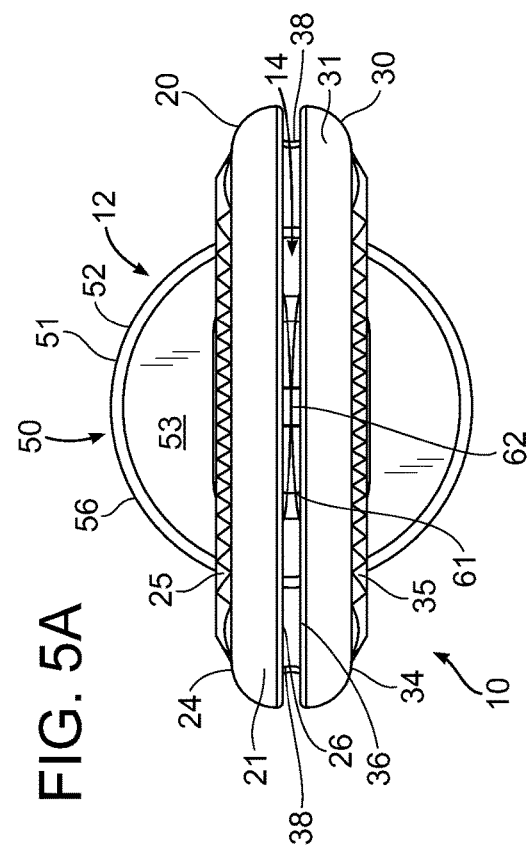
FIG. 5B is a distal end view of a distally expanding facet joint implant in an open state in accordance with an example embodiment.
Figure 6A:
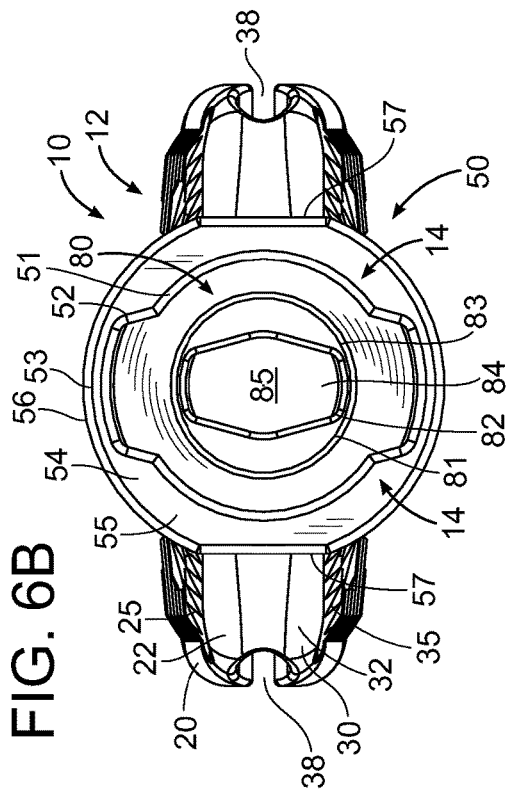
FIG. 6A is a proximal end view of a distally expanding facet joint implant in a closed state in accordance with an example embodiment.
Figure 6B:
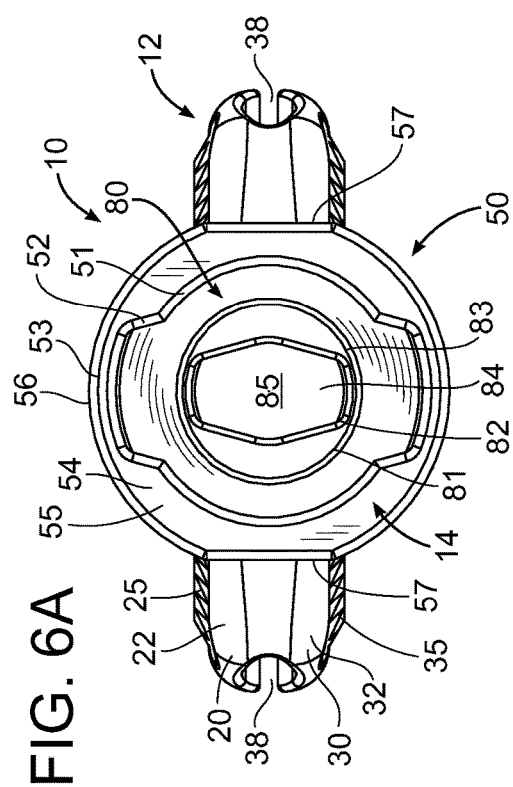
FIG. 6B is a proximal end view of a distally expanding facet joint implant in an open state in accordance with an example embodiment.

Example embodiments of a distally expanding facet joint implant and delivery device embodying the concepts of the present invention are described below with reference to the foregoing figures.

A. Overview

Example embodiments of a distally expanding facet joint implant generally include a facet joint implant 10 having an outer part 12 and an inner part 14. The facet joint implant 10 has an open state in which it is distally expanded and a closed state in which it is distally contracted. The inner part 14 is movable relative to the outer part 12 to cause the facet joint implant 10 to distally expand to the open state and to distally contract to the closed state.

The outer part 12 includes a first facet plate 20, a second facet plate 30, a hinge 38, a first set of teeth 40, and a first or outer connector 51. The first facet plate 20 has a first distal end portion 21, a first proximal end portion 22, and a first opening 23 between the first distal end portion 21 and the first proximal end portion 22. The second facet plate 30 has a second distal end portion 31, a second proximal end portion 32, and a second opening 33 between the second distal end portion 31 and the second proximal end portion 32. The hinge 38 connects the first proximal end portion 22 of the first facet plate 20 and the second proximal end portion of the second facet plate 30.

The first facet plate 20 has a first exterior surface 24 with a first plurality of serrations 25 and the second facet plate 30 has a second exterior surface with a second plurality of serrations 35. Alternatively, the serrations can be replaced by projections or spikes. When the facet joint implant 10 is implanted in a facet joint and in the distally expanded open state, the first plurality of serrations 25 and the second plurality of serrations 35 help adhere the facet joint implant to the bony surfaces of the facets adjacent to the facet joint so that the facet joint implant 10 does not move in the facet joint and the facet joint and adjacent facets are strengthened and stabilized. The bone of the facets also can grow into the first plurality of serrations 25 and the second plurality of serrations 35 and through the first opening 23 in the first facet plate 20 and the second opening 33 in the second facet plate to help fuse the facets adjacent to the facet joint and further improve the strength and stability of the facet joint and the surrounding facets.

The inner part 14 includes a wedge 61 with a third distal end portion 62 and a third proximal end portion 63, a second or inner connector 81, an elongated connector 70 connecting the second connector 81 and the wedge 61, and a first set of indents 73 and a second set of indents 74 formed on the elongated connector 70. The inner part 14 is movable relative to the outer part 12 and is at least partially exposed in the first opening 23 of the first facet plate 20 and the second opening 33 of the second facet plate 30.

When the inner part 12 is caused to move toward the first distal end portion 21 of the first facet plate 20 and the second distal end portion 31 of the second facet plate 30, the third distal end portion 62 of the wedge 61 engages the first facet plate 20 and the second facet plate 30. This in turn causes the first distal end portion 21 of the first facet plate 20 and the second distal end portion 31 of the second facet plate 30 to move apart until the facet joint implant 10 reaches the distally expanded open state. As the first distal end portion 21 of the first facet plate 20 and the second distal end portion 31 of the second facet plate 30 move apart, the first proximal end portion 22 of the first facet plate 20 and the second proximal end portion 32 of the second facet plate 30 rotate on the hinge 38 in a first direction.

In the distally expanded open state, the first set of teeth 40 on the outer part 12 of the facet joint implant 10 engage the second set of indents 74 on the elongated connector 70 of the inner part 14 of the facet joint implant 10, provide physical feedback, and help maintain the facet joint implant 10 in the open position.

When the inner part 12 is moved toward the first proximal end portion 22 of the first facet plate 20 and the second proximal end portion 32 of the second facet plate 30, the first distal end portion 21 of the first facet plate 20 and the second distal end portion 31 of the second facet plate 30 move toward each other until the facet joint implant 10 reaches the distally contracted closed state. As the first distal end portion 21 of the first facet plate 20 and the second distal end portion 31 of the second facet plate 30 move toward each other, the first proximal end portion 22 of the first facet plate 20 and the second proximal end portion 32 of the second facet plate 30 rotate on the hinge 38 in a second direction opposite to the first direction.

In the distally contracted closed state, the first set of teeth 40 on the outer part 12 of the facet joint implant 10 engage the first set of indents 74 on the elongated connector 70 of the inner part 14 of the facet joint implant 10, provide physical feedback, and help maintain the facet joint implant 10 in the closed position.

The first or outer connector 51 of the outer part 12 is configured to be selectively engaged by and brought into locked engagement with a corresponding first or outer connector 100 of a delivery device 90 to hold the facet joint implant 10 in a fixed orientation relative to the delivery device for introduction into the body of a patient, delivery to a facet joint in which the facet joint implant 10 is to be implanted, and insertion and positioning in the facet joint. The second or inner connector 81 of the inner part 14 of the facet joint implant 10 is configured to be selectively engaged by and brought into locked engagement with a corresponding second or inner connector 110 of the delivery device 90 to impart motion to the inner part 14 of the facet joint implant 10, and more specifically the wedge 61, relative to the outer part 12 of the facet joint implant 10, and more specifically the first facet plate 20 and the second facet plate 30. The first or outer connector 51 and the second or inner connector 81 are arranged concentrically with the first connector 51 extending around the second connector 81.

Example embodiments of the delivery device 90 for use with the distally expanding facet joint implant 10 generally include a distal end portion 92 and a proximal end portion 93, an elongated hollow outer tube 91, the corresponding first or outer connector 100, and the corresponding second or inner connector 110. The corresponding first connector 100 and the corresponding second connector 110 are located at the distal end portion 92 of the delivery device 90.

The delivery device 90 also includes an elongated hollow inner tube 105 that extends from the corresponding first connector 100 to the proximal end portion 93 and an elongated inner shaft 115 that extends from the corresponding second connector 110 to the proximal end portion of the delivery device 90.

The delivery device 90 also includes an outer tube control knob 116, a control handle 120, an inner shaft control knob 121, and a lock switch 124 and lock 126. The outer tube control knob 116, control handle 120, inner shaft control knob 121, and lock switch 124 and lock 126 are located at the proximal end portion 93 of the delivery device 90.

The corresponding first connector 100 and the corresponding second connector 110 are arranged concentrically with the corresponding first connector 100 extending around the corresponding second connector 110. The corresponding first connector 100 and the corresponding second connector 110 are at least partially contained within the hollow outer tube 91. The inner tube 105 and the inner shaft 115 are at least partially contained within the hollow outer tube 91 and are arranged concentrically with the inner shaft 115 being contained at least partially in the inner tube 105.

The outer tube control knob 116 is coupled with the hollow outer tube 91 and is configured and operable to advance the outer tube 91 relative to the corresponding first connector of the delivery device and the first connector of the facet joint implant so that when the corresponding first connector and the first connector are brought into locked engagement, surfaces of the first connector are brought into secure engagement with support surfaces on the outer tube.

The control handle 120 is coupled with the corresponding first connector 100 and is operable to bring the corresponding first connector 100 into engagement with the first connector 51 of the facet joint implant 10 by inserting the corresponding first connector 100 into the first connector 51. The control handle 120 is also configured and operable to bring the corresponding first connector 100 into locked engagement with the first connector 51 by rotating the corresponding first connector 100 relative to the first connector 51.

The inner shaft control knob 121 is rotatably connected to the control handle 120 and is coupled with the corresponding second connector 110 by a threaded coupling 122 with the inner shaft 115. The inner shaft control knob 121 rotates on the threaded coupling 122 relative to the inner shaft 115. The inner shaft control knob 121 is configured and is operable to be selectively rotated to cause the corresponding second connector 110 to move toward the distal end portion 92 and the proximal end portion 93 of the delivery device 90, depending on the direction in which it is rotated. When the inner shaft control knob 121 is rotated in a first direction the corresponding second connector 110 moves toward the distal end portion 92 and into engagement with the second connector 81 of the facet joint implant 10. When the inner shaft control knob 121 is rotated in a second opposite direction the corresponding second connector 110 moves toward the proximal end portion 93 and out of engagement with the second connector 81.

The lock switch 124 is coupled with the inner shaft 115 and via the inner shaft 115 with the corresponding second connector 110. The lock switch 124 includes a lever 125 that is rotatable between a first (unlocked) position and a second (locked) position on the control handle 120. Rotation of the lever 125 between the first (unlocked) position and the second (locked) position correspondingly rotates the corresponding second connector 110. When the corresponding second connector 110 is in engagement with the second connector 81 of the facet joint implant 10, rotating the lever 125 from the first (unlocked) position to the second (locked) position brings the corresponding second connector 110 into locked engagement with the second connector 81. The lock 126 is responsive to rotation of the lever 125 to the second (locked) position to temporarily hold or lock the corresponding second connector 110 in locked engagement with the second connector 81.

With the first connector 51 of the facet joint implant 10 in locked engagement with the corresponding first connector 100 of the delivery device 90 and the second connector 81 of the facet joint implant 10 in locked engagement with the corresponding second connector 110 of the delivery device 90, the delivery device 90 can be manipulated to introduce the facet joint implant 10 into the body of a patient, guide it to a facet joint 140 in which it is to be implanted, and insert and position it within the facet joint 140.

Once the facet joint implant 10 is positioned in the facet joint 140, rotating the inner shaft control knob 121 further in the first direction causes the inner part 14 of the facet joint implant 10, and more specifically the wedge 61, to move distally relative to the outer part 12, and more specifically the first facet plate 20 and the second facet plate 30, and causes the facet joint implant 10 to distally expand to its open position. Rotating the inner shaft control knob 121 in the second opposite direction causes the inner part 14 to move proximally relative to the outer part 12 and causes the facet joint implant 10 to distally contract to its closed position.

B. Outer Part

Illustrated primarily in FIGS. 1A through 9B, the outer part 12 of the distally expanding facet joint implant 10 comprises a first facet plate 20, a second facet plate 30, a hinge 38, a first set of teeth 40, a connecting shoulder 41, and a first delivery device interface 50.

Preferably, the outer part 12 comprises a first monolithic structure in which all of the components are formed or fabricated together as a single structure. For example, the outer part 12 may be formed or fabricated using a suitable 3D printing method such as selective laser melting (SLM). Alternatively, suitable molding techniques can be employed. Also alternatively, one or more of the components of the outer part 12 can be fabricated separately via SLM, other 3D printing techniques, and/or suitable molding or machining processes, and can then be interconnected with the other components of the outer part 12 in any suitable manner.

Also preferably, the outer part 12 and the inner part 14 described below are formed at the same time, for example using a suitable 3D printing method such as SLM, and also are formed pre-assembled as illustrated in FIGS. 1A, 1B, and others. Alternatively, the outer part 12 and the inner part 14 may be separately fabricated and assembled as illustrated in the figures.

1. First and Second Facet Plates.

The first facet plate 20 and the second facet plate 30 of the distally expanding facet joint implant 10 are configured and are operable to engage the bony surfaces of the superior and inferior facets 143, 145 of a facet joint 140 and to distally expand and distally distract the facet joint 140 when the facet joint implant 10 is distally expanded.

The first facet plate 20 of the outer part 12 has a first distal end portion 21, a first proximal end portion 22, and a first opening 23 between the first distal end portion 21 and the first proximal end portion 22. The first facet plate 20 has a first exterior surface 24 with a first plurality of serrations 25 and a first interior surface 26.

The first interior surface 26 is generally opposed to a second interior surface 36 of second facet plate 30 described below. Preferably, at least a portion of the first interior surface 26 comprises a first sloped portion 27. Preferably, the first sloped portion 27 extends upwardly from the direction of the first distal end portion 21 of the first facet plate 20 toward the first proximal end portion 22 of the first facet plate 20. The first sloped portion 27 is adapted to be engaged by a third sloped portion 65 of a third exterior surface 64 of the wedge 61 of the inner part 14 of the facet joint implant 10 as described below.

The second facet plate 30 of the outer part 12 has a second distal end portion 31, a second proximal end portion 32, and a second opening 33 between the second distal end portion 31 and the second proximal end portion 32. The second facet plate 30 has a second exterior surface 34 with a second plurality of serrations 35 and a second interior surface 36.

The second interior surface 36 is generally opposed to the first interior surface 26 of the first facet plate 20 described above. Preferably, at least a portion of the second interior surface 36 comprises a second sloped portion 37. Preferably, the second sloped portion 37 extends upwardly from the direction of the second distal end portion 31 of the second facet plate 30 toward the second proximal end portion 32 of the second facet plate 30. The second sloped portion 37 is adapted to be engaged by a fourth sloped surface 67 of a fourth exterior surface 66 of the wedge 61 of the inner part 14 of the facet joint implant 10 as described below.

The first opening 23 of the first facet plate 20 and/or the second opening 33 of the second facet plate 30 at least partially expose the inner part 14. As will become apparent, this facilitates bone growth through and around the facet joint implant 10 to help fuse the superior and inferior facets 143, 145 adjacent to the facet joint 140 in which the facet joint implant 10 is implanted, and to thus strengthen and stabilize the facet joint 140 and the adjacent facets 143, 145. It also facilitates observation of the movement of the inner part 14 of the facet joint implant 10 relative to the outer part 12 of the facet joint implant 10, for example to confirm proper operation of the facet joint implant 10 prior to insertion and deployment.

The facet joint implant 10 has a closed position or state and an open position or state. Throughout the description herein, the terms "position" and "state" are employed interchangeably in this regard.

In the closed state, the first distal end portion 21 of the first facet plate 20 and the second distal end portion 31 of the second facet plate 30 are in close proximity, and the first interior surface 26 of the first facet plate 20 and the second interior surface 36 of the second facet plate 30 are in close proximity and approximately parallel. FIGS. 1A, 2A, 3A, 4A, 5A, 6A, 7A, and 8A among others illustrate the facet joint implant 10 in the closed state.

In the open state, the first distal end portion 21 of the first facet plate 20 and the second distal end portion 31 of the second facet plate 30 are spaced apart, and the first interior surface 26 of the first facet plate 20 and the second interior surface 36 of the second facet plate 30 are also spaced apart distally and at an acute angle. FIGS. 1B, 2B, 3B, 4B, 5B, 6B, 7B, and 8B among others illustrate the facet joint implant 10 in the open state.

The first plurality of serrations 25 on the first exterior surface 24 of the first facet plate 20 and the second plurality of serrations 35 on the second exterior surface 34 of the second facet plate 30 are configured and operable to engage the bony surfaces of the superior and inferior facets 143, 145 facing the facet joint 140 respectively when the facet joint implant 10 is positioned in the facet joint 140 and distally expanded in the open state or position. Alternatively or in addition to the first plurality of serrations 25 and the second plurality of serrations 35, spikes or other protrusions may be employed. The first plurality of serrations 25 and the second plurality of serrations 35 help the facet joint implant 10 to adhere to the bony surfaces of the superior and inferior facets 143, 145, to prevent movement of the facet joint implant 10 within the facet joint 140, and to stabilize and strengthen the facet joint 140 and the adjacent superior and inferior vertebrae. These effects are further enhanced as bone from the adjacent facets 143, 145 grows into the first and second pluralities of serrations 25, 35.

The first facet plate 20 and the second facet plate 30 of the example embodiments are illustrated as being approximately rectangular in shape and as having the same shape and dimensions. However, persons skilled in the art will appreciate that the first facet plate 20 and the second facet plate 30 may be formed with various shapes and dimensions, and that the shapes and dimensions of the first facet plate 20 and the second facet plate 30 may be different, provided the shapes and dimensions are suitable to achieve the objectives identified herein.

Similarly, in the example embodiments the first opening 23 in the first facet plate 20 and the second opening 33 in the second facet plate 30 have the same shape and dimensions and extend to the first proximal end portion 22 of the first facet plate 20 and to the second proximal end portion 32 of the second facet plate 30 respectively as illustrated in FIGS. 1A, 1B, 3A, 3B, 4A, 4B, and others. However, persons skilled in the art will appreciate that the first opening 23 and the second opening 33 may have various shapes and dimensions provided the shapes and dimensions are suitable to achieve the objectives identified herein. Persons skilled in the art also will appreciate that the first opening 23 need not necessarily extend to the first proximal end portion 22 of the first facet plate 20 but may be completely enclosed by the first exterior surface 24 of the first facet plate 20, and that the second opening 33 need not necessarily extend to the second proximal end portion 32 of the second facet plate 30 but may be completely enclosed by the second exterior surface 34 of the second facet plate 30.

2. Hinge.

The hinge 38 connects the first proximal end portion 22 of the first facet plate 20 and the second proximal end portion 32 of the second facet plate 30. The hinge 38 is preferably positioned between the first proximal end portion 22 of the first facet plate 20 and the second proximal end portion 32 of the second facet plate 30. Preferably the hinge 38 is formed as a single monolithic structure with the first facet plate 20 and the second facet plate 30. Preferably the hinge 38 comprises a living hinge. Alternatively, the hinge 38 can be formed as a separate structure and attached or connected to and between the first proximal end portion 22 of the first facet plate 20 and the second proximal end portion 32 of the second facet plate 30 in any suitable manner.

In the example embodiments, the hinge 38 extends across substantially the entire width of the first proximal end portion 22 of the first facet plate 20 and the second proximal end portion 32 of the second facet plate 30 except where it is interrupted by the first opening 23 in the first facet plate 20 and the second opening 33 in the second facet plate 30. Persons skilled in the art will appreciate that the hinge 38 need not necessarily extend across substantially the entire width of the first proximal end portion 22 of the first facet plate 20 and the second proximal end portion 32 of the second facet plate 30 in all applications, however, and that it may be provided at select points between the first proximal end portion 22 of the first facet plate 20 and the second proximal end portion 32 of the second facet plate 30 as desired for various applications.

The hinge 38 has a third opening 39. The third opening 39 is shaped and configured to allow an elongated connector 70 of the inner part 14 to extend through the third opening 39 and to move distally and proximally relative to the first facet plate 20 and the second facet plate 30 of the outer part 12 as described below.

When the first distal end portion 21 of the first facet plate 20 and the second distal end portion 31 of the second facet plate 30 expand apart, the first proximal end portion 22 of the first facet plate 20 and the second proximal end portion 32 of the second facet plate 30 rotate in opposite directions around the axis of the hinge 38. In the example embodiments, the first proximal end portion 22 of the first facet plate 20 rotates clockwise about the axis while the second proximal end portion 32 of the second facet plate 30 rotates counter-clockwise about the axis.

Accordingly, the first proximal end portion 22 of the first facet plate 20 and the second proximal end portion 32 of the second facet plate 30 remain in close proximity as the first distal end portion 21 of the first facet plate 20 and the second distal end portion 31 of the second facet plate 30 expand apart. The first proximal end portion 22 of the first facet plate 20 and the second proximal end portion 32 of the second facet plate 30 remain in close proximity even when the facet joint implant 10 is in the open state.

3. First Set of Teeth.

In the example embodiments, the first set of teeth 40 are adapted and configured to selectively engage a first set of indents 73 and a second set of indents 74 on the inner part 14 of the facet joint implant 10 to securely hold the facet joint implant 10 in a selected position of distal expansion as further described below. More specifically, the first set of teeth 40, the first set of indents 73, and the second set of indents 74 are configured, are relatively positioned, and are operable to function like a ratchet to help hold the inner part 14 of the facet joint implant 10 in one of two selected positions relative to the outer part 12 of the facet joint implant 10, and hence the facet joint implant 10 in one of two selected states or positions of distal expansion.

For example, the first set of teeth 40, the first set of indents 73, and the second set of indents 74 are preferably positioned relative to one another so that when the facet joint implant 10 is in the closed state, the first set of teeth 40 is engaged with the first set of indents 73 to help hold the facet joint implant 10 in the closed state. When the facet joint implant 10 is in the distally expanded open state, the first set of teeth 40 is engaged with the second set of indents 74 to help hold the facet joint implant 10 in the open state.

In the example embodiments, the first set of teeth 40 is formed as part of a first set of elongated fingers 44 having distal end portions 45 and proximal end portions 46. The first set of teeth 40 is formed at the distal end portions 45 of the first set of elongated fingers 44 with one tooth of the first set of teeth 40 formed on the distal end portion 45 of each elongated finger of the first set of elongated fingers 44. The proximal end portions 46 of the first set of elongated fingers 44 are attached or connected to a distal end portion 42 of the connecting shoulder 41 of the outer part 12 of the facet joint implant 10. In the example embodiments, the distal end portion 42 of the connecting shoulder 41 abuts and is attached or connected to the hinge 38 of the outer part 12. The connecting shoulder 41, the first set of elongated fingers 44, and the first set of teeth 40 are stationary relative to movement of the inner part 14 of the facet joint implant 10.

The elongated fingers of the first set of elongated fingers 44 extend distally from the distal end portion 42 of the connecting shoulder 41 preferably along the surfaces of opposite lateral sides 75 of the elongated connector 70 of the inner part 14 of the facet joint implant 10. The first set of teeth 40, and more specifically each tooth of the first set of teeth 40, faces inwardly toward and extends into contact with the surfaces of the opposite lateral sides 75 of the elongated connector 70, including the first set of indents 73 and the second set of indents 74, which are formed in the surfaces of the elongated connector 70.

The elongated fingers of the first set of elongated fingers 44 are formed and configured to be deformable and elastic so that the teeth of the first set of teeth 40 apply a force against the surfaces of the elongated connector 70 with which they are in contact. Preferably the force is insufficient to substantially impede movement of the inner part 14 of the facet joint implant 10 relative to the outer part 12 of the implant when the first set of teeth 40 are not engaged with either the first set of indents 73 or the second set of indents 74 on the elongated connector 70. At the same time, the force preferably is sufficient so that when the teeth of the first set of teeth 40 encounter the indents of either the first set of indents 73 or the second set of indents 74, the teeth are caused to securely engage and seat in the indents and to securely (but not irreversibly) hold the inner part 14 of the facet joint implant 10 in position relative to the outer part 12 of the facet joint implant 10. It is also preferred that the force be sufficient to produce a physical feedback, such as a clicking feel or sound, when the teeth engage and seat in the indents.

This in turn securely (but not irreversibly) holds the facet joint implant 10, and more specifically the first facet plate 20 and the second facet plate 30 of the outer part 12 of the facet joint implant 10, in one of two selected positions of distal expansion, which as described above may correspond to the closed state and the open state of the facet joint implant 10. The secure holding provided by the first set of teeth 40 and second set of indents 74 is particularly beneficial when the facet joint implant 10 is deployed in a facet joint 140 in the distally expanded open state. In that circumstance, the facet joint implant 10 can be subjected to substantial forces from the vertebrae adjacent the joint. The secure holding provided by the first set of teeth 40 and second set of indents 74 helps prevent the facet joint implant 10 from possibly inadvertently distally contracting and perhaps moving within the joint 140 or even being ejected, especially if an inter-facet connection plate, such as described below, is not used.

At the same time, and as also described below, the holding force provided by the first set of teeth 40 and at least the second set of indents 74 may or may not be so great as to prevent manually disengaging the first set of teeth 40 from the second set of indents 74, and manually causing the facet joint implant 10 to distally contract. For example, if it is deemed desirable or necessary to be able to reposition the facet joint implant 10 in the facet joint 140 or to remove it from the facet joint 140 once it has been distally expanded, the second set of indents 74 can be configured to permit the first set of teeth 140 to be manually disengaged from the second set of indents 74 by the application of a degree of force so that the facet joint implant 10 can be manually distally contracted. Alternatively, however, the indents 74 and teeth 40 can be made deeper or can be otherwise configured to substantially prevent the first set of teeth 40 from being disengaged, and thus substantially prevent the facet joint implant 10 from being distally contracted once it has been distally expanded.

It is preferred that the first set of teeth 40 of the outer part 12, and the first set of indents 73 and second set of indents 74 of the inner part 14 be at least partially visible through the first opening 23 in the first facet plate 20 and/or the second opening 33 in the second facet plate 30. This facilitates observation of the movement of the first set of teeth 40 relative to the lateral sides 75 of the elongated connector 75, the first set of indents 73, and the second set of indents, for example to confirm proper operation of the facet joint implant 10 prior to insertion and deployment.

Preferably the first set of teeth 40, the first set of elongated fingers 44, and the connecting shoulder 41 are formed as a single monolithic structure with the other components of the outer part 12 of the facet joint implant 10. Alternatively, one or more of the first set of teeth 40, the first set of elongated fingers 44, and the connecting shoulder 41 be formed as a separate structure or structures, and can be attached or connected with the other components of the outer part 12 in any suitable manner.

In the specific example embodiments illustrated, the first set of teeth 40 comprises a first set of two teeth and the first set of elongated fingers 44 comprises a first set of two elongated fingers with one tooth formed on each elongated finger. In addition, in the specific example embodiments illustrated, two sets of indents 77, 78 are provided on opposite lateral sides of the elongated connector 70. However, persons skilled in the art will appreciate that depending on particular circumstances and intended applications of the facet joint implant 10, more or fewer teeth, elongated fingers, and indents may be used. In addition, the arrangements of the teeth, elongated fingers, and indents may be altered. For example, the teeth and indents may be arranged to engage on adjacent sides of the elongated connector 70 rather than or in addition to opposite lateral sides 75. Further, additional sets of indents may be provided at additional locations to engage the teeth when the facet joint implant is in states of partial distal expansion rather than or in addition to the closed and open states described. The shapes of the teeth and indents may be varied. Still further, the teeth may be formed on other structures of the outer part 12 and the indents may be formed on other structures of the inner part 14. All of these variations can be made without deviating from the concepts of the invention provided they are consistent with achieving the objectives described herein.

4. First Delivery Device Interface and First (Outer) Connector.

The first delivery device interface 50 provides a connection interface to the outer part 12 of the facet joint implant 10 for a delivery device 90 described below. The first delivery device interface 50 is connected to the outer part 12 of the facet joint implant 10. More specifically, the first delivery device interface 50 is connected to the first proximal end portion 22 of the first facet plate 20 and to the second proximal end portion 32 of the second facet plate 30. Still more specifically, the first delivery device interface 50 is connected to the proximal end portion 43 of the connecting shoulder 41 and is connected via the connecting shoulder 41 to the first proximal end portion 22 of the first facet plate 20 and to the second proximal end portion 32 of the second facet plate 30.

Preferably, the connection of the first delivery device interface 50 to the outer part 12 of the facet joint implant 10 is a substantially fixed or similar connection or attachment that does not allow the first delivery device interface 50 to substantially rotate or otherwise move relative to the outer part 12. Rather, it is preferred that as the first delivery device interface 50 is moved, whether rotationally or otherwise, the outer part 12 of the facet joint implant 10 moves with it.

The first delivery device interface 50 of the facet joint implant 10 comprises a first or outer connector 51. The first connector 51 is configured to be selectively engaged by a corresponding first connector 100 of the delivery device 90 and to be brought into locking engagement with the corresponding first connector 100 to hold the facet joint implant 10 in a fixed orientation relative to the delivery device 90. In the example embodiments, the first connector 51 comprises a first bayonet connector 52. The first bayonet connector 52 is adapted and configured to receive, engage, and be in locked engagement with a first bayonet 101 of the corresponding first or outer connector 100 of the delivery device 90 as described below.

The first or outer connector 51 comprises a substantially cylindrical body 53 that defines an open interior space 54 with an open face 55. The body 53 has an exterior surface 56. The exterior surface 56 contains one or more flats 57 adapted and configured to engage corresponding structures of the delivery device 90 as described below.

The third opening 39 through the hinge 38 described previously also extends through the body of the connecting shoulder 41 and into the open interior space 54 of the first connector 51. The third opening 39 is dimensioned and configured to allow the elongated connector 70 of the inner part 14 of the facet joint implant 10 to extend through the third opening 39 and to move distally and proximally relative to the hinge 38, connecting shoulder 41, and first connector 51 of the outer part 12 of the facet joint implant 10.

As described further below, a second or inner connector 81 of a second delivery device interface 80 connected to the inner part 14 of the facet joint implant 10 is fixedly connected or attached to a proximal end of the elongated connector 70. As the second or inner connector 81 is moved in a distal direction toward the first facet plate 20 and the second facet plate 30 it enters the open interior space 54 of the first or outer connector 51 through the open face 55 and the first or outer connector 51 extends around the second or inner connector 81. In the example embodiments, the first or outer connector 51 and the second or inner connector 81 are arranged to be substantially concentric, although that is a preference and not always necessary. As the second or inner connector 81 is moved in a proximal direction away from the first facet plate 20 and the second facet plate 30, it exits the open interior space 54 of the first or outer connector 51 through the open face 55 and is exposed outside the first or outer connector 51.

When the first connector 51 of the outer part 12 of the facet joint implant 10 is in locked engagement with the corresponding first connector 100 of the delivery device 90, the facet joint implant 10 is securely held in a fixed position and orientation relative to the delivery device 90 and the position and orientation of the facet joint implant 10 can be manipulated using the delivery device 90. This facilitates the positioning and orientation of the facet joint implant 10 for insertion into the body of a patient, delivery to a facet joint 140 in which it is to be implanted, and implantation in the facet joint 140.

Preferably, the first delivery device interface 50, more specifically the first or outer connector 51, and even more specifically the first bayonet connector 52 is configured to have an outer dimension greater than the expected or intended dimension of the posterior space between the superior and inferior facets 143, 145 of the facet joint 140 in which the facet joint implant 10 is to be implanted, i.e., the dimension of the expected or intended posterior opening 141 of the facet joint 140. This facilitates the ability to achieve proper positioning of the facet joint implant 10 in the facet joint 140 by allowing only the components of the outer part 12 and the inner part 14 necessary to distally distract the facet joint 140 to be inserted and preventing over-insertion of the facet joint implant 10 in the joint. In addition, the distance or dimension between the first delivery device interface 50, more specifically the first connector 51, and the distal end of the facet joint implant 10 can vary based on the facet size and the intended position of the maximum expansion of the distal end of the facet joint implant 10.

Preferably, the first delivery device interface 50, more specifically the first or outer connector 51, and even more specifically the first bayonet connector 52 is formed as a single monolithic structure with the other components of the outer part 12 of the facet joint implant 10. Alternatively, however, the first delivery device interface 50, more specifically the first or outer connector 51, and even more specifically the first bayonet connector 52 may be formed as a separate structure or structures, and may be fixedly attached or connected with the other components of the outer part 12 as described herein in any suitable manner.

C. Inner Part

Illustrated primarily in FIGS. 1A through 9E, the inner part 14 of the distally expanding facet joint implant 10 comprises a wedge 61, a first set of indents 73, a second set of indents 74, a second delivery interface 80 comprising a second or inner connector 81, and an elongated connector 70 between the wedge 61 and the second connector 81.

Preferably, the inner part 14 comprises a second monolithic structure, separate from the first monolithic structure of the outer part 12, in which all of the components of the inner part 14 are formed or fabricated together as a single structure. For example, the inner part 14 may be formed or fabricated using a suitable 3D printing method such as selective laser melting (SLM). Alternatively, suitable molding techniques can be employed. Also alternatively, one or more of the components of the inner part 14 can be fabricated separately via SLM, other 3D printing techniques, and/or suitable molding or machining processes, and can then be interconnected with the other components of the inner part 14 in any suitable manner.

Also preferably, the inner part 14 is formed at the same time as the outer part 12 described above, for example using a suitable 3D printing method such as SLM, and also is formed pre-assembled with the outer part 12 as illustrated in FIGS. 1A through 8B for example. Alternatively, the inner part 14 may be fabricated separately from the outer part 12 and assembled with the outer part 12 as illustrated in the figures.

As described further below, the inner part 14 of the facet joint implant 10 is moveable relative to the outer part 12. More specifically, the inner part 14 is movable in a distal direction toward the first facet plate 20 and the second facet plate 30, and in an opposite proximal direction away from the first facet plate 20 and the second facet plate 30. The movement of the inner part 14 relative to the outer part 12 causes the facet joint implant 10 to distally expand and contract between the open and closed states depending on the direction of motion of the inner part 14. As previously mentioned, the inner part 14 is at least partially exposed in the first opening 23 of the first facet plate 20 and/or the second opening 33 of the second facet plate 30 to facilitate controlling the movement of the inner part 14 relative to the outer part 12.

1. Wedge.

The inner part 14 includes an engagement structure 60 that is configured and operable to be selectively moved relative to the outer part 12 and to engage the outer part 12 to selectively cause the facet joint implant 10 to distally expand into the open state and distally contract into the closed state. More specifically, the engagement structure is configured and operable to be selectively moved in a distal direction toward and into engagement with the first facet plate 20 and the second facet plate 30 of the outer part 12 to selectively cause the first distal end portion 21 of the first facet plate 20 and the second distal end portion 31 of the second facet plate 30 to expand apart to place the facet joint implant 10 in the open state, and to be selectively moved in an opposite proximal direction away from and out of engagement with the first facet plate 20 and the second facet plate 30 of the outer part 12 to selectively cause the first distal end portion 21 of the first facet plate 20 and the second distal end portion 31 of the second facet plate 30 to contract toward each other and place the facet joint implant 10 in the closed state.

Although the engagement structure 60 may take any shape suitable to accomplish the above description, in the example embodiments, the inner part 14 comprises a wedge 61 as the engagement structure 60. The wedge 61 has a third distal end portion 62 and a third proximal end portion 63. The third distal end portion 62 is adjacent to and faces the first sloped portion 27 on the first interior surface 26 of the first facet plate 20 of the outer part 12 of the facet joint implant 10 and the second sloped portion 37 on the second interior surface 36 of the second facet plate 30 of the outer part 12 of the facet joint implant 10 when the facet joint implant 10 is in the closed state. The third proximal end portion 63 is connected to a distal end portion 71 of the elongated connector 70 of the inner part 14 and via the elongated connector 70 to the second delivery device interface 80 of the inner part 14 described below.

The wedge 61 also has a third exterior surface 64 and a fourth exterior surface 66. At least a portion of the third exterior surface 64 and a portion of the fourth exterior surface 66 are sloped. The sloped portion of the third exterior surface 64 comprises a third sloped portion 65 and the sloped portion of the fourth exterior surface 66 comprises a fourth sloped portion 65.

Preferably, the third sloped portion 65 of the third exterior surface 64 of the wedge 61 extends downwardly from the direction of the third proximal end portion 63 of the wedge 61 toward the third distal end portion 62 of the wedge 61. Preferably the fourth sloped portion 65 of the fourth exterior surface 66 of the wedge 61 extends downwardly from the direction of the third proximal end portion 63 of the wedge 61 toward the third distal end portion 62 of the wedge 61. As a result, the third distal end portion 62 of the wedge 61 has a first thickness and the third proximal end portion 63 of the wedge 61 has a second thickness greater than the first thickness.

The third sloped portion 65 of the third exterior surface 64 of the wedge 61 is adapted to engage and to move relative to the first sloped portion 27 of the first interior surface 26 of the first facet plate 20 of the outer part 12. The fourth sloped portion 65 of the fourth exterior surface 66 of the wedge 61 is adapted to engage and to move relative to the second sloped portion 37 of the second interior surface 36 of the second facet plate 30 of the outer part 12.

When the inner part 14 of the facet joint implant 10 is manipulated using the delivery device 90 and caused to move distally in the direction of the first facet plate 20 and the second facet plate 30 of the outer part 12 of the facet joint implant 10 as described below, the distally downward sloping third sloped portion 65 on the third exterior surface 64 of the wedge 61 engages and moves relative to the proximally upward sloping first sloped portion 27 of the first interior surface 26 of the first facet plate 20 of the outer part 12. Similarly, the distally downward sloping fourth sloped portion 65 on the fourth exterior surface 66 of the wedge 61 engages and moves relative to the proximally upward sloping second sloped portion 37 of the second interior surface 36 of the second facet plate 30 of the outer part 12.

As the wedge 61 continues to move distally between the first facet plate 20 and the second facet plate, the increasing thickness of the wedge between the first interior surface 26 of the first facet plate 20 and the second interior surface 36 of the second facet plate 30 causes the first distal end portion 21 of the first facet plate 20 and the second distal end portion 31 of the second facet plate 30 to move and apart until the facet joint implant 10 reaches the distally expanded open position. The first proximal end portion 22 of the first facet plate 20 and the second proximal end portion 32 of the second facet plate 30 rotate in a first set of opposite directions about the axis of the hinge 38 and remain in close proximity as the facet joint implant 10 is distally expanded, even when the facet joint implant 10 reaches the open position.

Similarly, when the inner part 14 of the facet joint implant 10 is manipulated using the delivery device 90 and caused to move proximally in the opposite direction away from the first facet plate 20 and the second facet plate 30 of the outer part 12 of the facet joint implant 10, the distally downward sloping third sloped portion 65 on the third exterior surface 64 of the wedge 61 moves relative to and in engagement with the proximally upward sloping first sloped portion 27 of the first interior surface 26 of the first facet plate 20 of the outer part 12, and the distally downward sloping fourth sloped portion 65 on the fourth exterior surface 66 of the wedge 61 moves relative to and in engagement with the proximally upward sloping second sloped portion 37 of the second interior surface 36 of the second facet plate 30 of the outer part 12.

As the wedge 61 continues to move proximally between the first facet plate 20 and the second facet plate, the decreasing thickness of the wedge between the first interior surface 26 of the first facet plate 20 and the second interior surface 36 of the second facet plate 30 causes the first distal end portion 21 of the first facet plate 20 and the second distal end portion 31 of the second facet plate 30 to move together or toward each other until the facet joint implant 10 reaches the distally contracted closed position. The first proximal end portion 22 of the first facet plate 20 and the second proximal end portion 32 of the second facet plate 30 rotate in a second set of opposite directions about the axis of the hinge 38 and remain in close proximity as the facet joint implant 10 is distally contracted and reaches the closed position.

Preferably the wedge 61 also has substantially flat surfaces 68 on the third exterior surface 64 between the third sloped portion 65 and the third proximal end portion 63 of the wedge 61 and on the fourth exterior surface 66 between the fourth sloped portion 67 and the third proximal end portion 63 of the wedge 61. The flat surfaces 68 are configured to help distribute the pressure or weight exerted on the facet joint implant 10 by the facet joint 140 over a wider surface area when the facet joint implant 10 is positioned in the facet joint 140 with the exterior surfaces 24, 34 of the first and second facet plates 20, 30 in contact with the interior facet surfaces 150, 152.

Preferably, the engagement structure 60 and more specifically the wedge 61 is formed as a single monolithic structure with the other components of the inner part 14 of the facet joint implant 10. Alternatively, however, the engagement structure 60 and more specifically the wedge 61 may be formed as a separate structure or structures, and may be fixedly attached or connected with the other components of the inner part 14 as described herein in any suitable manner.

2. Indents.

As described above, the inner part 14 of the facet joint implant 10 comprises a first set of indents 73, wherein the first set of indents 73 is located on the inner part 14 so that when the facet joint implant 10 is in the closed state, the first set of teeth 40 of the outer part 12 of the facet joint implant 10 is engaged with the first set of indents 73. Similarly, the inner part 14 of the facet joint implant 10 comprises a second set of indents 74, wherein the second set of indents 74 is located on the inner part 14 so that when the facet joint implant 10 is in the open state, the first set of teeth of the outer part 12 is engaged with the second set of indents 74.

More specifically, and as described above, in the example embodiments the first set of indents 73 and the second set of indents 74 are formed in the surfaces of opposite lateral sides 75 of the elongated connector 70 of the inner part 14 of the facet joint implant 10 with the opposite lateral sides 75 facing corresponding teeth of a first set of teeth 40 formed on the outer part 12 of the facet joint implant 10. The first set of indents 73 and the second set of indents 74 are configured, are relatively positioned, and are operable to function like a ratchet with the first set of teeth 40 to help hold the inner part 14 of the facet joint implant 10 in one of two selected positions relative to the outer part 12 of the facet joint implant 10, and hence the facet joint implant 10 in one of two selected states or positions of distal expansion.

In the example embodiments, these two selected positions correspond to the closed state and the open state of the facet joint implant 10 respectively. Thus, the first set of indents 73 is formed on opposite lateral sides 75 of the elongated connector 70 at the distal end portion 71 of the elongated connector 70 at a first position that is just proximal to the third proximal end portion 63 of the wedge 61. At this first position, the first set of indents 73 align with the first set of teeth 40 of the outer part 12 of the facet joint implant 10 when the elongated connector 70 is positioned such that the third distal end portion 62 of the wedge 61 is adjacent to but not substantially engaged with the first interior surface 26 of the first facet plate 20 of the outer part 12 and the second interior surface 36 of the second facet plate 30 of the outer part 12. This corresponds to the distally contracted closed state of the facet joint implant 10.

Similarly, the second set of indents 74 is formed on the same opposite lateral sides 75 of the elongated connector 70 as the first set of indents 73 but at a second position that is spaced apart from the first position and is closer to the proximal end of the elongated connector 70 to which the second delivery device interface 80 is connected. At this second position, the second set of indents 74 aligns with the first set of teeth 40 of the outer part 12 when the wedge 61 is fully inserted between the first facet plate 20 and the second facet plate 30 with the third exterior surface 64 of the wedge 61 and the fourth interior surface 65 of the wedge engaged with the first interior surface 26 of the first facet plate 20 and the second interior surface 36 of the second facet plate 30 respectively. This corresponds to the distally expanded open state of the facet joint implant 10.

As described previously, the first set of indents 73 and the second set of indents 74 are preferably configured and dimensioned to facilitate the first set of teeth 40 securely engaging and seating in the indents to securely (but not irreversibly) hold the inner part 14 of the facet joint implant 10 in position relative to the outer part 12 of the facet joint implant 10. As mentioned above, it also is preferred that the indents be configured to provide a physical feedback, such as a clicking feel or sound, when the first set of teeth 40 engage and seat in the first set of indents 73 and the second set of indents 74.

The secure engagement and seating of the first set of teeth 40 in the indents is particularly beneficial when the facet joint implant 10 is deployed in a facet joint 140 in the distally expanded open state for the reasons explained above. As also described above, it is preferred that at least the second set of indents 74 are configured and dimensioned so that the force with which they engage and hold the first set of teeth 40 is sufficient to reliably keep the facet joint 140 distracted anteriorly. At the same time, the holding force may or may not be so great as to prevent an operator from manually disengaging the first set of teeth 40 from the second set of indents 74, and manually causing the facet joint implant 10 to distally contract. For example, if it is deemed desirable or necessary to be able to reposition the facet joint implant 10 in the facet joint 140 or to remove it from the facet joint 140 once it has been distally expanded, the second set of indents 74 can be configured to permit the first set of teeth 140 to be manually disengaged from the second set of indents 74 by the application of a degree of force so that the facet joint implant 10 can be manually distally contracted. Alternatively, however, the indents 74 and teeth 40 can be made deeper or can be otherwise configured to substantially prevent the first set of teeth 40 from being disengaged, and thus substantially prevent the facet joint implant 10 from being distally contracted once it has been distally expanded to the open state.

It is preferred that the first set of indents 73 and second set of indents 74 be at least partially visible through the first opening 23 in the first facet plate 20 and/or the second opening 33 in the second facet plate 30. This facilitates observation of the movement of the inner part 14 of the facet joint implant 10 relative to the outer part 12 of the facet joint implant 10, for example to confirm proper operation of the facet joint implant 10 prior to insertion and deployment.

It is also preferred that the first set of indents 73, the second set of indents 74, and the elongated connector 70 be formed as a single monolithic structure with each other and with the other components of the inner part 14 of the facet joint implant 10. Alternatively, however, the components may be formed as one or more separate structures, and can be attached or connected together and with the other components of the inner part 14 in any suitable manner.

In the specific example embodiments illustrated, the first set of indents 73 and the second set of indents 74 each comprise two indents located on opposite lateral sides of the elongated connector 70. However, persons skilled in the art will appreciate that depending on particular circumstances and intended applications of the facet joint implant 10, more or fewer indents may be used in each set and total. In addition, the arrangements of the indents may be altered. For example, indents may be arranged on adjacent sides of the elongated connector 70 rather than or in addition to opposite lateral sides 75. Further, additional sets of indents may be provided at additional locations to engage teeth of the outer part 12 when the facet joint implant is in states of partial distal expansion rather than or in addition to the closed and open states as described. The corresponding shapes of the indents and teeth may be varied. Still further, the indents may be formed on other structures of the inner part 14 rather than or in addition to the elongated connector 70. All of these variations can be made without deviating from the concepts of the invention provided they are consistent with achieving the objectives described herein.

3. Second Delivery Device Interface and Second (Inner) Connector.

The second delivery device interface 80 provides a connection interface to the inner part 14 of the facet joint implant 10 for the delivery device 90 described below.

The second delivery device interface 80 is connected to the inner part 14 of the facet joint implant 10. More specifically, the second delivery device interface 80 is connected to the wedge 61. Still more specifically, the second delivery device interface is connected to the third proximal end portion 63 of the wedge 61. Even more specifically, the second delivery device interface 80 is connected to the proximal end portion 72 of the elongated connector 70 and is connected via the elongated connector 70 to the third proximal end portion 63 of the wedge 61.

Preferably, the connection of the second delivery device interface 80 to the inner part 14 of the facet joint implant 10 is a substantially fixed or similar connection or attachment that does not allow the second delivery device interface 80 to substantially move relative to the inner part 14. Rather, it is preferred that as the second delivery device interface 80 is moved, the inner part 14 of the facet joint implant 10 moves with it relative to the outer part 12 of the facet joint implant 10.

The second delivery device interface 80 of the facet joint implant 10 comprises a second or inner connector 81. The second connector 81 is configured to be selectively engaged by and to be brought into locked engagement with a corresponding second connector 110 of the delivery device 90 to impart motion to the inner part 14 of the facet joint implant 10 relative to the outer part 12 of the facet joint implant 10. The second connector 81 is configured to be engaged by the corresponding second connector 110 by receiving the corresponding second connector 110 at least partially in the second connector 81. The second connector 81 is configured to be brought into locked engagement with the corresponding second connector 110 by permitting the corresponding second connector 110 to rotate within and relative to the second connector 81, for example by approximately 90 degrees.

In the example embodiments, the second connector 81 comprises a second bayonet connector 82. The second bayonet connector 82 is adapted and configured to receive, be engaged by, and be brought into locked engagement with a second bayonet 111 of the corresponding second connector 110 of the delivery device 90, which is described further below. The second bayonet connector 82 comprises a substantially cylindrical body 83 that defines an open interior space 84 with an open face 85 for receiving a second bayonet 111 of the corresponding second connector 110 of the delivery device 90. The open face 85 is shaped and adapted to permit the second bayonet 111 to be inserted into the open interior space 84 of the second bayonet connector 82 and to be brought into engagement with the second bayonet connector 82. The second bayonet connector 82 is further adapted and configured to be brought into locked engagement with the second bayonet 111 of the delivery device 90 by permitting the second bayonet 111 to rotate within and relative to the second bayonet connector 82, for example by approximately 90 degrees.

The shape of the open face 85 is adapted both to act as a key opening for a second key 113 of the delivery device 90 as described further below, and more importantly to prevent the second bayonet 111 from inadvertently exiting the second bayonet connector 82 once it is in locked engagement. Thus, the open face 85 is shaped to only allow the second bayonet 111 to be inserted in or to be withdrawn from the second bayonet connector 82 when the second bayonet 111 is in a particular orientation relative to the second bayonet connector 82. Conversely, the open face 85 is shaped and adapted to block the second bayonet 111 from being inserted into or withdrawn from the open interior space 84 of the second bayonet connector 82 when the second bayonet 111 is not in the particular orientation relative to the second bayonet connector 82.

As described above, as the second or inner connector 81 is moved in a distal direction toward the first facet plate 20 and the second facet plate 30 of the outer part 12 of the facet joint implant 10, the second connector 81 enters the open interior space 54 of the first or outer connector 51 of the outer part 12 through the open face 55 and the first or outer connector 51 extends around the second or inner connector 81. In the example embodiments, the first or outer connector 51 and the second or inner connector 81 are arranged to be substantially concentric, although that is a preference and is not always necessary. As the second or inner connector 81 is moved in a proximal direction away from the first facet plate 20 and the second facet plate 30, it exits the open interior space 54 of the first or outer connector 51 through the open face 55 and is exposed outside the first or outer connector 51.

As described previously, the third opening 39 through the hinge 38 of the outer part 12 of the facet joint implant 10 also extends through the body of the connecting shoulder 41 of the outer part 12 and into the open interior space 54 of the first connector 51 of the outer part 12. The elongated connector 70 of the inner part 14 extends through the third opening 39 and is movable within the third opening 39 in distal and proximal directions relative to the outer part 12 of the facet joint implant 10. Preferably, the second or inner connector 81, more specifically the second bayonet connector 82, and even more specifically the body 83 of the second bayonet connector 82, is configured and dimensioned relative to the third opening 39 so that the second connector 81 cannot enter the third opening 39 through the first or outer connector 51.

Because the second or inner connector 81 is fixedly connected to the elongated connector 70, when the second connector 81 is moved in a distal direction toward the first facet plate 20 and the second facet plate 30 of the outer part 12, so is the elongated connector 70. Similarly, when the second or inner connector 81 is moved in an opposite proximal direction away from the first facet plate 20 and the second facet plate 30 of the outer part 12, so is the elongated connector 70. Thus, moving the second or inner connector 81 also moves the inner part 14 of the facet joint implant 10 relative to the outer part 12 of the facet joint implant 10.

Accordingly, because the wedge 61 is connected at the distal end portion 71 of the elongated connector 70, moving the second or inner connector 81 in the distal direction toward the first facet plate 20 and the second facet plate 30 of the outer part 12 causes the wedge 61 to engage and move relative to the first facet plate 20 and the second facet plate 30, which in turn causes the facet joint implant 10 to distally expand to the open state in the manner previously described. Similarly, moving the second or inner connector 81 in the opposite proximal direction away from the first facet plate 20 and the second facet plate 30 of the outer part 12 causes the wedge 61 to move relative to and to disengage from the first facet plate 20 and the second facet plate 30, which in turn causes the facet joint implant 10 to distally contract to the closed state in the manner previously described.

When the second connector 81 of the inner part 14 of the facet joint implant 10 is in engagement with but not necessarily in locked engagement with the corresponding second connector 110 of the delivery device 90, the delivery device 90 can be manipulated as described below to selectively cause the second connector 81 and the inner part 14 of the facet joint implant 10, including the wedge 61, to move distally relative to the outer part 12, including the first facet plate 20 and the second facet plate 30. Thus, the delivery device 90 can be manipulated to selectively cause the facet joint implant 10 to distally expand from its closed state to its open state. This is possible because the wedge 61 is pushed in a distal direction, rather than pulled in a proximal direction, to cause the facet joint implant 10 to distally expand to the open state. When the second connector 81 is in locked engagement with the corresponding second connector 110, the delivery device 90 also can be manipulated as described below to selectively cause the second connector 81 and the wedge 61 to move proximally relative to the first facet plate 20 and the second facet plate 30. Thus, the delivery device 90 also can be manipulated to selectively cause the facet joint implant 10 to distally contract from the open state to the closed state in the manner described herein.

In the example embodiments illustrated in FIGS. 1A through 9B, the second delivery device interface 80, more specifically the second or inner connector 81, and even more specifically the second bayonet connector 82 is preferably formed as a single monolithic structure with the other components of the inner part 14 of the facet joint implant 10. Alternatively, however, the second delivery device interface 80, more specifically the second or inner connector 81, and even more specifically the second bayonet connector 82 may be formed as a separate structure or structures, and may be fixedly and rigidly attached or connected with the other components of the inner part 14 as described herein in any suitable manner.

Figure 9A:
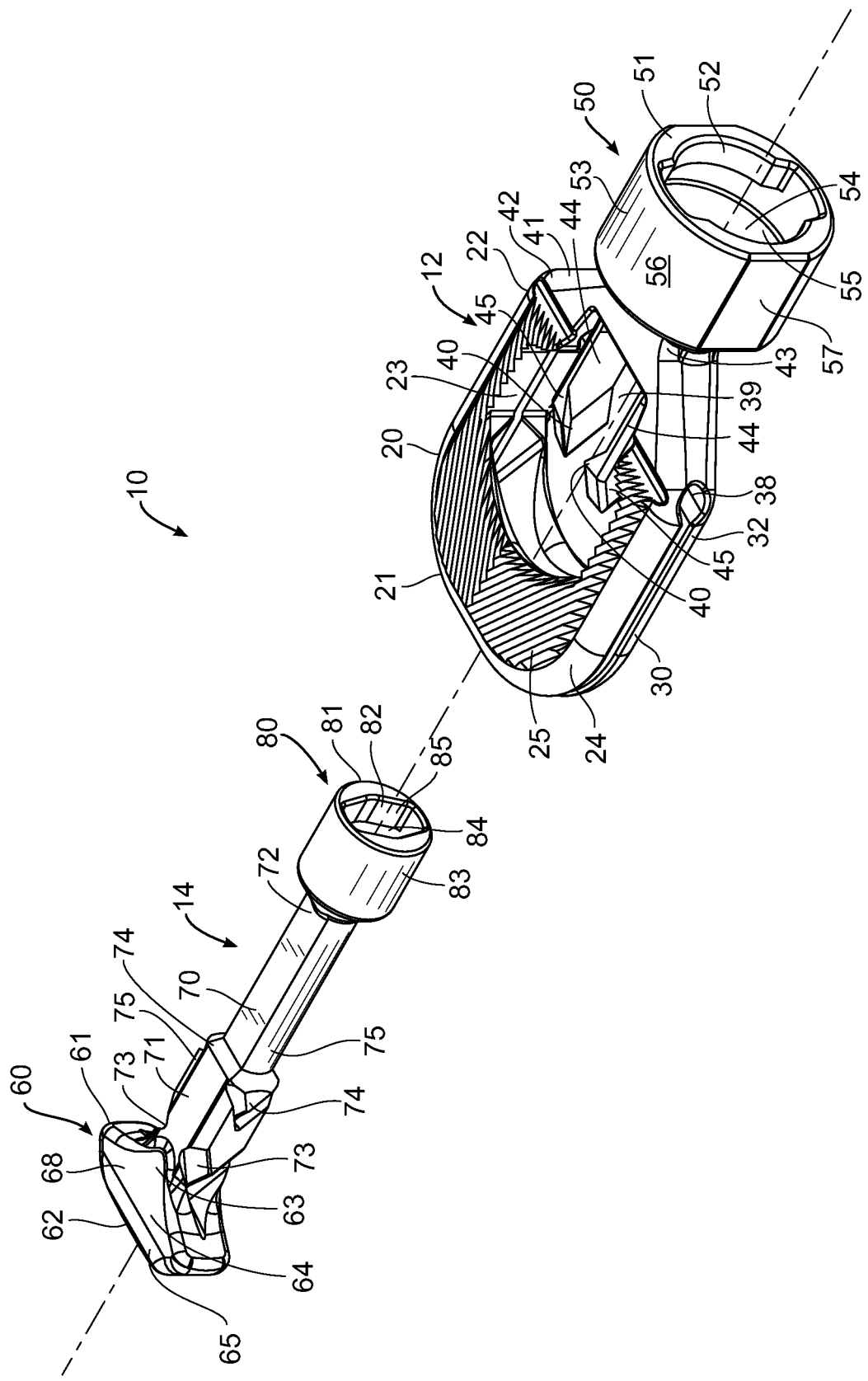
FIG. 9A is an exploded first perspective view of a distally expanding facet joint implant in a closed state showing a distally expanding outer part and an inner part with wedge-shaped engagement structure of the implant in accordance with an example embodiment.
Figure 9B:
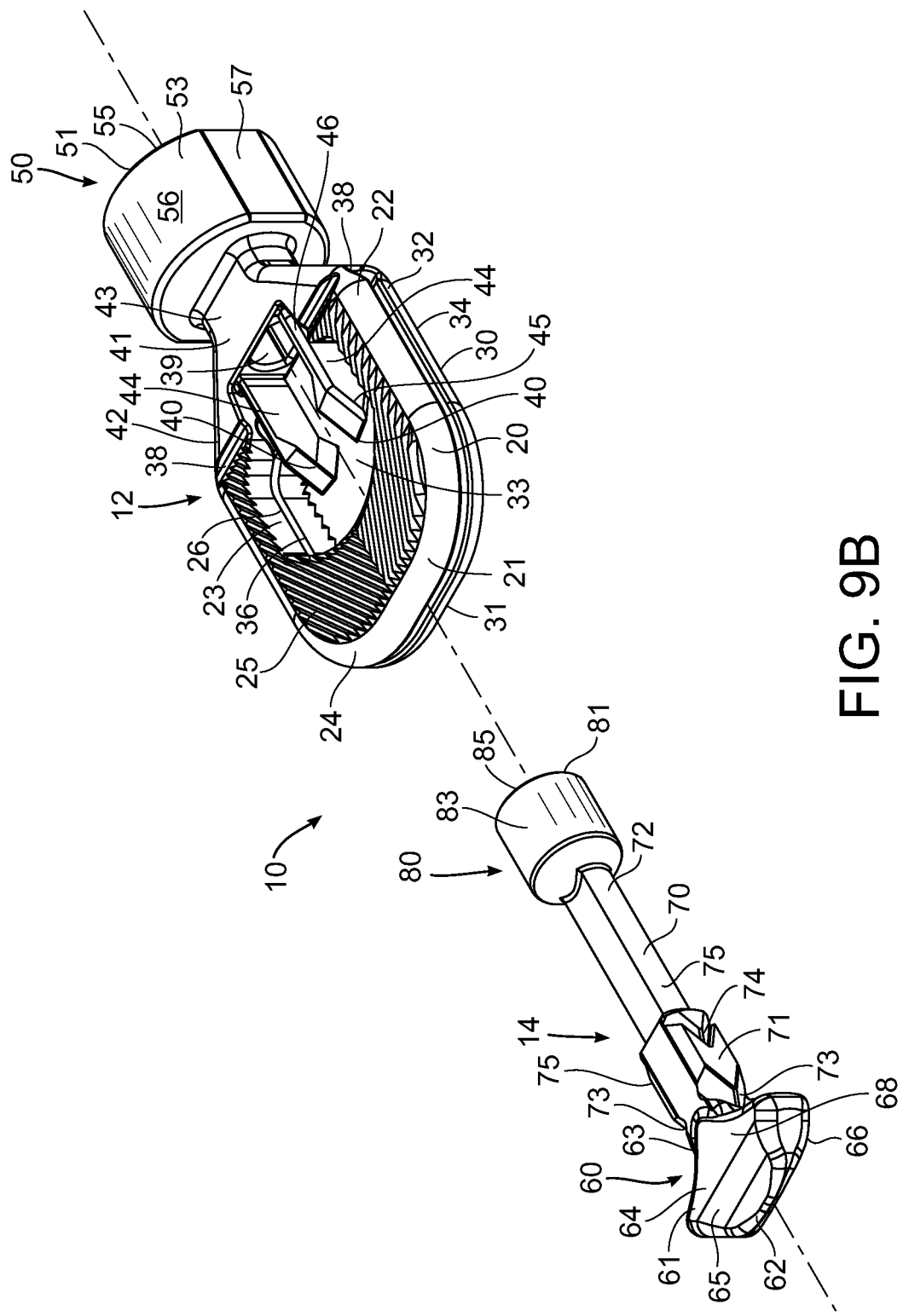
FIG. 9B is an exploded second perspective view of a distally expanding facet joint implant in a closed state showing a distally expanding outer part and an inner part with wedge-shaped engagement structure of the implant in accordance with an example embodiment.
Figure 9C:
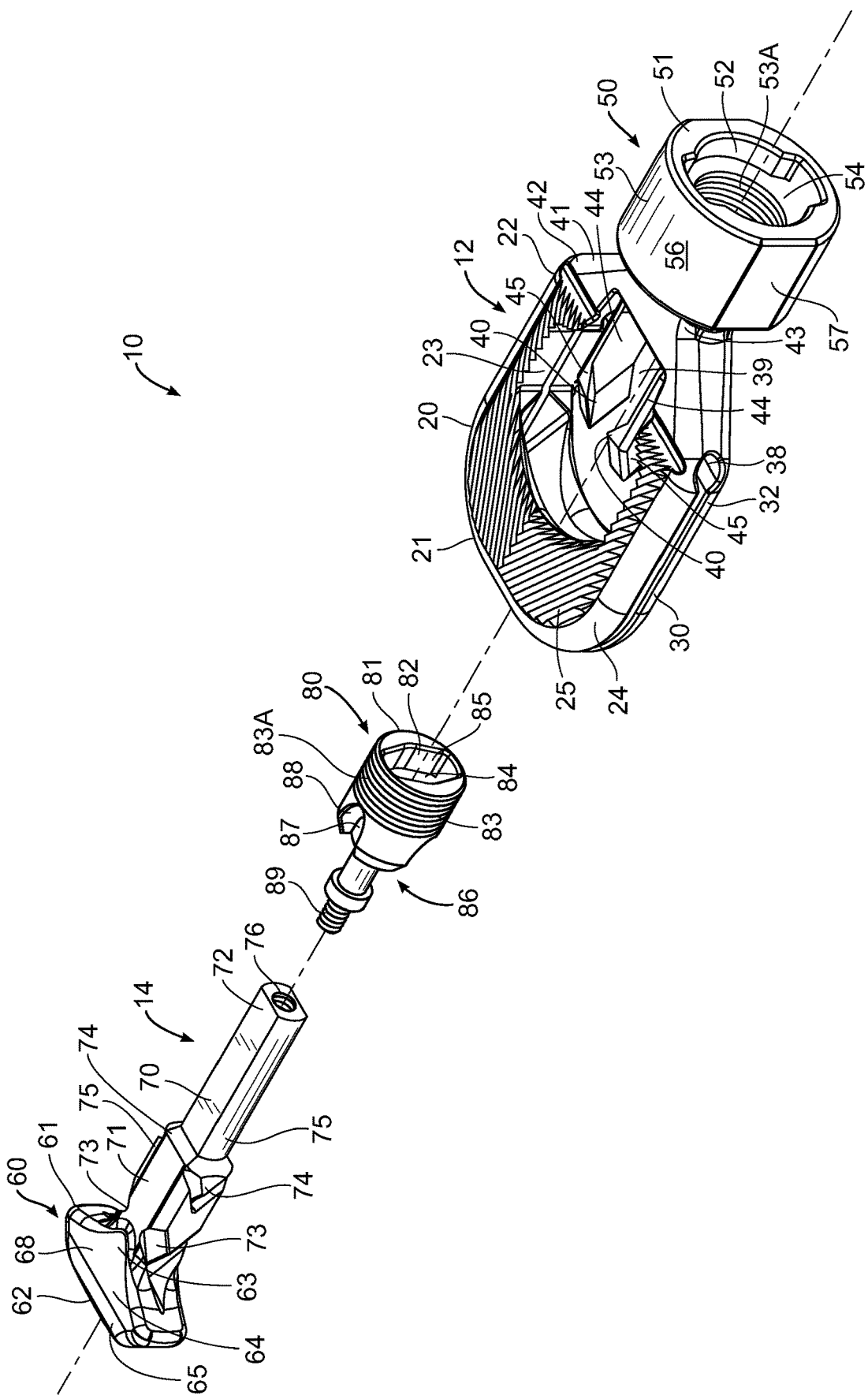
FIG. 9C is an exploded perspective view of the inner part of a distally expanding facet joint implant in accordance with an alternative example embodiment.
Figure 9E:
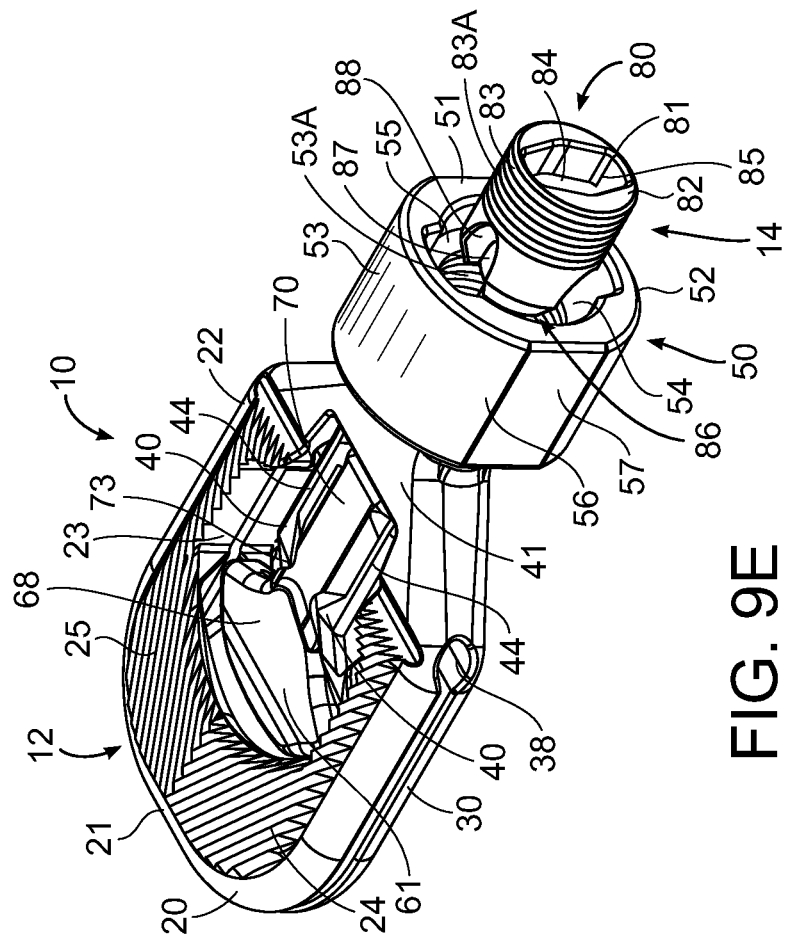
FIG. 9E is a perspective view of a second or inner connector of an inner part and a first or outer connector of an outer part of a distally expanding facet joint showing threaded engagement between the second connector and first connector in accordance with an alternative example embodiment.
Figure 9D:
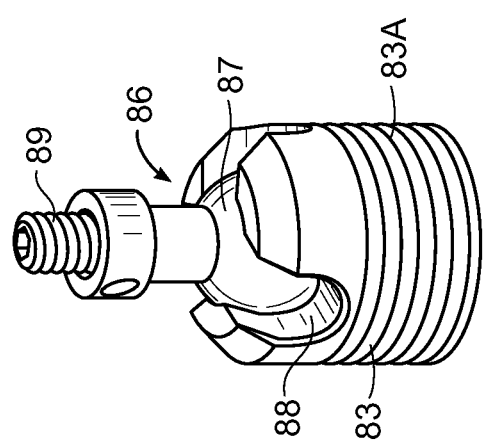
FIG. 9D is a perspective view of a second or inner connector of the inner part of a distally expanding facet joint implant in accordance with an alternative example embodiment.
Figure 10:
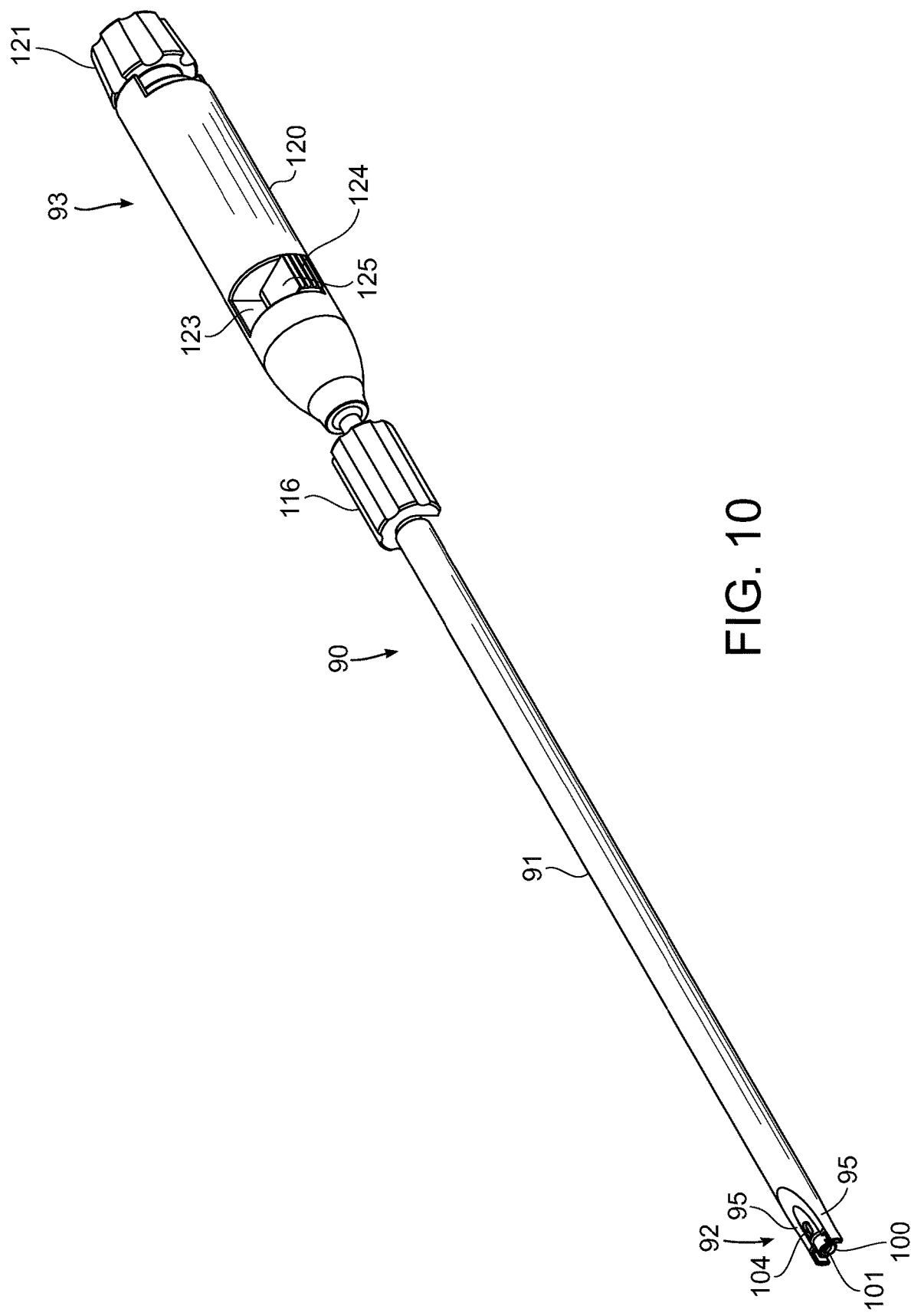
FIG. 10 is a perspective view of a delivery device for use with a distally expanding facet joint implant in accordance with an example embodiment.
Figure 20:
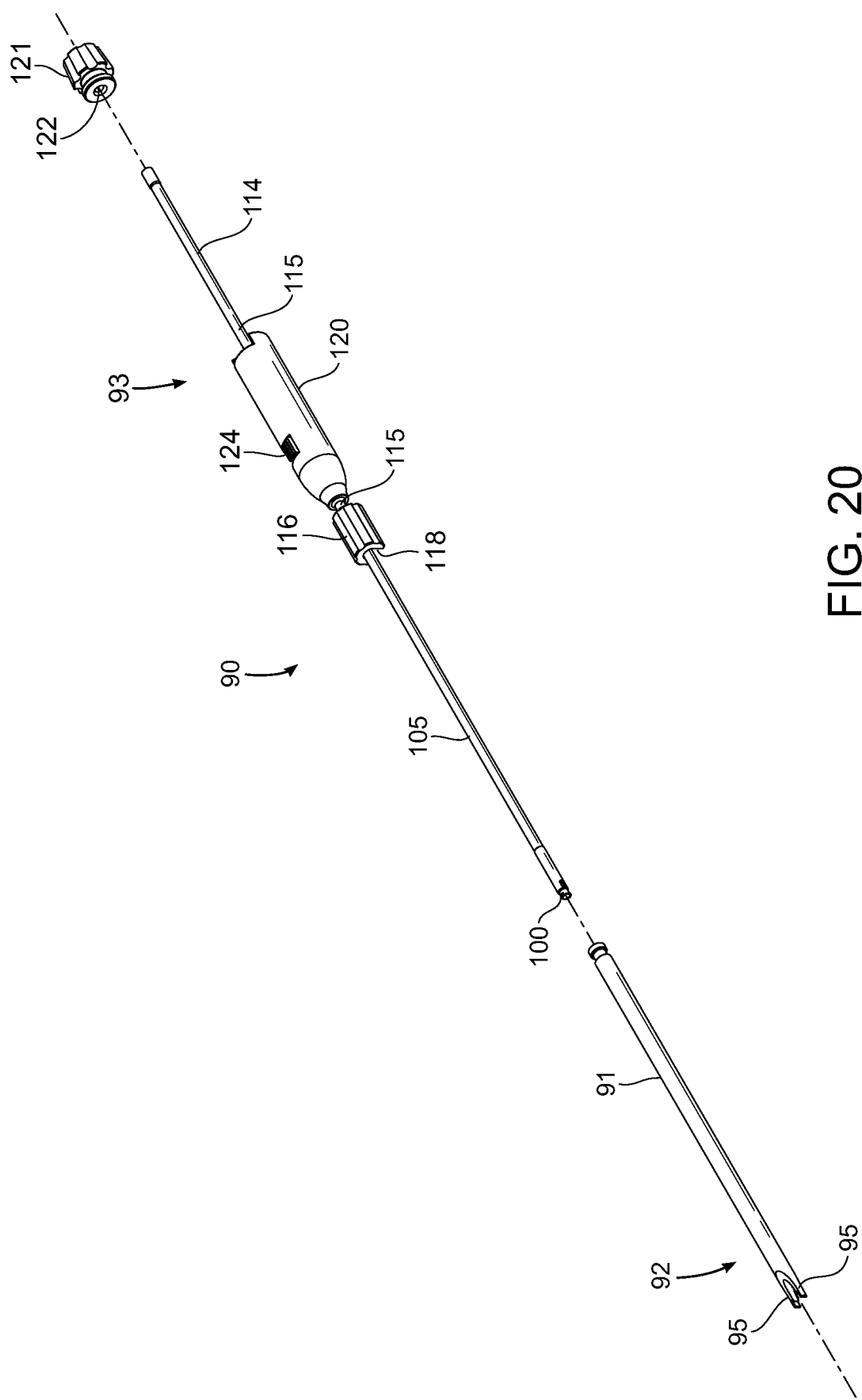
FIG. 20 is an exploded perspective view of a delivery device for use with a distally expanding facet joint implant showing the components of the delivery device in accordance with an example embodiment.

In an alternative example embodiment illustrated in FIGS. 9C-9E, the second delivery device interface 80, more specifically the second or inner connector 81, and even more specifically the second bayonet connector 82 is formed as a separate structure from the remaining components of the inner part 14 of the facet joint implant 10. In the alternative embodiment, the second delivery device interface 80, more specifically the second or inner connector 81, and even more specifically the second bayonet connector 82 is connected to the elongated connector 70 of the inner part 14 by a ball-socket connector 86.

As described further below, the ball-socket connector 86 enables the second bayonet connector 82 to be rotated relative to and without rotating the elongated connector 70 or the wedge 61 of the inner part 14 of the facet joint implant 10 and to cause the inner part 14 to translate in distal and proximal directions relative to the outer part 12 of the facet joint implant 10 without rotating. The ball-socket connector 86 can also be replaced by a disc-in-socket connector or any other connector that permits the second connector 81 to be rotated at the proximal end portion of the facet joint implant 10 and to cause the inner part 14 to be pushed in the direction of the distal end portion of the facet joint implant 10 or to be pulled in the direction of the proximal end portion relative to the outer part 12 without rotating the other components of the inner part 14 nearer the distal end portion of the facet joint implant 10.

The ball-socket connector 86 comprises a ball 87. The ball 87 is seated in a socket 88 formed in the body 83 of the second connector 81. The socket 88 and hence the body 83 of the second connector 81 is able to rotate on and relative to the ball 87.

The ball-socket connector 86 and hence the second connector 81 is preferably rigidly but removably coupled to the elongated connector 70 of the inner part 14 of the facet joint implant 10. This coupling may be accomplished in many suitable ways. In one preferred way, the ball-socket connector 86 comprises a threaded shaft 89 having outside threads. The threaded shaft 89 is fixedly connected or attached to the ball 87 and extends outwardly from the socket 88.

The proximal end 72 of the elongated connector 70 of the inner part 14 of the facet joint implant 10 comprises a threaded passage 76 having inner threads. The threaded shaft 89 of the ball-socket connector 86 extends within the threaded passage 76 of the elongated connector 70 with the outer threads of the threaded shaft 89 in threaded engagement with the inner threads of the threaded passage 76. With the ball-socket 86 coupled to the elongated connector 70, the socket 88 and hence the second connector 81 is free to rotate on the ball 87 relative to the elongated connector 70. The second connector 81 is also free to rotate relative to the first or outer connector 51 of the outer part 12 of the facet joint implant.

The body 83 of the second or inner connector 81 is provided with a set of outer threads 83A. The body 53 of the first or outer connector 51 is provided with a corresponding set of inner threads 53A. The body 83 of the second or inner connector 81 and the body 53 of the first or outer connector 51 are dimensioned and configured so that when the second or inner connector 81 is positioned within the first or outer connector 51, for example as illustrated in FIG. 1B, the outer threads 83A on the body 83 of the second or inner connector 81 engage with the inner threads 53A on the body 53 of the first or outer connector 51.

When the first connector 51 is in locked engagement with the corresponding first connector 100 of the delivery device 90 as described herein, the outer part 12 of the facet joint implant 10 is held in position by the delivery device 90 and the inner part 14 of the facet joint implant 10 is free to move relative to the outer part 12. Accordingly, rotation of the second connector 81 within the first connector 51 causes the second connector 81 to translate within the first connector 51 on the inner and outer threads 53A, 83A. This in turn causes the inner part 14, including the wedge 61, to advance distally or retract proximally relative to the outer part 12, including the first facet plate 20 and the second facet plate 30, depending on which direction the second connector 81 is rotated. In turn, this causes the facet joint implant 10 to distally expand or to distally contract in the manner described herein, again depending on the direction the second connector 81 is rotated.

As an additional alternative, the entire inner part 14 could simply be replaced by a threaded screw with outer threads, and the entire outer part 12 could simply be replaced by a structure with a thicker distal end than proximal end and a passage with inner threads. In this alternative, the threaded screw would extend into the passage with the outer threads of the screw engaged with the inner threads of the passage. Rotation of the screw relative to passage would cause the thicker distal end of the structure to translate distally creating a wedge-like expansion of the facet joint implant.

D. Delivery Device

Illustrated primarily in FIGS. 10 through 26D, the delivery device 90 for use with the distally expanding facet joint implant 10 is an elongated device with a distal end portion 92 and a proximal end portion 93. The delivery device 90 generally comprises a hollow outer tube 91 that extends between the distal end portion 92 and the proximal end portion 93. The delivery device 90 also comprises a hollow inner tube 105 that extends between the distal end portion 92 and the proximal end portion 93 and that has a corresponding first or outer connector 100 at the distal end portion 92. The corresponding first or outer connector 100 is configured to be brought into engagement and into locked engagement with the first or outer connector 51 of the first delivery device interface 50 of the facet joint implant 10. The delivery device 90 also comprises an inner shaft 115 that extends between the distal end portion 92 and the proximal end portion 93 and that has a corresponding second or inner connector 110 at the distal end portion 92. The corresponding second or inner connector 110 is configured to be brought into engagement and into locked engagement with the second or inner connector 81 of the second delivery device interface 80 of the facet joint implant 10.

The delivery device 90 also comprises an outer tube control knob 116 that is located at the proximal end portion 93 and that is coupled with the outer tube 91 and with the inner tube 105. The delivery device 90 also comprises a control handle 120 that is located at the proximal end portion 93 and that is coupled with the corresponding first connector 100 via the inner tube 105. The delivery device 90 further comprises an inner shaft control knob 121 that is located at the proximal end portion 93 and that is coupled with the corresponding second connector 110 of the delivery device 90 via the inner shaft 115. The delivery device 90 further comprises a lock switch 124 and lock 162 that are located at the proximal end portion 93 and that are coupled with the corresponding second connector 110 of the delivery device 90 via the inner shaft 115.

The delivery device 90 is used to introduce the facet joint implant 10 into the body of a patient posteriorly through a posterior incision and to deliver the facet joint implant 10 through a preferably dilated passageway to a facet joint 140 in which the facet joint implant 10 is to be implanted. Once the facet joint implant 10 is at the facet joint 140, the delivery device 90 is used to position and orient the facet joint implant 10 relative to a posterior opening 141 of the facet joint 140 as desired, and then to insert the facet joint implant 10 into the facet joint 140, position the facet joint implant 10 in the facet joint 140 as desired, and deploy the facet joint implant 10 by causing it to distally expand to its open position to distally distract the facet joint 140. The delivery device 90 may also be used to cause the facet joint implant 10 to distally contract to its closed position for repositioning within the facet joint 140 or even removal from the facet joint 140.

1. Corresponding First (Outer) Connector.

The corresponding first or outer connector 100 is located at the distal end of the hollow inner tube 105 at the distal end portion 92 of the delivery device 90. The corresponding first or outer connector 100 is configured to selectively be brought into engagement with the first or outer connector 51 of the first delivery device interface 50 of the facet joint implant 10 and to selectively be inserted into the first or outer connector 51. The corresponding first or outer connector 100 is also configured to selectively be brought into locked engagement with the first or outer connector 51 to hold the facet joint implant 10 in a fixed position and orientation relative to the delivery device 90. This enables the delivery device 90 to be manipulated to insert the facet joint implant 10 into the body of a patient, deliver it to a facet joint 140 in which it is to be implanted, insert it in the facet joint 140, and position it within the facet joint 140.

The hollow inner tube 105 and the corresponding first connector 100 are at least partially contained within the hollow outer tube 91 and are movable relative to the hollow outer tube 91 for the corresponding first connector 100 to be selectively brought into engagement with and inserted into the first connector 51 of the first delivery device interface 50 of the facet joint implant 10, and for the corresponding first connector 100 to be selectively brought into locked engagement with the first connector 51. More specifically, the hollow inner tube 105 and the corresponding first connector 100 are at least rotationally movable within and relative to the hollow outer tube 91. At least a portion of the corresponding first connector 100 extends beyond the distal end portion 92 of the hollow outer tube 91 and is exposed outside of the hollow outer tube 91 for being brought into engagement, being inserted in, and being brought into locked engagement with the first connector 51 of the first delivery device interface 50 of the facet joint implant 10. In the example embodiments, the corresponding first or outer connector 100 of the delivery device 90 and the first or outer connector 51 of the facet joint implant 10 are brought into engagement by manipulating the delivery device 90 to bring the corresponding first connector 100 into contact with the first connector 51 in the proper alignment. When the corresponding first connector 100 is in proper alignment with the first connector, the delivery device 90 is manipulated to insert the corresponding first connector 100 at least partially in the first connector 51. Once the corresponding first connector 100 is inserted in the first connector 51, the corresponding first connector 100 is brought into locked engagement with the first connector 51 by rotating the corresponding first connector 100 within the first connector 51, for example by approximately 90 degrees. This is accomplished in a manner described further below.

Although the corresponding first connector 100 can take many suitable forms, in the example embodiments where the first or outer connector 51 of the facet joint implant 10 comprises a first bayonet connector 52, the corresponding first connector 100 of the delivery device 90 comprises a first bayonet 101. Preferably, the first bayonet 101 has a substantially cylindrical shape and is configured and dimensioned to be at least partially insertable into the interior space 54 of the body 53 of the first bayonet connector 52 through the open face 55. Preferably, the first bayonet 101 is configured and dimensioned so that rotating it relative to the body 53 of the first bayonet connector 52 by 90 degrees, for example, locks it in engagement with first bayonet connector 52.

The hollow outer tube 91 of the delivery device 90 is provided with a first key 94 to ensure the corresponding first or outer connector 100 of the delivery device 90 can only be brought into engagement with and inserted in the first or outer connector 51 of the outer part 12 of the facet joint implant 10 in proper alignment. The first key 94 also prevents the facet joint implant 10 from inadvertently rotating relative to the delivery device 90 when it is connected to the delivery device 90.

The first key 94 comprises a set of holding arms 95. The holding arms 95 extend outwardly from the distal end portion 92 of the hollow outer tube 91 of the delivery device 90 around the exterior of the corresponding first connector 100. In the example embodiments, two holding arms 95 extend from the distal end portion 92 of the hollow outer tube 91 on opposite sides of the corresponding first connector 100. Each holding arm 95 has a flat portion 96 that faces the corresponding first connector 100.

The holding arms 95 and flat portions 96 are configured so that the corresponding first connector 100 of the delivery device 90 can only be brought into engagement with and inserted into the first connector 51 of the facet joint implant 10 when the flat portions 96 on the holding arms 95 are aligned with the flats 57 on the exterior surface 56 of the body 53 of the first connector 51. When the flat portions 96 on the holding arms 95 are aligned with the flats 57 on the exterior surface 56 of the body 53 of the first connector 51 and it is attempted to insert the corresponding first connector 100 in the first connector 51, the flat portions 96 of the holding arms 95 pass outside of and over the flats 109 on the exterior surface 56 of the body 53 of the first connector 51 permitting the corresponding first connector 100 to be inserted in the first connector 51. If the flat portions 96 on the holding arms 95 are not aligned with the flats 57 on the exterior surface 56 of the body 53 of the first connector 51 when it is attempted to bring the corresponding first connector 100 into engagement with first connector 51 and to insert the corresponding first connector 100 in the first connector 51, the flat portions 96 on the holding arms 95 make contact with the body 53 of the first connector 51 and the corresponding first connector 100 is blocked from being inserted.

When the corresponding first connector 100 is brought into engagement with the first connector 51 and is inserted in the first connector 51 with the proper alignment, i.e., with the flat portions 96 on the holding arms 95 aligned with the flats 57 on the exterior surface 56 of the body 53 of the first connector 51, the holding arms 95 also prevent the body 53 of the first connector 51 from rotating relative to the holding arms 95. Hence, the first connector 51 is prevented from rotating relative to the corresponding first connector 100 and the outer part 12 of the facet joint implant 10 is prevented from rotating relative to the delivery device 90.

Each of the holding arms 95 also includes a support surface 97. The support surfaces 97 are located adjacent to the flat portions 96, are substantially flat, and are approximately perpendicular to the flat portions 96. The support surfaces 97 are configured to be engaged by surfaces of the body 53 of the first connector 51 when the corresponding first connector 100 is inserted in the first connector 51, the corresponding first connector 100 and the first connector 51 are brought into locked engagement, and the flat portions 96 of the holding arms 95 are advanced over the flats 57 on the body 53 of the first connector 51. The engagement of the body 53 of the first connector 51 with the support surfaces 97 further stabilizes the connection between the facet joint implant 10 and the delivery device 90. The holding arms 95, including the flat portions 96 and support surfaces 97, are configured to be advanced and withdrawn relative to the corresponding first connector 100 and the first connector 51 using the outer tube control knob 116 of the delivery device 90 in a manner described further below.

When it is desired to connect the facet joint implant 10 to the distal end portion 92 of the delivery device 90 for introduction into the body of a patient, for example, the corresponding first or outer connector 100 of the delivery device 90, and more specifically the first bayonet 101, is aligned with the first or outer connector 51 of the facet joint implant 10, and more specifically the first bayonet connector 52. The corresponding first or outer connector 100 of the delivery device 90, and more specifically the first bayonet 101, is then brought into engagement with the first or outer connector 51, and more specifically the first bayonet connector 52, of the outer part 12 of the facet joint implant 10, and the corresponding first connector 100, and more specifically the first bayonet 101, is inserted into the first connector 51 and more specifically the first bayonet connector 52.

The corresponding first or outer connector 100 of the delivery device 90, and more specifically the first bayonet 101, is then rotated relative to the first or outer connector 51 of the outer part 12 of the facet joint implant 10, and more specifically the first bayonet connector 52, to bring the corresponding first connector 100 and the first connector 51 into locked engagement. The corresponding first connector 100 of the delivery device 90 is rotated relative to the first connector 51 of the facet joint implant 10 using the control handle 120 as described below.

The flat portions 96 on the holding arms 95 of the delivery device are aligned with the flats 57 on the body 53 of the first connector 51 by manipulating the outer tube 91 of the delivery device 90, which is described further below. The connection between the facet joint implant 10 and the delivery device 90 is further stabilized by using the outer tube control knob 116 of the delivery device 90 to advance the holding arms 95 of the delivery device 90 around the body 53 of the first connector 51 so that the body 53 of the first connector 51 is brought into engagement with the support surfaces 97 of the holding arms 95, also as described below.

With the corresponding first or outer connector 100 of the delivery device 90 and the first or outer connector 51 of the facet joint implant 10 in locked engagement, the facet joint implant 10 is securely held in a fixed position and orientation relative to the delivery device 90. The delivery device 90 can then be manipulated to introduce the facet joint implant 10 into the body of a patient and to deliver it to and insert it in the facet joint 140 in which it is to be implanted. When it is desired to disconnect the delivery device 90 from the facet joint implant 10, the process is simply reversed. The holding arms 95 of the delivery device 90 are retracted relative to the first corresponding connector 100 of the delivery device 90 and the first connector 51 of the facet joint implant 10. Then the corresponding first connector 100, and more specifically the first bayonet 101, is rotated in the opposite direction and is withdrawn from the first connector 51, and more specifically the first bayonet connector 52, of the facet joint implant 10.

In the example embodiments, the corresponding first connector 100 of the delivery device 90 is preferably substantially cylindrical in shape. In addition, the corresponding first connector 100 is preferably at least partially hollow with an interior space 102 and the corresponding second or inner connector 110 of the delivery device 90 is at least partially contained within the interior space 102 of corresponding first connector 100. The corresponding second or inner connector 110 of the delivery device 90 is described further below. In the example embodiments, the corresponding second or inner connector 110 is also substantially cylindrical in shape, and the corresponding first connector 100 and the corresponding second connector 110 are arranged to be substantially concentric. However, that arrangement is a matter of preference and is not always necessary.

The corresponding first connector 100 also has an open face 103 at the distal end portion 92 of the delivery device 90 and the open face 103 provides access to the interior space 102 within the corresponding first connector 100. The corresponding first connector 100 is configured and dimensioned so that when it is properly inserted in the first or outer connector 51 of the facet joint implant 10, the second or inner connector 81 of the facet joint implant 10 extends at least partially through the open face 103 and into the interior space 102 of the corresponding first connector 100 where it can be brought into engagement with, inserted in, and brought into locked engagement with the corresponding second connector 110 of the delivery device 90 as described below.

The inner tube 105 of the delivery device 90 has an opening comprising a window 104. The window 104 is located at the distal end portion 92 of the delivery device 90 and is spaced just proximally from the corresponding first connector 100. The window 104 is located so that when the corresponding first connector 100 is brought into engagement with and is inserted in the first connector 51 of the facet joint implant 10, the second or inner connector 82 of the facet joint implant 10 is at least partially visible through the window 104. In addition, the corresponding second connector 110 of the delivery device 90 also is at least partially visible through the window 104 when it is brought into engagement with the second connector 81. This facilitates checking the orientation of the corresponding second connector 110 relative to the second connector 81 and if necessary adjusting the alignment so that the corresponding second connector 110 can be brought into engagement with, inserted into, and brought into locked engagement with the second connector 81 as described further below.

The corresponding first connector 100 is formed or connected at the distal end of the inner tube 105. The inner tube 105 extends within the hollow outer tube 91 from the distal end portion 92 of the delivery device 90 to the proximal end portion 93 of the delivery device 90. The inner tube 105 is moveable within and relative to the hollow outer tube 91, and more specifically is rotationally moveable within and relative to the hollow outer tube 91.

In the example embodiments, the inner tube 105 is substantially cylindrical shaped and is at least partially hollow. The corresponding second connector 110 of the delivery device is formed or connected to the distal end of the inner shaft 115, which extends within the hollow outer tube 91, and more specifically within the hollow inner tube 105 within the hollow outer tube 91, from the corresponding second connector 110 at the distal end portion 92 of the delivery device 90 to the proximal end portion 93 of the delivery device 90. Preferably but not necessarily, the hollow inner tube 105 and the inner shaft 115 are arranged to be substantially concentric. The corresponding second connector 110 and the inner shaft 115 are described further below.

At the proximal end portion 93 of the delivery device 90, the outer tube 91 is fixedly connected or attached to the outer tube control knob 116, which is in turn rotatably connected to the inner tube 105 in a manner described further below. The inner tube 105 also is fixedly connected or attached to the control handle 120 of the delivery device 90. The outer tube 91 is configured and adapted to be controlled by the outer tube control knob 116. More specifically, movement of the outer tube 91 to advance and withdraw relative to the inner tube 105 and the corresponding first connector 100 is controllable via manipulation of the outer tube control knob 116. The inner tube 105 and the corresponding first connector 100 are configured and adapted to be controlled by the control handle 120. More specifically, the movement of the inner tube 105 and the movement of the corresponding first connector 100 are controllable via manipulation of the control handle 120. The operation of the outer tube control knob 116 and the control handle 120 are described further below.

It is preferred that the corresponding first connector 100 and the inner tube 105 comprise a single monolithic structure. However, the inner tube 105 can comprise a separate structure from the corresponding first connector 100. In that case, the corresponding first connector 100 is preferably fixedly connected or attached to the inner tube 105 at the distal end of the delivery device 90 so that the inner tube 105 and the corresponding first connector 100 move together, e.g., when the inner tube 105 is rotated within the hollow outer tube 91, the corresponding first connector 100 rotates the same.

2. Corresponding Second (Inner) Connector.

The corresponding second or inner connector 110 is located at the distal end of the inner shaft 115 at the distal end portion 92 of the delivery device 90. The corresponding second connector 110 is configured and operable to selectively be brought into engagement with the second or inner connector 81 of the first delivery interface 80 of the facet joint implant 10 and to be selectively inserted into the second or inner connector 81. The corresponding second connector 100 also is configured and operable to selectively be brought into locked engagement with the second or inner connector 81. The corresponding second connector 110 also is configured and operable to impart motion to the inner part 14 of the facet joint implant 10 relative to the outer part 12 of the facet joint implant 10. The delivery device 90 is thus able to be manipulated to cause the facet joint implant 10 to distally expand to its open position in a facet joint 140 in which it is implanted so as to distally distract the facet joint 140, and to cause the facet joint implant 10 to distally retract in order to reposition or remove the facet joint implant 10 from the facet joint 140.

More specifically, the inner shaft 115 and the corresponding second connector 110 are at least partially contained within the hollow outer tube 91 and are movable relative to the hollow outer tube 91 to selectively be brought into engagement with, inserted into, and brought into locked engagement with the second connector 81 to impart motion to the wedge 61 of the inner part 14 of the facet joint implant 10 relative to the first facet plate 20 and the second facet plate 30 of the outer part 12 of the facet joint implant 10. Still more specifically, the inner shaft 115 and the corresponding second connector 110 are selectively moveable at least in the direction of the distal end portion 92 and the proximal end portion 93 of the delivery device 90, rotationally within and relative to the hollow outer tube 91, and relative to the corresponding first connector 100. Even more specifically, the inner shaft 115 and the corresponding second connector 110 are at least partially contained within the hollow inner tube 105 within the hollow outer tube 91 of the delivery device 90, and are selectively movable at least in the direction of the distal end portion 92 and the proximal end portion 93 of the delivery device 90 and rotationally within and relative to the hollow inner tube 105 within the hollow outer tube 91, and relative to the corresponding first connector 100.

As mentioned previously, in the example embodiments the inner shaft 115 and the corresponding second connector 110 are substantially cylindrical in shape and are at least partially contained within the substantially cylindrical shaped and at least partially hollow inner tube 105. In addition, the hollow inner tube 105 and the corresponding first connector 100, and the inner shaft 115 and the corresponding second connector 110 preferably are arranged to be substantially concentric. However, this arrangement is a matter of preference and not necessity.

In the example embodiments, the corresponding second or inner connector 110 of the delivery device 90 and the second or inner connector 81 of the facet joint implant 10 are brought into engagement by manipulating the delivery device 90 to bring the corresponding second connector 110 into contact with the second connector 81 with the proper alignment. When the corresponding second connector 110 is in proper alignment with the second connector 81, the delivery device 90 is manipulated to insert the corresponding second connector 110 at least partially in the second connector 81. Once the corresponding second connector 110 is inserted in the second connector 81, the corresponding second connector 110 is brought into locked engagement with the second connector 81 by rotating the corresponding second connector 110 within and relative to the second connector 82, for example by approximately 90 degrees.

Although the corresponding second connector 110 can take many suitable forms, in the example embodiments where the second or inner connector 81 of the inner part 14 of the facet joint implant 10 comprises a second bayonet connector 82, the corresponding second connector 110 of the delivery device 90 comprises a second bayonet 111. The second bayonet 111 is adapted and configured to be brought into engagement with and to be inserted in the second bayonet connector 82. The second bayonet 111 is inserted into the second bayonet connector 82 by inserting the bayonet into the open interior space 84 in the body 83 of the second bayonet connector 82 through the open face 85 of the second bayonet connector 82. The second bayonet 111 is adapted and configured to be brought into locked engagement with the second bayonet connector 82 by rotating the second bayonet 111 relative to the second bayonet connector 82, for example by approximately 90 degrees.

In the example embodiments, the corresponding second connector 110 of the delivery device 90 comprises a second key 113. The second key 113 is configured and operable to allow the corresponding second connector 110 to be inserted in and withdrawn from the second connector 81 only when the corresponding second connector 110 and the second connector 81 are in a particular alignment, and not otherwise. In the example embodiments where the corresponding second connector 110 comprises the second bayonet 111, the second bayonet comprises a t-shaped pin 112 as the second key 113. The t-shaped pin 112 is configured to correspond to the shape of the open face 85 of the second bayonet connector 82 of the second or inner connector 81 of the facet joint implant 10. That shape can be, for example, a vertical slot shape. Accordingly, the t-shaped pin 112 allows the second bayonet 111 to be inserted into and withdrawn from the open interior space 84 in the body 83 of the second bayonet connector 82 only when the t-shaped pin 112 is aligned in a particular orientation relative to the shape of the open face 85, e.g., the vertical slot, and otherwise blocks the second bayonet 111 from being inserted or withdrawn. Accordingly, once the t-shaped pin 112 of the second bayonet 111 is inserted into the second bayonet connector 82 and rotated to bring the corresponding second connector 110 into locked engagement with the second connector 81, the t-shaped pin 112 prevents the corresponding second connector 110 from inadvertently being withdrawn from the second connector 81.

It will be appreciated that while in the example embodiments, the second key 113 comprises a t-shaped pin 112 of a second bayonet 111, the second key may take many other forms consistent suitable to achieve the objective described. It will also be appreciated that the t-shaped pin 112 and the corresponding shape of the open face 85 of the second bayonet connector 82 may have many variations suitable to achieve the objective described. For example, other letter shapes, e.g. "H," and other geometric shapes, e.g., a star shape, may be used.

To facilitate the proper alignment of the corresponding second connector 110 of the delivery device 90 and the second connector 81 of the inner part 14 of the facet joint implant 10, and as mentioned previously, the inner tube 105 of the delivery device 90 has an opening comprising a window 104. The window 104 is located at the distal end portion 92 of the delivery device 90 and is spaced just proximally from the corresponding first connector 100 of the delivery device 90. With the corresponding first connector 100 of the delivery device 90 in engagement with and inserted in the first connector 51 of the outer part 12 of the facet joint implant 10, the corresponding second connector 110 of the delivery device 90 and the second connector 81 of the inner part 14 of the facet joint implant 10 are at least partially visible through the window 104 as the corresponding second connector 110 is brought into engagement with and inserted into the second connector 81. The window 104 thus provides for the orientation of the corresponding second connector 110 relative to the second connector 81 to be checked visually and, if necessary, to be adjusted so that the corresponding second connector 110 can be brought into engagement with, inserted into, and brought into locked engagement with the second connector 81 as described above.

When the corresponding second connector 110 of the delivery device 90 is in engagement with and inserted in the second connector 81 of the inner part 14 of the facet joint implant 10, the delivery device 90 can be manipulated as further described below to selectively impart motion to the inner part 14 of the facet joint implant 10, including the wedge 61, to move distally relative to the outer part 12 of the facet joint implant 10, including the first facet plate 20 and the second facet plate 30. Thus, the delivery device 90 can be manipulated to selectively cause the facet joint implant 10 to distally expand from its closed state to its open state in the manner described herein. It will be appreciated that because the wedge 61 is pushed in a distal direction, rather than pulled in a proximal direction, to cause the facet joint implant 10 to distally expand to the open state, it is only necessary for the corresponding second connector 110 to be in engagement with and inserted in the second connector 81 of the facet joint implant 10 to achieve this effect. It is not necessary that the corresponding second connector 110 be in locked engagement with the second connector 81. Nevertheless, it is preferred for the corresponding second connector 110 and the second connector 81 to be in locked engagement to avoid potential inadvertent disengagement during a procedure. In addition, if it is desired to pull the wedge 61 in the proximal direction to cause the facet joint implant 10 to distally retract to the closed state, for example for removal or repositioning, the corresponding second connector 110 and the second connector 81 must be in locked engagement.

When it is desired to unlock and disengage the delivery device 90 from the inner part 14 of the facet joint implant 10, the process described above is simply reversed. The corresponding second connector 110 of the delivery device 90, and more specifically the second bayonet 111, is rotated in the opposite direction and then withdrawn from the second connector 81 of the facet joint implant 10, and more specifically the second bayonet connector 82.

As mentioned previously, the corresponding second connector 110 is fixedly connected or attached to the distal end of the inner shaft 115, which extends within the hollow outer tube 91, and more specifically within the hollow inner tube 105 within the hollow outer tube 91, from the corresponding second connector 110 at the distal end portion 92 of the delivery device 90 to the proximal end portion 93 of the delivery device 90. Preferably but not necessarily, the inner tube 105 and the inner shaft 115 are arranged to be substantially concentric.

The inner shaft 115 is selectively moveable within and relative to the hollow outer tube 91. More specifically, the inner shaft 115 is selectively movable at least in the direction of the distal end portion 92 and the proximal end portion 93 of the delivery device 90 and rotationally within and relative to the hollow outer tube 91. Still more specifically, the inner shaft 115 is selectively moveable within and relative to the hollow inner tube 105 within the hollow outer tube 91. Still more specifically the inner shaft 115 is selectively movable at least in the direction of the distal end portion 92 and the proximal end portion 93 of the delivery device 90 and rotationally within and relative to the hollow inner tube 105 within the hollow outer tube 91.

At the proximal end portion 93 of the delivery device 90, the inner shaft 115 is movably connected or attached to the inner shaft control knob 121 and to a lock switch 124 and a lock 162. The inner shaft 115 and the corresponding second connector 110 are configured and adapted to be controlled by the inner shaft control knob 121 and the lock switch 124. More specifically, the movement of the inner shaft 115 and the corresponding second connector 110 are controllable via manipulation of the inner shaft control knob 121 and the lock switch 124. Still more specifically, the movement of the inner shaft 115 and the corresponding second connector 110 in the directions of the distal end portion 92 and the proximal end portion 93 of the delivery device 90 and relative to the outer tube 91, inner tube 105, and corresponding first connector 100 are controllable via manipulation of the inner shaft control knob 121. The movement of the inner shaft 115 and the corresponding second connector 110 rotationally within and relative to the hollow outer tube 91, the hollow inner tube 105, and the corresponding first connector 100 is controllable via manipulation of the lock switch 124. The inner shaft control knob 121 and the lock switch 124 are described further below.

It is preferred that the corresponding second connector 110 and the inner shaft 115 comprise a single monolithic structure. However, the inner shaft 115 can comprise a separate structure from the corresponding second connector 110. In that case, the corresponding second connector 110 is preferably fixedly connected or attached to the inner shaft 115 at the distal end of the delivery device 90 so that the inner shaft 115 and the corresponding second connector 110 move together, e.g., when the inner shaft 115 is rotated within and relative to the hollow inner tube 105 within the hollow outer tube 91, the corresponding second connector 110 rotates the same, and when the inner shaft 115 is moved within and relative to the hollow inner tube 105 within the hollow outer tube 91 toward the distal end portion 92 or the proximal end portion 93 of the delivery device 90, the corresponding second connector 110 moves the same.

3. Outer Tube Control Knob.

The outer tube control knob 116 is located at the proximal end portion 93 of the delivery device 90. The outer tube control knob 116 is fixedly coupled with the hollow outer tube 91 via a fixed coupling 117. The outer tube control knob 116 has a passageway 118 through which the inner tube 105 extends. The outer tube control knob 116 is movably coupled to the inner tube 105 via a threaded coupling 119 within the passageway 118.

The outer tube control knob 116 is configured and is selectively operable to control the outer tube 91 and to cause it to move toward the distal end portion 92 and the proximal end portion 93 of the delivery device 90 relative to the inner tube 105 and the first corresponding connector 100. Accordingly, the outer tube control knob 116 is configured and is selectively operable to cause the holding arms 95, including the flat portions 96 and support surfaces 97, to move toward the distal end portion 92 and the proximal end portion 93 of the delivery device 90.

The outer tube control knob 116 is configured and is selectively operable to cause the outer tube 91 and the holding arms 95, including the flat portions 96, and the support surfaces 97, to move toward the distal end portion 92 of the delivery device 90 by rotating the outer tube control knob 116 in a first direction. This causes the outer tube control knob 116 to translate on the threaded coupling 119 with the inner tube 105 in the direction of the distal end portion 92 and thus causes the outer tube 91 and the holding arms 95 to move in the direction of the distal end portion 92 relative to the inner tube 105 and the first corresponding connector 100 of the delivery device 90.

Similarly, the outer tube control knob 116 is configured and is selectively operable to cause the outer tube 91 and the holding arms 95, including the flat portions 96 and the support surfaces 97, to move toward the proximal end portion 93 of the delivery device 90 by rotating the outer tube control knob 116 in a second direction opposite to the first direction. This causes the outer tube control knob 116 to translate on the threaded coupling 119 with the inner tube 105 in the direction of the proximal end portion 93 and thus causes the outer tube 91 and the holding arms 95 to move in the direction of the proximal end portion 92 relative to the inner tube 105 and the first corresponding connector 100 of the delivery device 90.

When the first corresponding connector 100 is in engagement with and inserted in the first connector 51 of the facet joint implant 10, the outer tube control knob 116 is configured and is selectively operable to be rotated in the first direction to cause the outer tube 91 to move toward the distal end portion 92 of the delivery device 90, the flat portions 96 of the holding arms 95 to advance over the flats 57 on the body 53 of the first connector 51 of the facet joint implant 10, and the support surfaces 97 of the holding arms 95 to advance toward the surfaces surrounding the open face 55 of the body 53 of the first connector 51. When the corresponding first connector 100 is brought into locked engagement with the first connector 51, the body 53 of the first connector 51 is urged into engagement with the support surfaces 97. Similarly, the outer tube control knob 116 is configured and is selectively operable to be rotated in the second direction opposite to the first direction to cause the outer tube 91 to move toward the proximal end portion 93 of the delivery device 90, the flat portions 96 of the holding arms 95 to withdraw with respect to the flats 57 on the body 53 of the first connector 51, and the support surfaces 97 of the holding arms 95 to withdraw from the body 53 of the first connector 51.

4. Control Handle.

The control handle 120 is located at the proximal end portion 93 of the delivery device 90. The control handle 120 is fixedly coupled with the hollow inner tube 105 and hence with the corresponding first or outer connector 100 of the delivery device 90. The control handle 120 is configured and selectively operable to bring the corresponding first connector 100 of the delivery device 90 into locked engagement with the first connector 51 of the first delivery device interface 50 of the outer part 12 of facet joint implant 10 in the manner described above.

The control handle 120 is fixedly connected to the inner tube 105 at the proximal end portion 93 of delivery device 90 and is configured and selectively operable to control the inner tube 105 and the corresponding first connector 100. More specifically, by manipulating the control handle 120, the movement of the inner tube 105 and the corresponding first connector 100 are controllable at least to an extent. Still more specifically, at least when the corresponding second or inner connector 110 of the delivery device 90 is not in locked engagement with the second or inner connector 81 of the facet joint implant 10, the control handle 120 can be rotated to cause the corresponding first connector 100 to rotate relative to the hollow outer tube 91 of the delivery device 90.

The delivery device 90 and control handle 120 can be manipulated to bring the corresponding first connector 100 of the delivery device 90 into engagement and into locked engagement with the first connector 51 of the first delivery device interface 50 of the facet joint implant 10 in the following manner. The delivery device 90 is moved distally relative to the facet joint implant 10, or vice versa, to cause the corresponding first connector 100 of the delivery device to be brought into engagement with and inserted in the first connector 51 of the facet joint implant 10 in the manner described herein. The control handle 120 is then rotated, for example by about 90 degrees to cause the corresponding first connector 100 to rotate in and relative to the first connector 51 and bring the corresponding first connector 100 into locked engagement with the first connector 51. The outer tube 91 of the delivery device 90 is manipulated to align the flat portions 96 on the holding arms 95 at the distal end portion 92 of the delivery device 90 with the flats 57 on the exterior surface 56 of the first connector 51 of the facet joint implant 10. The outer tube control knob 116 is rotated to advance the holding arms 95 over the flats 57. To unlock and disengage the corresponding first connector 100 from the first connector 51, the delivery device 90 and control handle 120 are manipulated to simply reverse the process described.

5. Inner Shaft Control Knob.

The inner shaft control knob 121 is located at the proximal end portion 93 of the delivery device 90 and is movably coupled with the control handle 120, with the inner shaft 115, and via the inner shaft 115 with the corresponding second or inner connector 110 of the delivery device 90.

More specifically, the inner shaft control knob 121 is rotatably connected to the control handle 120 at the proximal end portion 93 of the delivery device 100 and is free to rotate relative to the control handle 120 but is not free to move toward the distal end portion 92 or the proximal end portion 93 of the delivery device 90. The inner shaft control knob 121 is also movably connected to the inner shaft 115 and via the inner shaft 115 to the corresponding second connector 110 at the proximal end portion 93 of the delivery device 90. Still more specifically, in the example embodiments the inner shaft has a threaded proximal end portion 114 and the inner shaft control knob 121 has a threaded passageway 122. The threaded proximal end portion 114 of the inner shaft 115 extends through the control handle 120 and into the threaded passageway 122, which comprises a threaded coupling 122 to the inner shaft 115. The inner shaft control knob 121 is free to rotate on the inner shaft 115 via the threaded coupling.

The inner shaft control knob 121 is configured and is selectively operable to control the inner shaft 115 and the corresponding second connector 110. More specifically, the inner shaft control knob 121 is configured and is selectively operable to control the movement of the inner shaft 115 and the corresponding second connector 110 in the directions of the distal end portion 92 and the proximal end portion 93 of the delivery device 90. Even more specifically, the inner shaft control knob 121 is selectively rotatable relative to the inner shaft 115 and is selectively operable by being rotated to cause the inner shaft 115 and the corresponding second connector 110 to move toward the distal end portion 92 and the proximal end portion 93 of the delivery device 90 relative to the control handle 120, the hollow outer tube 91, and the inner tube 105 and the corresponding first connector 100 of the delivery device 90. Rotation of the inner shaft control knob 121 on the inner shaft 115 via the threaded coupling causes the inner shaft 115 and the corresponding second or inner connector 110 of the delivery device 90 to translate in the direction of the distal end portion 92 and the proximal end portion 93 depending on the direction the inner shaft control knob 121 is rotated.

The inner shaft control knob 121 is thus configured and operable when rotated in a first direction to selectively cause the corresponding second connector 110 to move toward the distal end portion 92 of the delivery device 90 and to be brought into engagement with and inserted in the corresponding second connector 110 in the second connector 81 of the facet joint implant 10 in the manner described herein. The inner shaft control knob 121 also is configured and operable when rotated in a second direction opposite to the first direction to selectively cause the corresponding second connector 110 to move toward the proximal end portion 93 of the delivery device 90 and to be brought out of engagement with and withdraw from the second connector 81 of the facet joint implant 10 in the manner described herein.

The inner shaft control knob 121 is also configured and operable when rotated in a first direction to selectively cause the facet joint implant 10 to distally expand into its open position. Thus, the inner shaft control knob 121 is configured and operable when rotated in the first direction to selectively cause the corresponding second connector 110 of the delivery device 90 to move toward the distal end portion 92 of the delivery device 90, in turn causing the inner part 14 of the facet joint implant 10, and more specifically the wedge 61, to move distally relative to the outer part 12 of the facet joint implant 10, and more specifically the first facet plate 20 and the second facet plate 30, and the facet joint implant 10 to distally expand to its open state in the manner described previously.

Similarly, the inner shaft control knob 121 is configured and operable when rotated in a second direction opposite to the first direction to selectively cause the corresponding second connector 110 of the delivery device 90 to move toward the proximal end portion 93 of the delivery device 90, in turn causing the inner part 14 of the facet joint implant 10, and more specifically the wedge 61, to move proximally relative to the outer part 12 of the facet joint implant 10, and more specifically the first facet plate 20 and the second facet plate 30, and the facet joint implant 10 to distally contract to its closed state in the manner described previously.

As mentioned previously, because rotating the inner shaft control knob 121 in the first direction effectively pushes the corresponding second connector 110 of the delivery device 90 in the distal direction, the corresponding second connector 110 need only be in engagement with and inserted in the second connector 81 of the facet joint implant 10 while the inner shaft control knob 121 is rotated in the first direction to cause the facet joint implant 10 to distally expand to the open position. The corresponding second connector 110 need not be in locked engagement with the second connector 81. However, the corresponding second connector 110 must be in locked engagement with the second connector 81 when the inner shaft control knob 121 is rotated in the second direction in order to cause the facet joint implant 10 to distally contract to the closed position. If the corresponding second connector 110 is not in locked engagement with the second connector 81, rotation of the inner shaft control knob 121 in the second direction simply moves the corresponding second connector 110 toward the proximal end portion 93 of the delivery device 90 and brings the corresponding second connector 110 out of engagement with the second connector 81.

6. Lock Switch and Lock.

The lock switch 124 and lock 126 of the delivery device 90 are located at the proximal end portion 93 of the delivery device 90. The lock switch 124 and lock 126 are coupled with the inner shaft 115 and via the inner shaft 115 with the corresponding second connector 110 of the delivery device 90.

The lock switch 124 is configured and operable to selectively rotate the corresponding second connector 110 of the delivery device 90 relative to the second connector 81 of the facet joint implant 10 in order to bring the corresponding second connector 110 into and out of locked engagement with the second connector 81, depending on the direction the lock switch 124 is rotated. The lock 126 is responsive to the operation of the lock switch 124 and is configured and operable to hold or lock the corresponding second connector 110 in the locked engagement position to prevent the inadvertent rotation of the corresponding second connector 110 from the locked engagement position and potential unlocking and disengagement from the second connector 81.

More specifically, the lock switch 124 is configured and operable to be manipulated to rotate approximately 90 degrees between a first position and a second position relative to the control handle 120, the hollow outer tube 91, and the inner tube 105 and corresponding first connector 100 of the delivery device 90. Rotation of the lock switch 124 approximately 90 degrees between the first position and the second position also rotates the inner shaft 115 and the corresponding second connector 110 by approximately 90 degrees relative to the control handle 120, the hollow outer tube 91, and the inner tube 105 and corresponding first connector 100.

Most importantly, however, when the corresponding second connector 110 of the delivery device 90 is in engagement with and inserted in the second connector 81 of the facet joint implant 10 in the manner described above, rotation of the lock switch 124 approximately 90 degrees from the first position to the second position rotates the corresponding second connector 110 approximately 90 degrees relative to and within the second connector 81 and brings the corresponding second connector 110 into locked engagement with the second connector 81. Similarly, when the lock switch 124 is rotated from the second position to the first position, the corresponding second connector 110 rotates approximately 90 degrees relative to and within the second connector 81 and brings the corresponding second connector 110 and second connector 81 out of locked engagement. Thus, when the corresponding second connector 110 is in engagement with and inserted in the second connector 81, the first position of the lock switch 124 corresponds to an unlocked engagement position, and the second position corresponds to a locked engagement position.

In response to the lock switch 124 being rotated approximately 90 degrees from the first position (unlocked) to the second position (locked), the lock 126 is configured and operable to temporarily hold or lock the corresponding second connector 110 in the approximately 90 degree rotated second position relative to the control handle 120, the hollow outer tube 91, and the inner tube 105 and corresponding first connector 100. More importantly, when the corresponding second connector 110 of the delivery device 90 is in engagement with and inserted in the second connector 81 of the facet joint implant 10 in the manner described above, the lock 126 is configured and operable to temporarily hold or lock the corresponding second connector 110 in the approximately 90 degree rotated second (locked) position relative to the second connector 81, i.e., in the locked engagement position.

Still more specifically, in the example embodiments the lock switch 124 comprises a rotatable lever 125 that is seated and is rotatable in a slot 123 of the control handle 120. Also, as best seen in FIG. 17, and as also seen at least partially in FIGS. 22A, 23D, and 24B, the lock 126 comprises a detent mechanism 127 that is coupled to the lock switch 124, and that more specifically is coupled to the rotatable lever 125 and to the control handle 120. Even more specifically, the detent mechanism 127 comprises a spring-loaded ball plunger 128 that is connected or attached to the lock switch 124, and more specifically to the rotatable lever 125, and a ball detent 129 that is located on the control handle 120 and more specifically in the slot 123 of the control handle 120.

The slot 123 extends approximately 90 degrees around the control handle 120 with one end of the slot 123 corresponding to the first (unlocked) position of the lock switch 124 and the other end corresponding to the second (locked) position of the lock switch 124. The lock switch 124, and more specifically the rotatable lever 125, is configured and operable to be rotated approximately 90 degrees in the slot 123 between the first (unlocked) and second (locked) positions.

The inner shaft 115 passes through and is engaged by the lock switch 124, and more specifically the lever 125. The inner shaft 115 is engaged by the lock switch 124, and more specifically the lever 125, in such a way that it is free to move toward the distal end portion 92 and the proximal end portion 93 of the delivery device 90 relative to the lock switch 124, and more specifically the lever 125, but rotates with the lock switch 124, and more specifically the lever 125.

Thus, when the lock switch 124, and more specifically the lever 125, is rotated approximately 90 degrees in the slot 123 from the first (unlocked) to the second (locked position), the inner shaft 115 and the corresponding second connector 110 are rotated approximately 90 degrees as described above. More importantly, when the corresponding second connector 110 of the delivery device 90 is in engagement with and inserted in the second connector 81 of the facet joint implant 10, rotation of the lock switch 124, and more specifically the lever 125, approximately 90 degrees in the slot 123 from the first (unlocked) to the second (locked) position rotates the corresponding second connector 110 within and relative to the second connector 81 and brings corresponding second connector 110 into locked engagement with the second connector 51.

The lock 126, and more specifically the ball plunger 128 of the detent mechanism 127, rotates with the lock switch 124, and more specifically the rotatable lever 125. When the lock switch 124, and more specifically the lever 125, is rotated approximately 90 degrees in the slot 123 from the first (unlocked) to the second (locked) position, the ball of the ball plunger 128 is pushed into engagement with the ball detent 129 in the slot 123 under the pressure of the spring of the ball plunger 128. This holds or locks the lock switch 124 in the approximately 90 degree rotated second position, which holds or locks the inner shaft 115 and corresponding second connector 110 in the approximately 90 degree rotated second (locked) position relative to the control handle 120, the hollow outer tube 91, and the inner tube 105 and corresponding first connector 100 of the delivery device 90. Most importantly however, when the corresponding second connector 110 of the delivery device 90 is in engagement with and inserted in the second connector 81 of the facet joint implant 10 in the manner described above, it holds or locks the corresponding second connector 110 in the approximately 90 degree rotated second (locked) position relative to and within the second connector 81, i.e., in the locked engagement position.

In order to bring the corresponding second connector 110 out of locked engagement with the second connector 81, the process described above is simply reversed. That is, sufficient force is applied to the lever 125 of the lock switch 124 to overcome the force of the ball detent 129 mechanism and rotate the lock switch 124 in the opposite direction in the slot 123 approximately 90 degrees from the second (locked) to the first (unlocked) position. This rotates the corresponding second connector 110 approximately 90 degrees in the opposite direction and brings it out of locked engagement with the second connector 81 of the facet joint implant 10. The inner shaft control knob 121 can then be manipulated as described above to withdraw the corresponding second connector 110 from engagement with the second connector 81.

E. Operation of Preferred Embodiment

In use of the distally expanding facet joint implant 10 and delivery device 90, a facet joint 140 in which the facet joint implant 10 is to be implanted is first prepared to receive the facet joint implant 10. It is noted that while facet joint 140 and facet joint implant 10 are referred to here in the singular, such reference is for ease of discussion only and is not meant to be limiting. Persons skilled in the art will realize that each cervical vertebra includes a pair of laterally spaced facet joints. Accordingly, it is likely, although not necessarily always the case, that multiple facet joints must be prepared and multiple facet joint implants implanted in a given procedure. Thus, reference to facet joint and facet joint implant in the singular is not meant to exclude, but rather to encompass multiple facet joints, facet joint implants, and the procedures used to prepare multiple facet joints and implant multiple facet joint implants.

The manner and tools for preparing an intervertebral joint to receive an implant are well known to those skilled in the art and need not be described in detail. Briefly, various known joint preparation tools may be used to prepare an affected facet joint and these may be delivered to the joint posteriorly through a small incision using a suitable guide wire or pin. The tools may be delivered percutaneously under X-ray guidance, under direct vision, under endoscopic guidance, or through a previously inserted hollow needle, for example.

Commonly employed tools include one or more chisels for cutting the joint capsule and other tissues as necessary or desired to facilitate subsequent insertion of the facet implant in the joint. A rasp may be used to roughen the external boney surfaces of the facets facing the facet joint 140 as necessary or desired to facilitate the implant adhering to the bony surfaces. One or more dilators may be used to dilate the facet joint 140 to facilitate delivery of the facet joint implant 10 to the affected facet joint 140. Dilators of successively larger sizes in all three dimensions can be used sequentially until the necessary or desired dilation is achieved.

Figure 21:
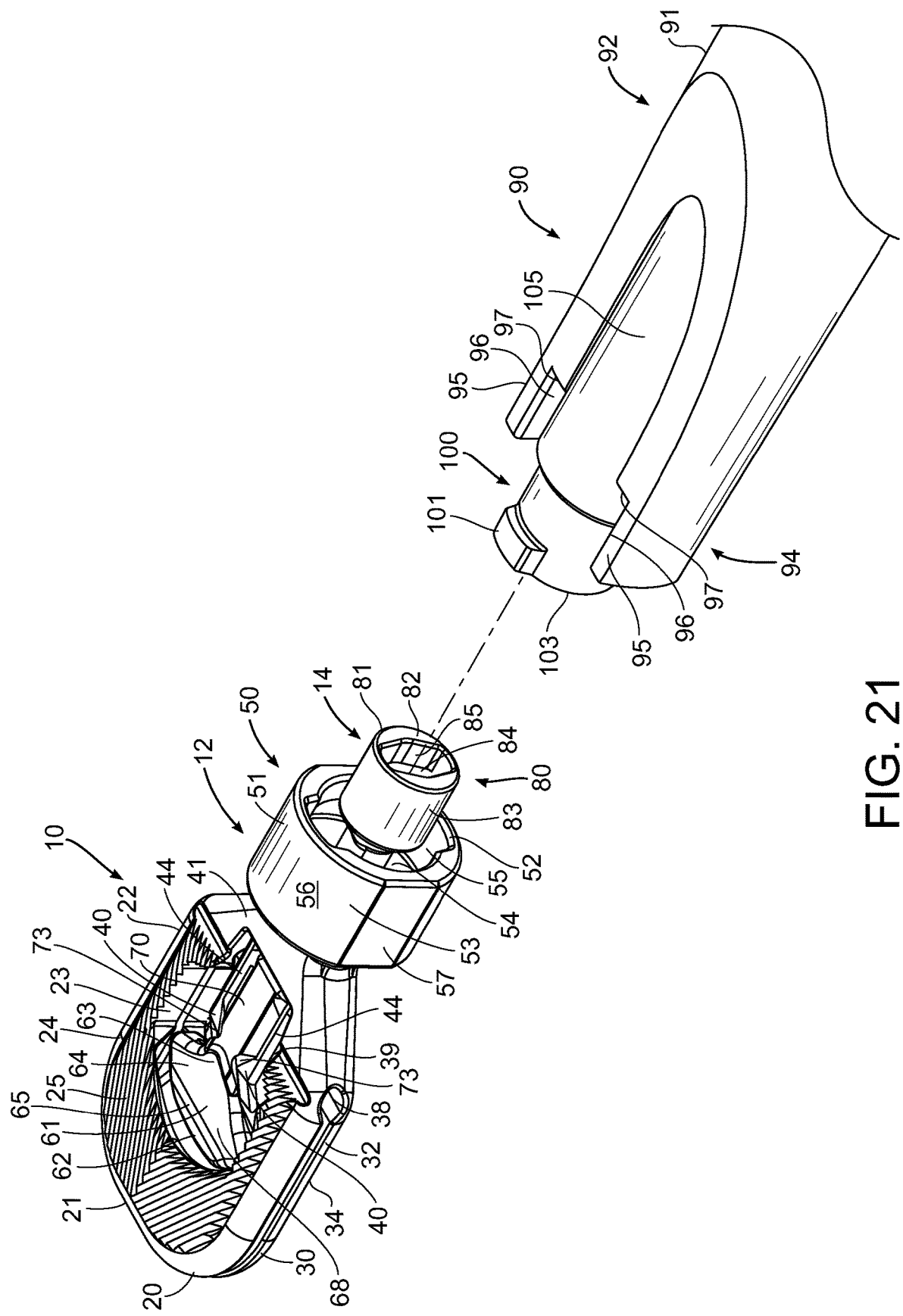
FIG. 21 is a perspective view of a distally expanding facet joint implant and the distal end of a delivery device for use with the implant showing the implant and delivery device aligned for connection in accordance with an example embodiment.
Figure 22A:
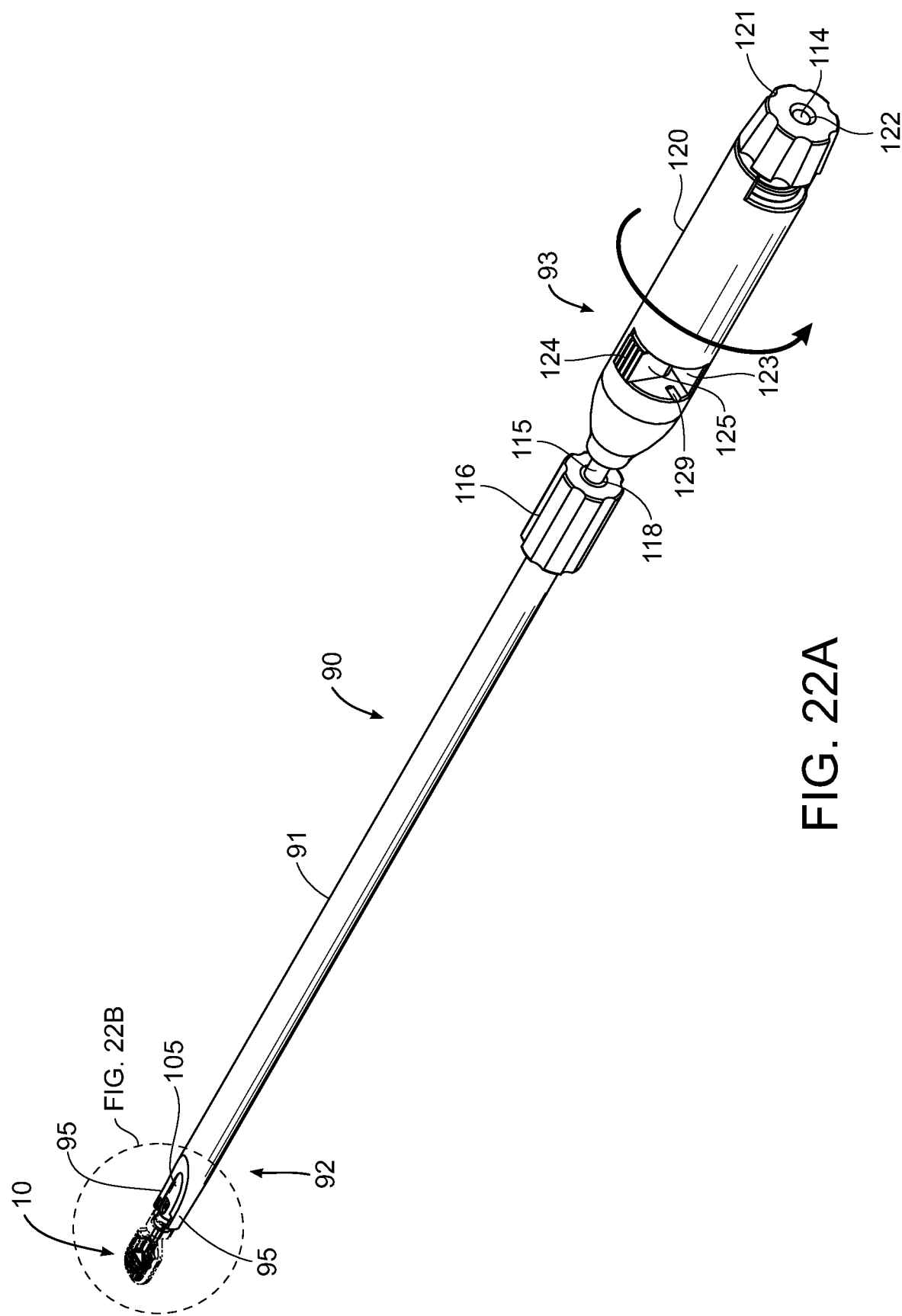
FIG. 22A is a perspective view of a distally expanding facet joint implant and a delivery device for use with the implant showing the delivery device and an outer part of the implant being brought into locked engagement in accordance with an example embodiment.
Figure 22B:
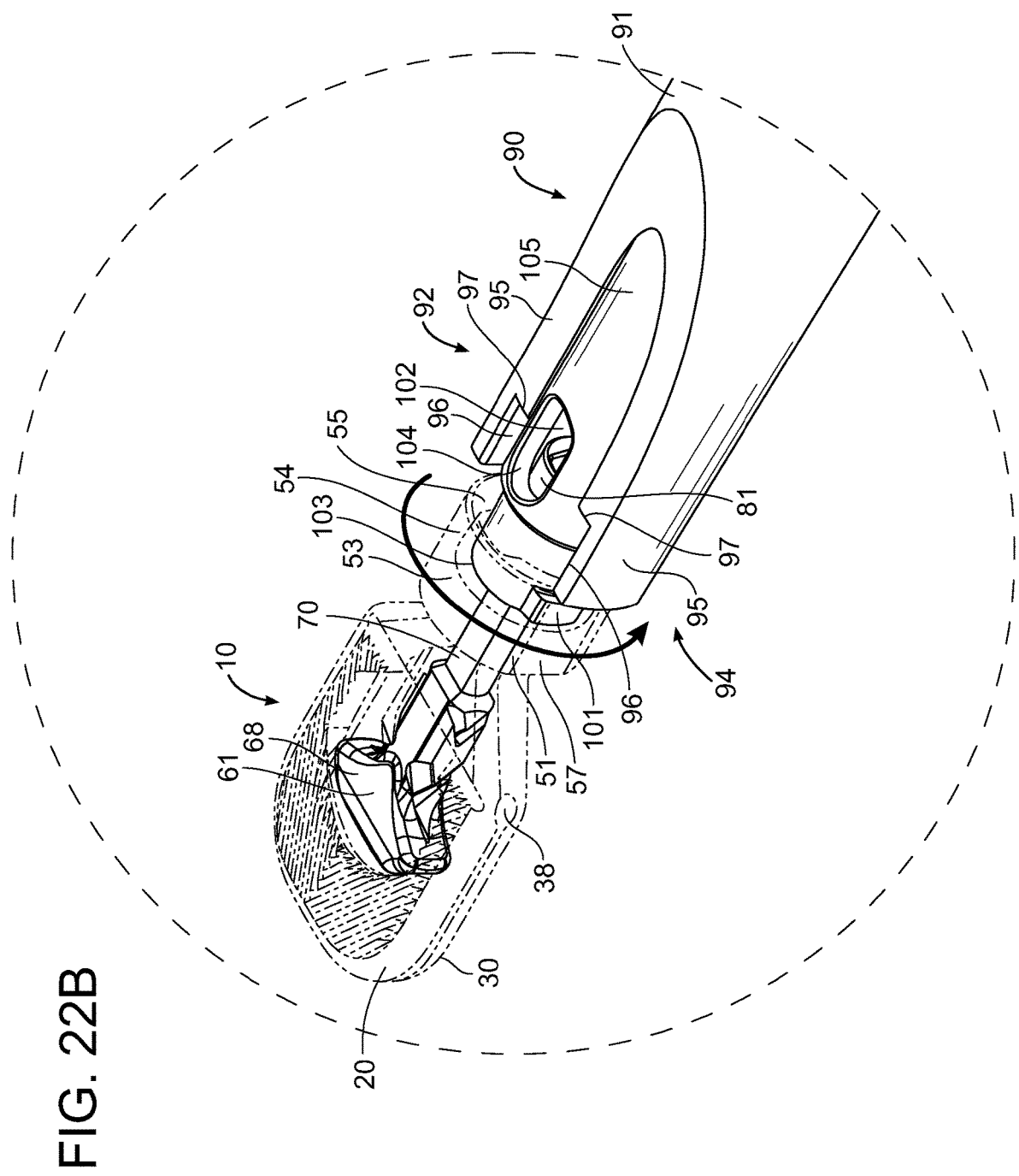
FIG. 22B is a partially transparent enlarged detail perspective view of a distally expanding facet joint implant and the distal end of a delivery device for use with the implant showing the delivery device and an outer part of the implant being brought into locked engagement in accordance with an example embodiment.
Figure 23A:
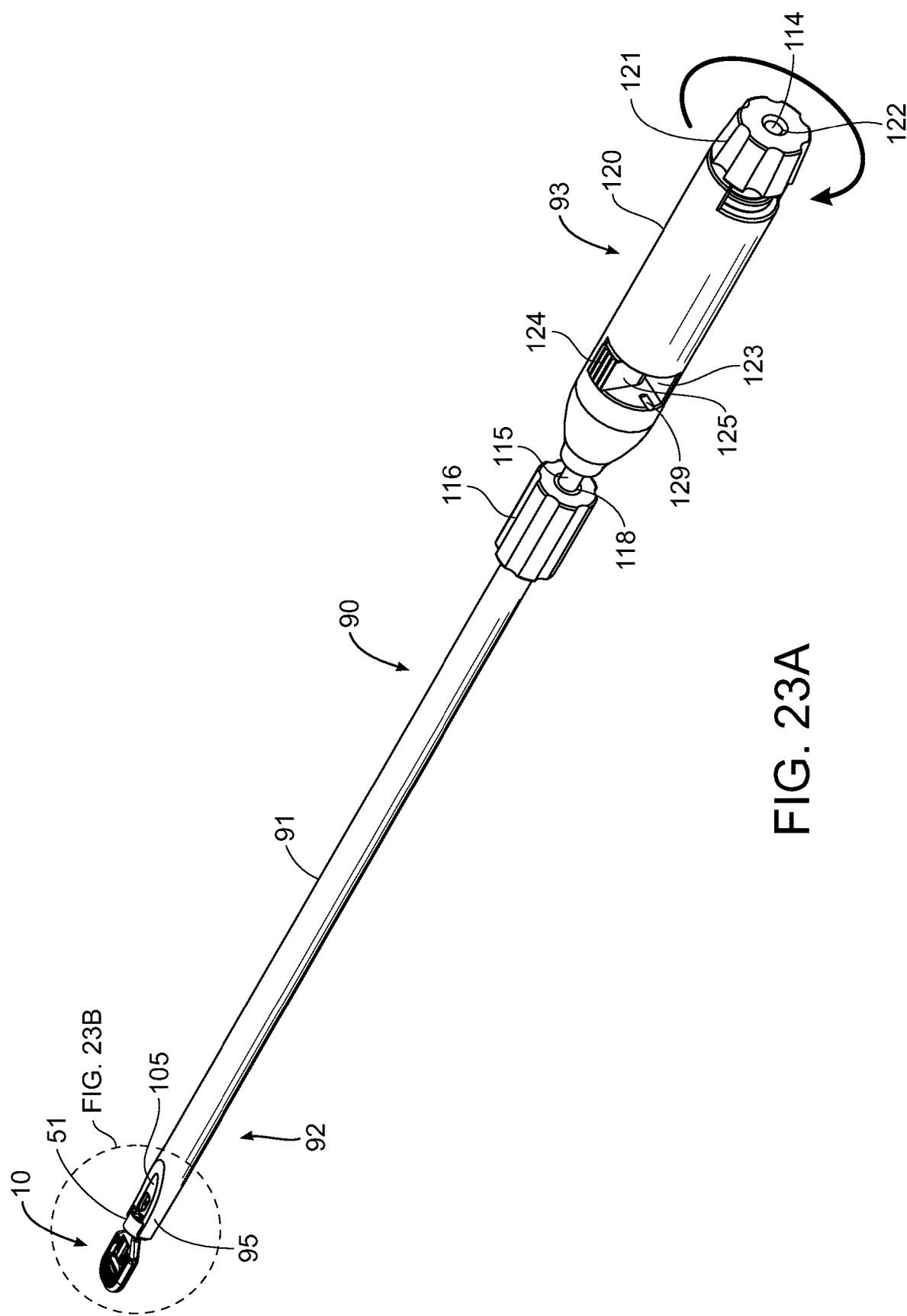
FIG. 23A is a perspective view of a distally expanding facet joint implant and a delivery device for use with the implant showing the delivery device and an inner part of the implant being brought into engagement in accordance with an example embodiment.
Figure 23B:
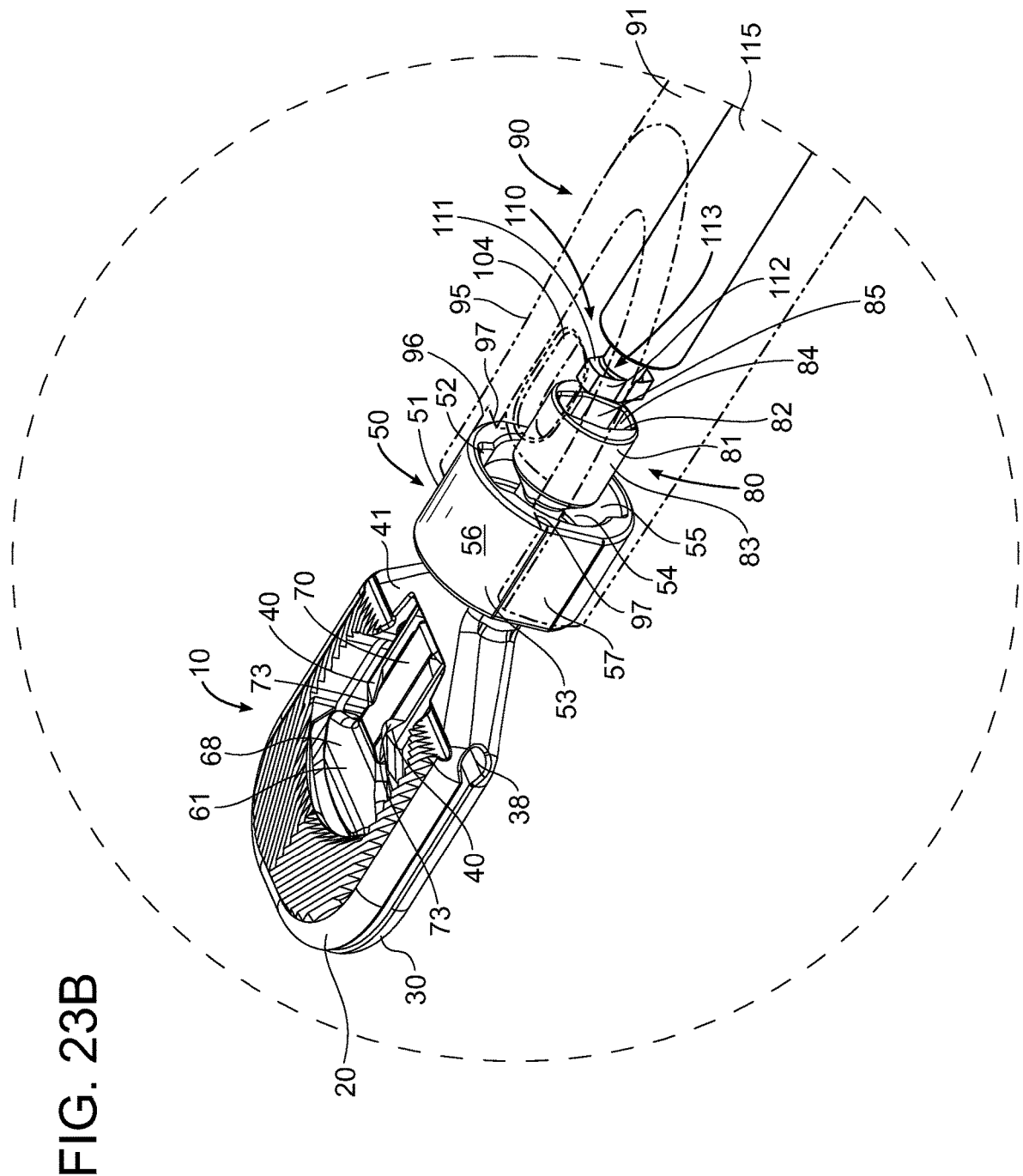
FIG. 23B is a partially transparent enlarged detail perspective view of a distally expanding facet joint implant and the distal end of a delivery device for use with the implant showing the delivery device and an inner part of the implant being brought into engagement in accordance with an example embodiment.
Figure 23C:
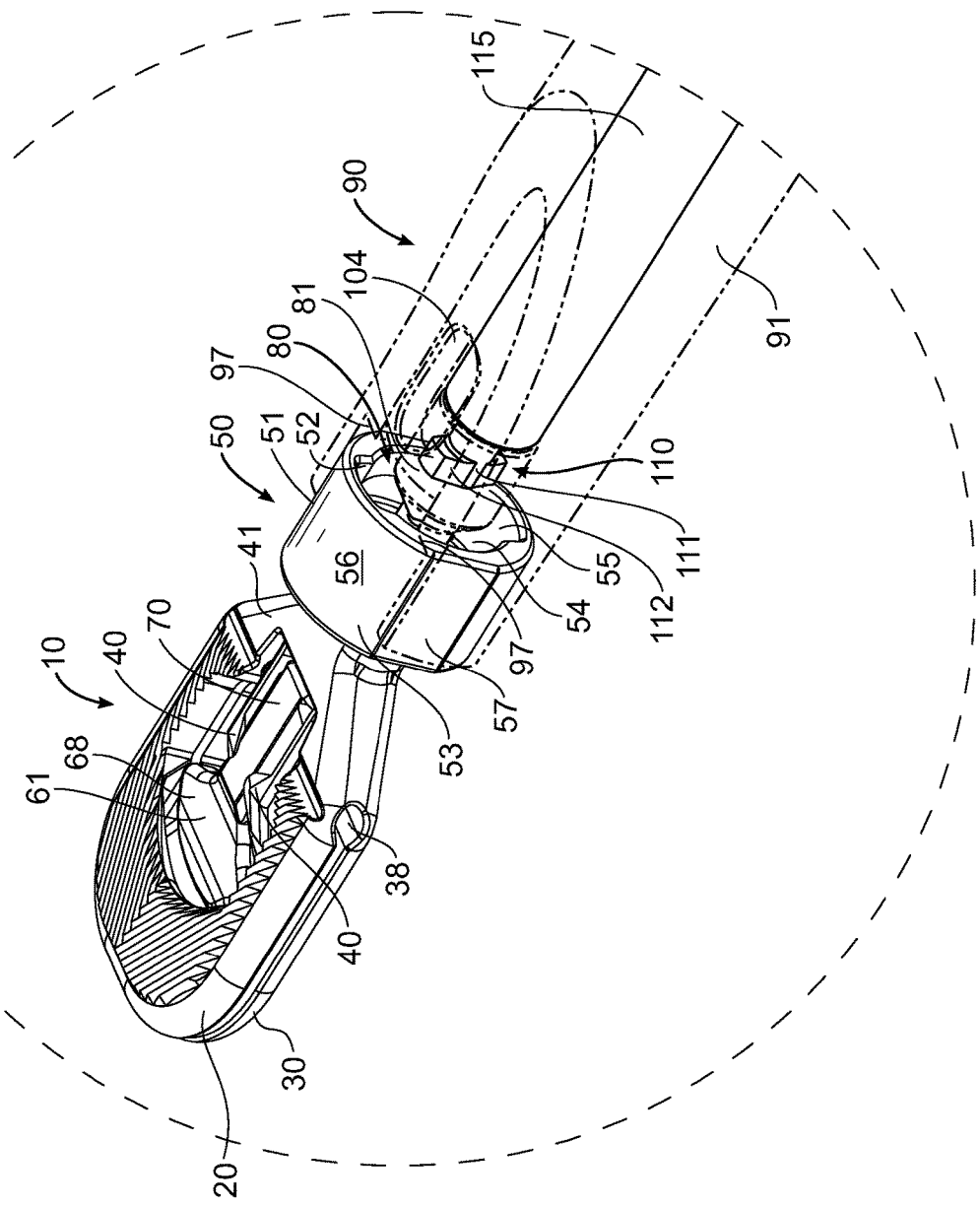
FIG. 23C is a partially transparent enlarged detail perspective view of a distally expanding facet joint implant and the distal end of a delivery device for use with the implant showing the delivery device and an inner part of the implant being brought into engagement in accordance with an example embodiment.
Figure 23D:
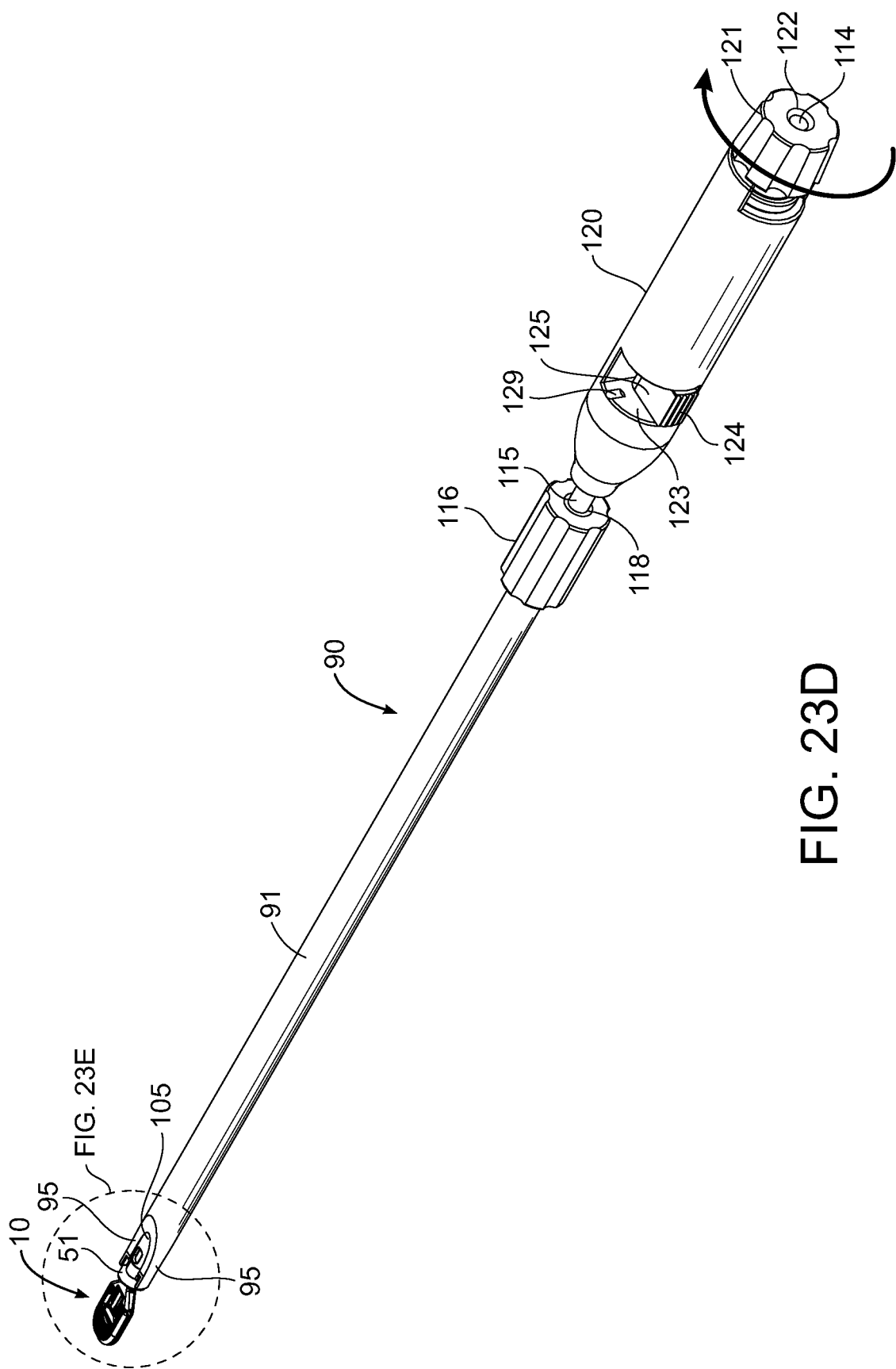
FIG. 23D is a perspective view of a distally expanding facet joint implant and a delivery device for use with the implant showing the delivery device and an inner part of the implant being brought into locked engagement in accordance with an example embodiment.
Figure 23E:
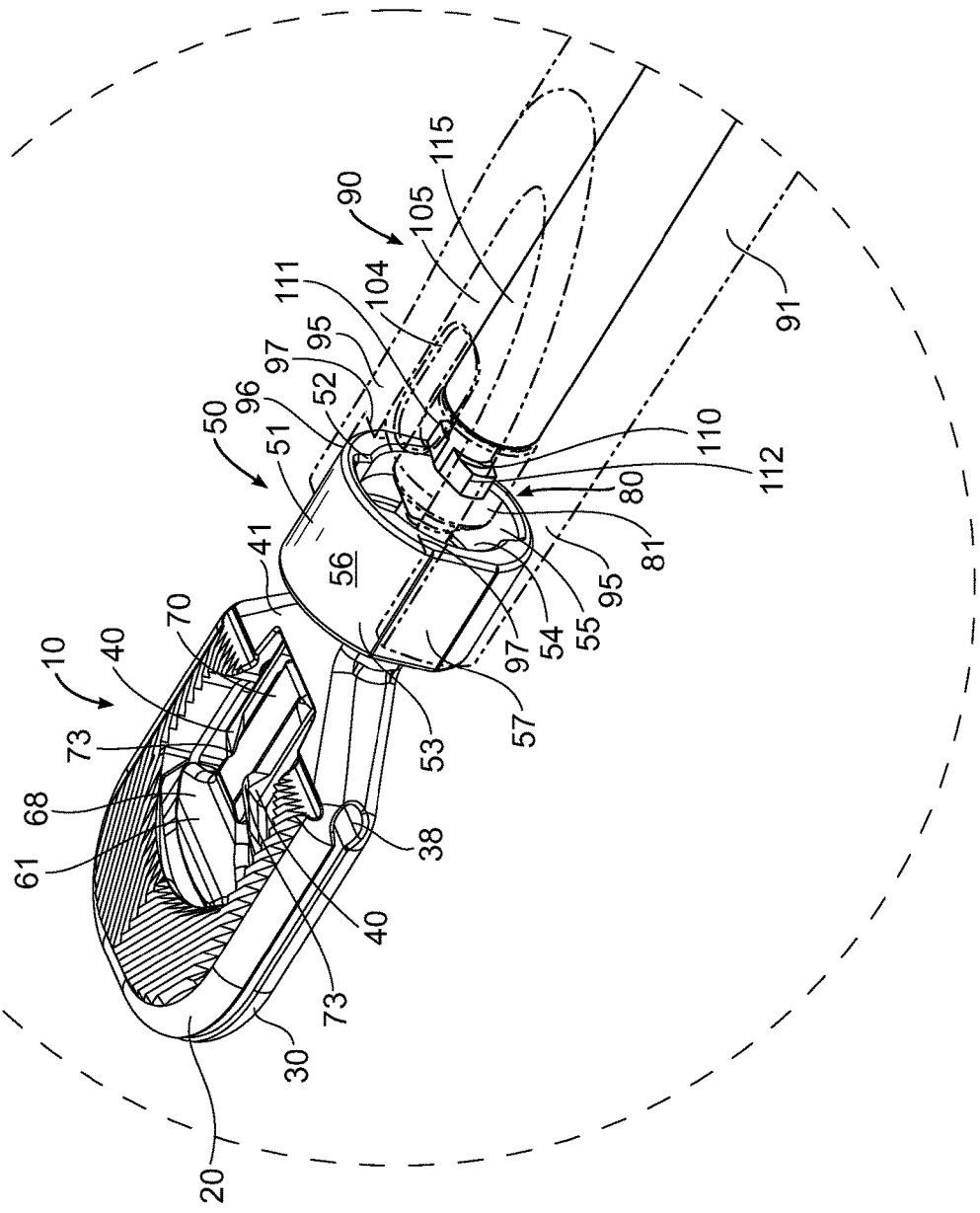
FIG. 23E is a partially transparent enlarged detail partial perspective view of a distally expanding facet joint implant and the distal end of a delivery device for use with the implant showing the delivery device and an inner part of the implant in locked engagement in accordance with an example embodiment.
Figure 25B:
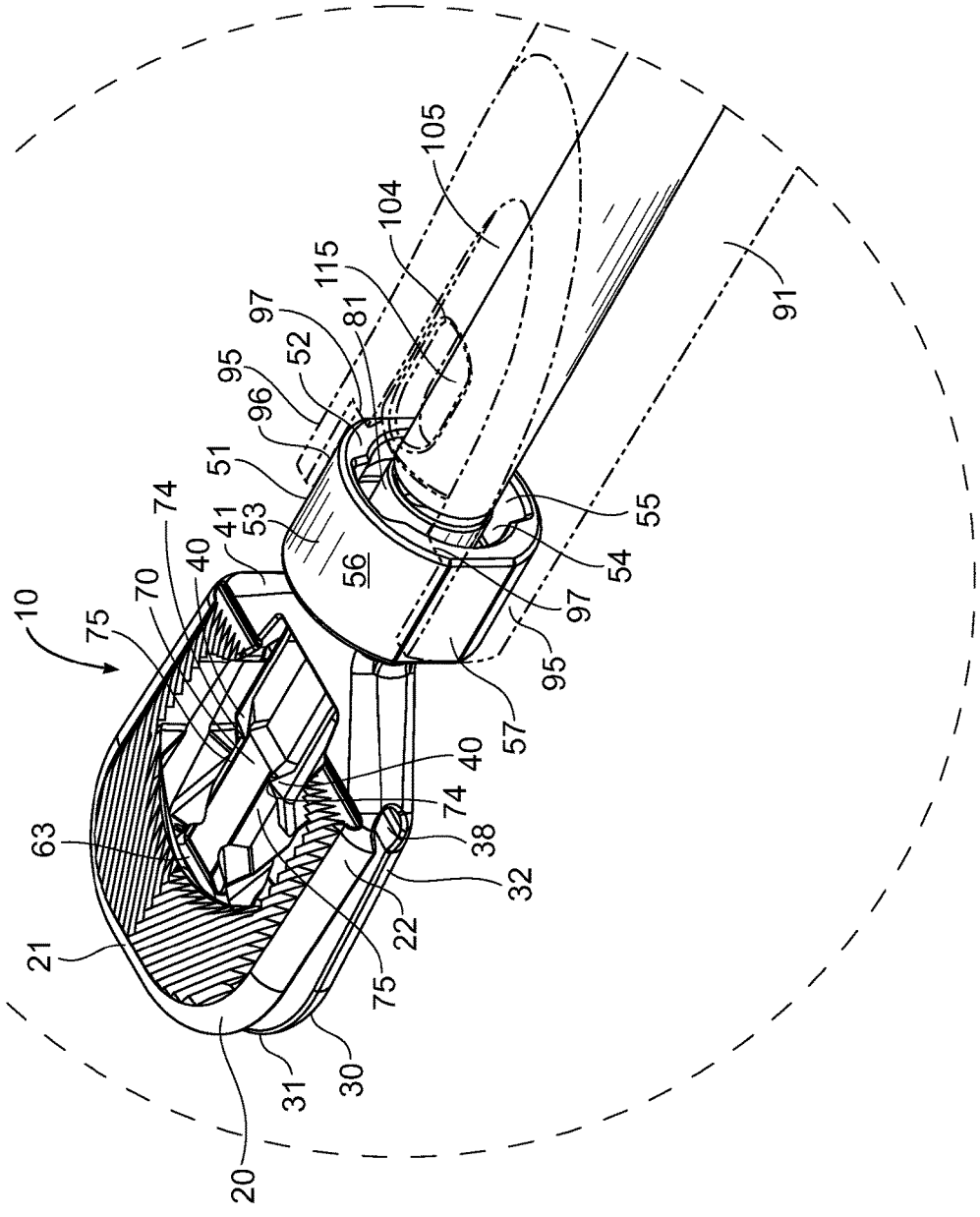
FIG. 25B is a partially transparent enlarged detail partial perspective view of a distally expanding facet joint implant and the distal end of a delivery device for use with the implant showing the delivery device in locked engagement with an inner part of the implant and the inner part being translated into a distally expanding outer part of the implant in accordance with an example embodiment.
Figure 27C:
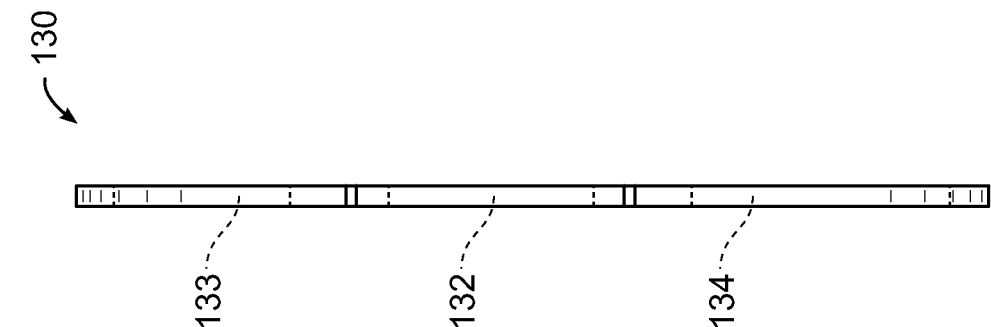
FIG. 27C is a side view of an inter-facet connection plate for use with a distally expanding facet joint implant in accordance with an example embodiment.
Figure 27B:
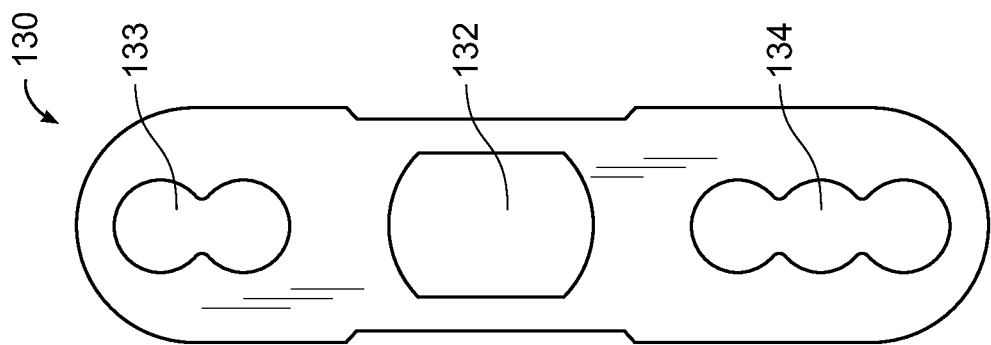
FIG. 27B is a top view of an inter-facet connection plate for use with a distally expanding facet joint implant in accordance with an example embodiment.
Figure 27A:
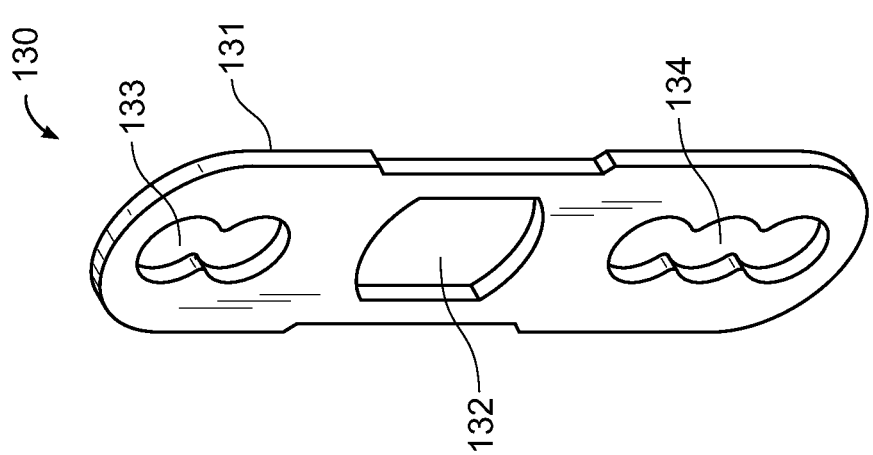
FIG. 27A is a perspective view of an inter-facet connection plate for use with a distally expanding facet joint implant in accordance with an example embodiment.

In preparation for implanting the facet joint implant 10, the facet joint implant 10 is connected to the distal end portion 92 of the delivery device 90 with the facet joint implant 10 in its closed state. With reference to FIGS. 21 through 22B among others, the delivery device 90 is manipulated to bring the corresponding first connector 100 of the delivery device 90 into engagement with the first connector 51 of the facet joint implant 10 and insert the corresponding first connector 100 into the first connector 51 of the facet joint implant 10. The control handle 120 of the delivery device 90 is rotated by approximately 90 degrees to bring the corresponding first connector 100 into locked engagement with the first connector 51. The outer tube 91 of the delivery device 90 is then manipulated to align the flat portions 96 of the holding arms 95 of the delivery device 90 with the flats 57 on the body 53 of the first connector 51 and the outer tube control knob 116 is rotated to advance the holding arms 95 toward the distal end portion 92 of the delivery device 90 and push the support surfaces 97 of the holding arms 95 into secure engagement with the first connector 51.

Next, with reference to FIGS. 23A through 23E among others, the corresponding second or inner connector 110 of the delivery device 90 is brought into locked engagement with the second or inner connector 81 of the facet joint implant 10. With the lock switch 124 of the delivery device 90 in the first (unlocked) position, the inner shaft control knob 121 of the delivery device 90 is rotated as to advance the corresponding second or inner connector 110 of the delivery device 90 distally into engagement with the second connector 81 of the facet joint implant 10 and to insert the t-shaped pin 112 of the second bayonet 111 into the open interior space 84 in the body 83 of the second bayonet connector 82 of the second or inner connector 81 of the facet joint implant 10. Proper alignment of the corresponding second or inner connector 110 and the second or inner connector 81 can be visually confirmed in the window 104 of the inner tube 105 of the delivery device 90.

With the corresponding second connector 110 in engagement with and inserted in the second connector 81, the lock switch 124 on the delivery device 90 is rotated approximately 90 degrees from the first (unlocked) position to the second (locked) position. This brings the corresponding second connector 110 into locked engagement with the second connector 81. The inner shaft control knob 121 can then be rotated in a first direction to cause the corresponding second connector 110 and the second connector 81 to advance distally, push the wedge 61 of the inner part 14 of the facet joint implant 10 forward distally relative to the first facet plate 20 and the second facet plate 30 of the outer part 12 of the facet joint implant 10, and thus cause the facet joint implant 10 to distally expand to its open position.

Optionally, an inter-facet connection plate 130 can be used with the facet joint implant 10 if desired. As illustrated in FIGS. 27A through 29E, a suitable inter-facet connection plate 130 may comprise a thin elongated plate 131 with a first opening 132, one or more second openings 133, and one or more third openings 134.

The first opening 132 is preferably located approximately centrally on the plate 131, but may be offset from a central location as desired. The first opening 132 is dimensioned and configured to permit at least the outer part 12 and the inner part 14 of the facet joint implant 10 to pass through the first opening 132 and into an adjacent facet joint 140 when the first opening 132 is aligned with a posterior opening 141 of the facet joint 140. The first opening 132 is also dimensioned and configured to block at least the first or outer connector 51 of the facet joint implant 10 from passing through the first opening 132 and entering the facet joint 140. This helps provide suitable positioning of the facet joint implant 10 in the facet joint 140 by helping to prevent the facet joint implant 10 from being over-inserted into the facet joint 140.

The one or more second openings 133 are located on the plate 131 relative to the first opening 132 so that when the first opening 132 is aligned with the posterior opening 141 of the facet joint 140, the one or more second openings 133 are positioned adjacent to the bony external surface 142 of the facet 143 superior to the facet joint 140. Similarly, the one or more third openings 134 are located on the plate 131 relative to the first opening 132 so that when the first opening 132 is aligned with the posterior opening 141 of the facet joint 140, the one or more third openings 134 are positioned adjacent the bony external surface 144 of the facet 145 inferior to the facet joint 140. Accordingly, the lengthwise dimension of the inter-facet connection plate 130 is preferably selected to be sufficient to span the posterior opening 141 of the facet joint 140 with the second and third openings 133, 134 located adjacent to the bony external surfaces 142, 144 of the superior and inferior facets 143, 145 when the first opening 132 is aligned with the posterior opening 141 of the facet joint 140.

The one or more second openings 133 and the one or more third openings 134 are dimensioned and configured to accept suitable screws 146 or other suitable fasteners so that the inter-facet connection plate 130 can be fixedly attached to and between the superior and inferior facets 143, 145 above and below the facet joint 140 with the facet joint implant 10 positioned in the facet joint 140 as illustrated in FIGS. 28A through 29E for example. To accommodate different vertebral physiologies, and for ease of adjustability during an implant procedure, the second and third openings 133, 134 can comprise a plurality of slightly overlapping openings. This permits the inter-facet connection plate 130 to be attached to the adjacent upper and lower facets 143, 145 at slightly different locations, and also provides a degree of adjustability to the entry angle and position of the facet joint implant 10 relative to the posterior opening 141 of the facet joint 140.

The inter-facet connection plate 130, if used, functions together with the distal expansion of the facet joint implant 10 to help stabilize the facet joint 140, help return or maintain the cervical spine in the locality of the facet joint 140 to proper alignment, and help in enhancing facet fusion by fixing the adjacent facets together. The inter-facet connection plate 130 may be constructed of any material that is suitable for long-term implantation in the body of a patient, and that is relatively strong and rigid, but also malleable enough to be shaped as necessary or desired to achieve the objectives noted above. One example of an inter-facet connection plate 130 shaped for use in connection with implantation of a facet joint implant in the facet joint between cervical vertebrae C4-C5 is illustrated in FIG. 28B. Another example is shown in FIGS. 29C-29D.

Once the facet joint implant 10 is connected at the distal end portion 92 of the delivery device 90 as described above, the delivery device is manipulated to introduce the facet joint implant 10 through the incision and to direct it through the dilated passage to the facet joint 140 in which it is to be implanted. As is known to persons skilled in the art, various means are available for visually or otherwise tracking the facet joint implant 10 as it is directed to the facet joint 140, including various means identified above.

If an inter-facet connection plate 130 is used, the outer part 12 of the facet joint implant 10 is passed through the first opening 132 in the inter-facet connection plate 130 before being introduced through the incision. In that case, the delivery device 90 is manipulated to introduce the facet joint implant 10 and the inter-facet connection plate 130 together through the incision and the dilated passage to the facet joint 140.

Figure 28A:
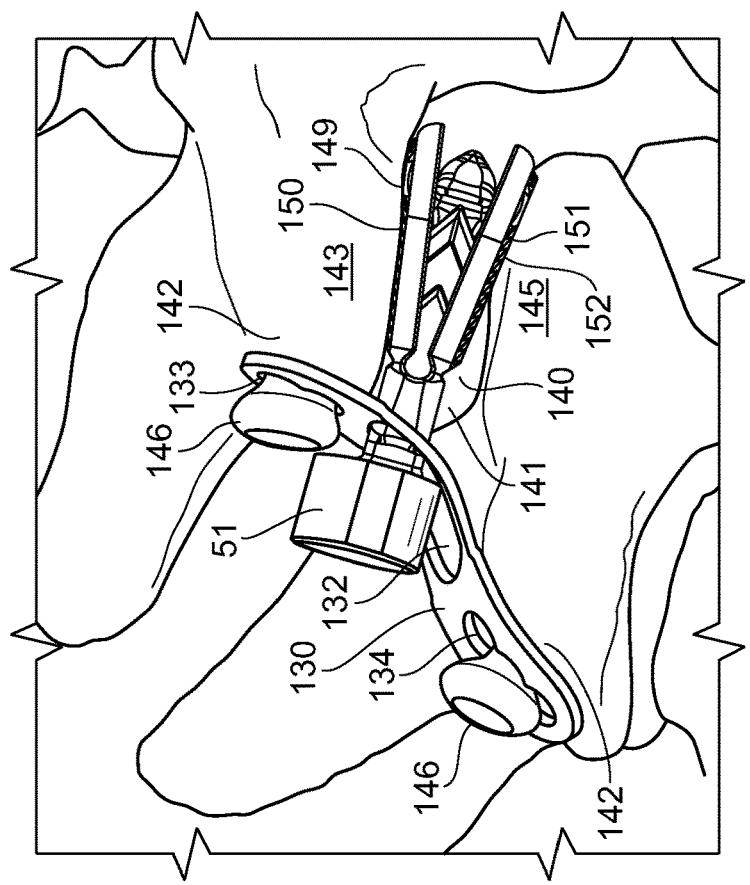
FIG. 28A is a perspective view of a distally expanding facet joint implant and an inter-facet connection plate in accordance with an example embodiment showing the implant in a closed state positioned in a facet joint between adjacent cervical facets.
Figure 28B:
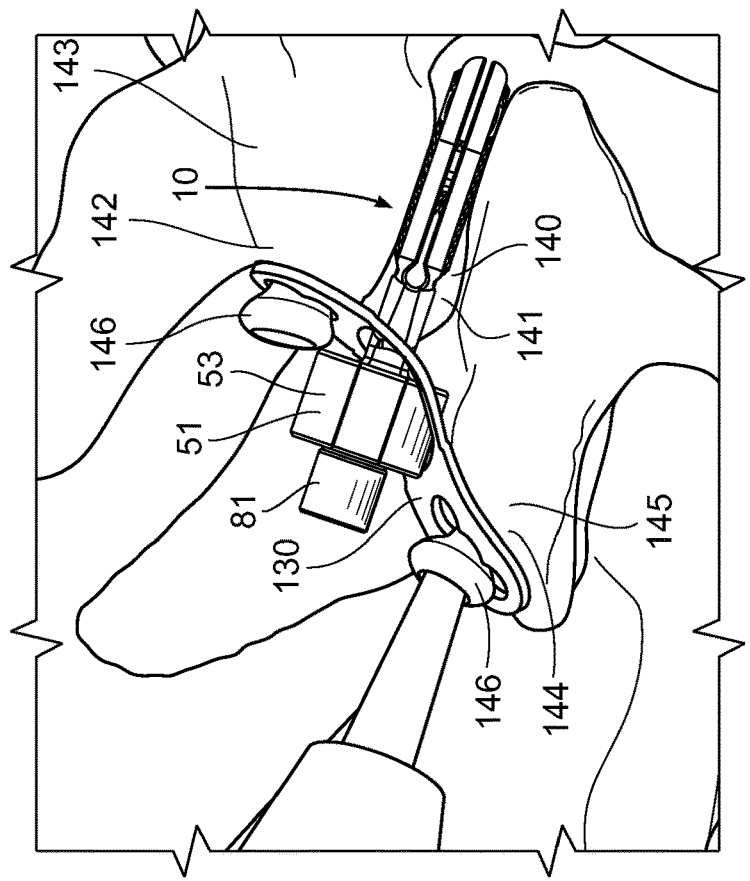
FIG. 28B is a perspective view of a distally expanding facet joint implant and an inter-facet connection plate in accordance with an example embodiment showing the implant in an open state positioned in a facet joint between adjacent cervical facets.
Figure 29A:
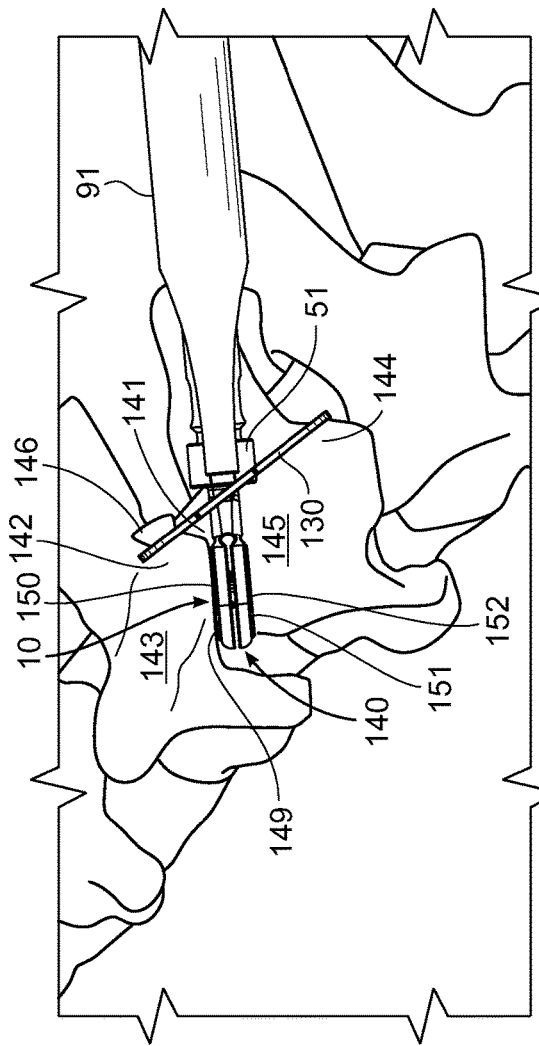
FIG. 29A is a partial perspective view of a distally expanding facet joint implant with an inter-facet connection plate and a delivery device in accordance with an example embodiment showing a step in a process of implanting the implant in a facet joint between adjacent cervical facets.
Figure 29B:
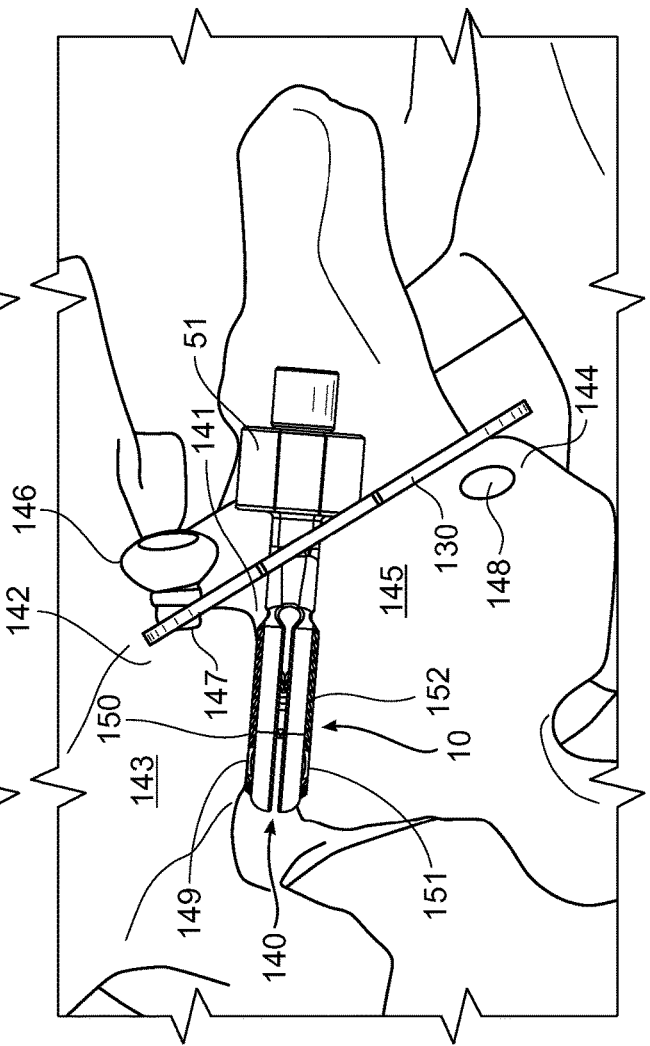
FIG. 29B is a partial perspective view of a distally expanding facet joint implant with an inter-facet connection plate in accordance with an example embodiment showing another step in a process of implanting the implant in a facet joint between adjacent cervical facets.
Figure 29D:
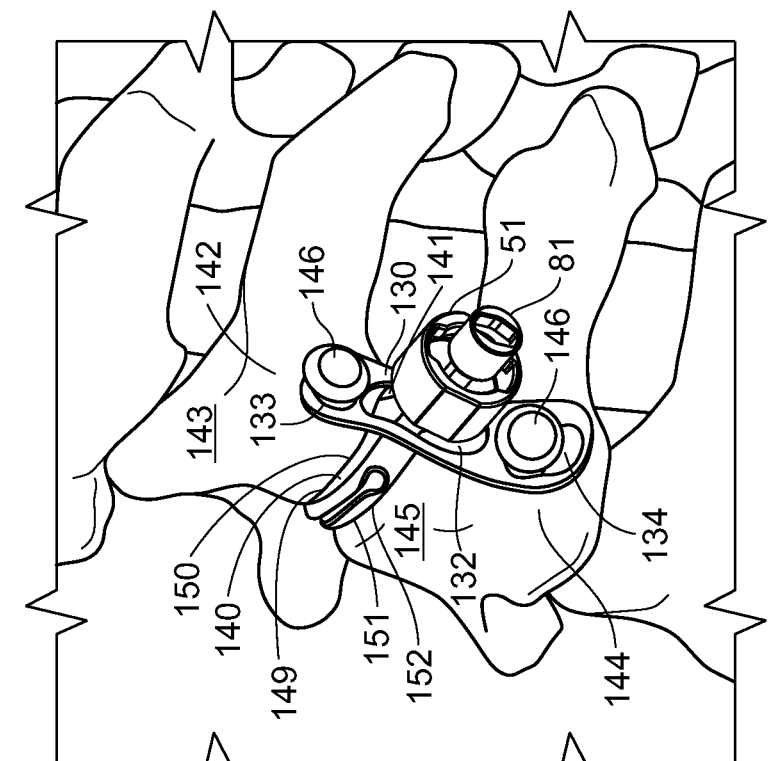
FIG. 29D is a perspective view of a distally expanding facet joint implant with an inter-facet connection plate in accordance with an example embodiment showing still another step in a process of implanting the implant in a facet joint between adjacent cervical facets.
Figure 29C:
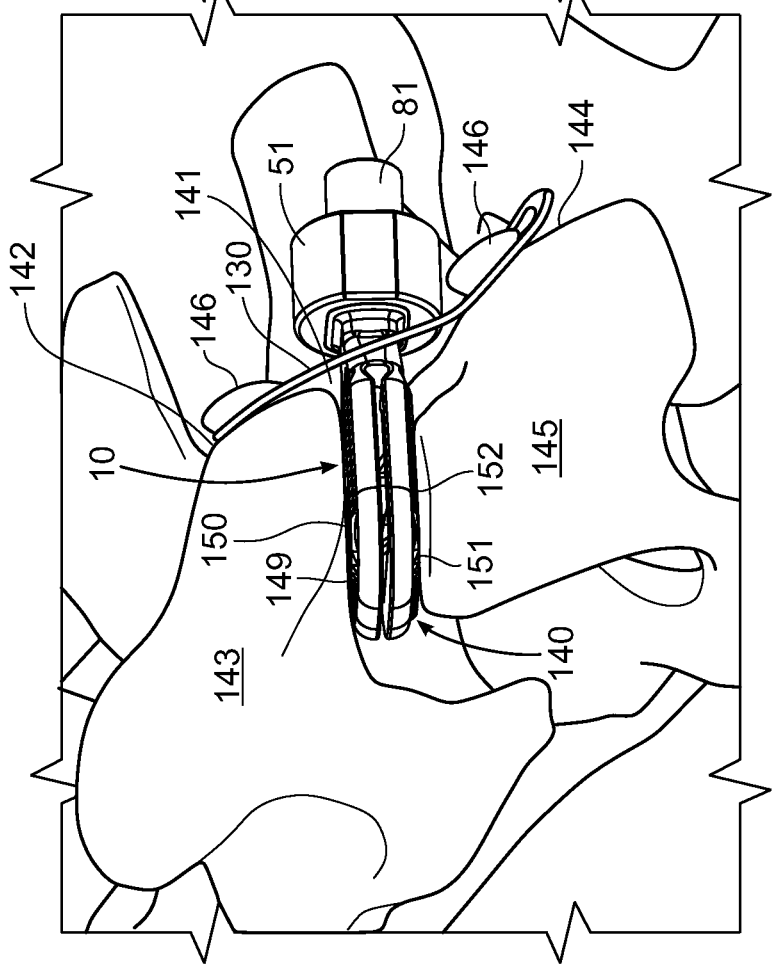
FIG. 29C is a side view of a distally expanding facet joint implant with an inter-facet connection plate in accordance with an example embodiment showing still another step in a process of implanting the implant in a facet joint between adjacent cervical facets.

At the facet joint 140, the delivery device 90 is manipulated to position and orient the facet joint implant 10 relative to the posterior opening 141 of the facet joint 140 as desired, and then to insert the facet joint implant 10 into the facet joint 140 as illustrated in FIGS. 28A and 29A. As described herein, preferably the first or outer first connector 51 of the facet joint implant 10 is dimensioned to be larger than the intended posterior spacing between the superior and inferior facets 143, 145, in other words larger than the intended posterior opening 141 of the facet joint 140. This feature helps provide suitable positioning of the facet joint implant 10 in the facet joint 140 by allowing the outer part 12 and the inner part 14 of the facet joint implant 10 to be positioned in the facet joint 140, but helps prevent the facet joint implant 10 from being over-inserted into the facet joint 140.

If an inter-facet connection plate 130 is used, the delivery device 90 can be manipulated to hold the facet joint implant 10 in the desired position while a hole 147 is drilled in the external surface 142 of the facet 143 superior to the facet joint 140 and a screw 146 is inserted to attach the inter-facet connection plate 130 to the superior facet 143 as shown in FIGS. 29A-29D. Similarly, a hole 148 is drilled in the facet 145 inferior to the facet joint 140 and a screw 146 is inserted to attach the inter-facet connection plate 130 to the inferior facet 145 as shown in FIGS. 29A-29D. As also shown in FIGS. 29C-29E, the inter-facet connection plate 130 can be shaped as necessary to help achieve the desired stabilization and alignment of the facet joint 140 and the adjacent vertebrae.

Methods for drilling holes and securing screws or other suitable fasteners in in bone, such as vertebrae, are well known to persons skilled in the art and need not be described here. Similarly, various drills, drill guides, etc. are well known for this purpose and need not be described here.

Figure 29E:
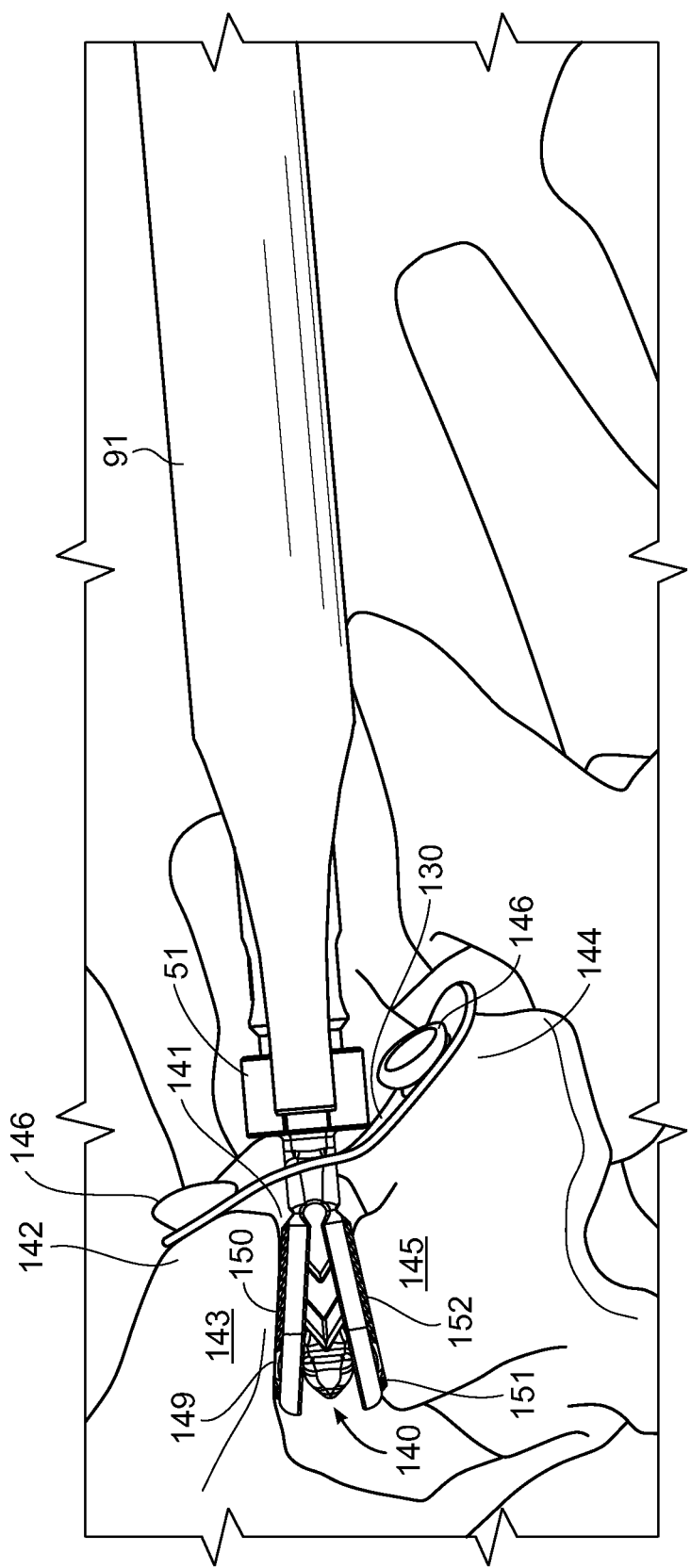
FIG. 29E is a partial perspective view of a distally expanding facet joint implant with an inter-facet connection plate and a delivery device in accordance with an example embodiment showing yet another step in a process of implanting the implant in a facet joint between adjacent cervical facets.

Once the facet joint implant 10 is properly positioned in the facet joint 140 and the inter-facet connection plate 130 is secured and shaped (if one was used), the delivery device 90 is manipulated in the manner described above and as illustrated in FIGS. 25A, 25B, and others to distally expand the facet joint implant 10 and distally distract the facet joint 140 as illustrated in FIGS. 28B and 29E. With the lock switch 124 of the delivery device 90 in the second (locked) position, the inner shaft control knob 121 of the delivery device 90 is rotated in the first direction to cause the facet joint implant 10 to distally expand from the closed state to the open state in the manner previously described herein. Preferably, the inner shaft control knob 121 is rotated until the facet joint implant 10 reaches its fully distally expanded open state as illustrated in FIGS. 28B and 29E, the first set of teeth 40 on the outer part 12 of the facet joint implant 10 engage the second set of indents 74 on the inner part 14 of the facet joint implant 10, and a physical feedback, for example a click, is sensed.

With the facet joint implant 10 properly positioned in the facet joint 140 in the fully distally expanded open state, the first exterior surface 24 of the first facet plate 20 will preferably be in substantial physical contact with an anterior portion 149 of the interior surface 150 of the superior facet 143 facing the facet joint 140, and the second exterior surface 34 of the second facet plate 30 will preferably be in substantial physical contact with an anterior portion 151 of the interior surface 152 of the inferior facet 145 facing the facet joint 140 as seen in FIGS. 28B and 29E. In this position, the first plurality of serrations 25 on the first exterior surface 24 of the first facet plate 20 and the second plurality of serrations 35 on the second exterior surface 34 of the second facet plate 30 help adhere the facet joint implant 10 to the bony surfaces of the superior and inferior facets 143, 145 facing the facet joint 140.

If the position of the facet joint implant 10 in the facet joint 10 is not as desired, however, the delivery device 90 may be manipulated to distally contract the facet joint implant 10 and to reposition the facet joint implant 10 in the facet joint 140. With the lock switch 124 on the delivery device 90 in the second (locked) position, the inner shaft control knob 121 on the delivery device is rotated in the direction opposite to the direction it was rotated to expand the facet joint implant 10. Preferably, the inner shaft control knob 121 is rotated in the opposite direction until the facet joint implant 10 has distally contracted sufficiently to be repositionable within the facet joint 140 or removed from the facet joint 140 if desired. The delivery device 90 can then be manipulated to reposition the facet joint implant 10 in the facet joint 140 as desired. Once the facet joint implant 10 is in the desired position, the delivery device can be manipulated to distally re-expand the facet joint implant 10 in the manner previously described.

Once the facet joint implant 10 is properly positioned in the facet joint 140 as desired and in its distally expanded open state, the delivery device 90 may be disconnected from the facet joint implant 10, and may be withdrawn posteriorly from the body of the patient through the dilated passageway and posterior incision. The delivery device 90 is disconnected from the facet joint implant 10 by simply reversing the order of the steps described above to connect the delivery device 90 to the facet joint implant 10.

If desired or necessary, additional steps can be performed before completing the procedure and closing the posterior incision. For example, bone paste may have been introduced in the facet joint 140 before the facet joint implant 10 was introduced to facilitate joint fusion in the future. The first opening 23 in the first facet plate 20 and the second opening 33 in the second facet plate 30 facilitate the dispersion of the bone paste or other medicinal or therapeutic substances in the facet joint 140, and also facilitate the growth of natural bone in, around, and through the facet joint implant 10. This in turn helps fuse the facets 143, 145 of the vertebrae adjacent to the facet joint 140 and further stabilize and strengthen the facet joint 140 and adjacent vertebrae.

A particularly beneficial effect of the distal expansion of the facet joint implant 10 as described is that the facet joint 140 is distracted distally, which results in widening of both the intervertebral disc space and intervertebral foramina and provides relief from the symptoms of cervical radiculopathy. Another possibly beneficial effect is that distraction of the facet joint 140 distally may help maintain the natural lordotic alignment of the cervical spine while avoiding the condition of kyphosis. This effect may be further enhanced by the use of inter-facet connection plate as described herein.

Unless otherwise defined, all technical and scientific terms used herein have the same meaning as commonly understood by one of ordinary skill in the art to which this invention belongs. Although methods and materials similar to or equivalent to those described herein can be used in the practice or testing of the distally expanding facet implant and delivery device, suitable methods and materials are described above. All publications, patent applications, patents, and other references mentioned herein are incorporated by reference in their entirety to the extent allowed by applicable law and regulations. The distally expanding facet implant and delivery device may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. A facet joint implant in combination with a delivery device, comprising:
   an outer part, wherein the outer part comprises a first facet plate, a second facet plate, and a hinge;
      wherein the first facet plate has a first distal end portion and a first proximal end portion;
      wherein the second facet plate has a second distal end portion and a second proximal end portion;
      wherein the hinge is located between the first proximal end portion of the first facet plate and the second proximal end portion of the second facet plate and has a first axis of rotation, wherein the hinge directly connects the first proximal end portion of the first facet plate and the second proximal end portion of the second facet plate in close proximity to and for rotation about the first axis of rotation, and wherein the hinge is configured to prevent the first proximal end portion of the first facet plate and the second proximal end portion of the second facet plate from moving out of the close proximity;
   an inner part, wherein the inner part comprises a wedge having a third distal end portion and a third proximal end portion, wherein the inner part comprises an interface adapted to be selectively brought into locked engagement with the delivery device;
   wherein when the inner part is in locked engagement with the delivery device the inner part is movable toward the first distal end portion of the first facet plate and the second distal end portion of the second facet plate by pushing the inner part with the delivery device in a linear motion and the third distal end portion of the wedge directly engages the first facet plate and the second facet plate so that the first distal end portion of the first facet plate and the second distal end portion of the second facet plate move apart and the first proximal end portion of the first facet plate and the second proximal end portion of the second facet plate rotate on the hinge about the first axis of rotation and in the close proximity in a first direction; and
      the inner part is movable toward the first proximal end portion of the first facet plate and the second proximal end portion of the second facet plate by pulling the inner part with the delivery device in a linear motion and the first distal end portion of the first facet plate and the second distal end portion of the second facet plate move toward each other, and the first proximal end portion of the first facet plate and the second proximal end portion of the second facet plate rotate on the hinge about the first axis of rotation and in the close proximity in a second direction.

2. The facet joint implant in combination with the delivery device of claim 1, wherein the first facet plate, the second facet plate, and the hinge comprise a first monolithic structure and the wedge comprises a second monolithic structure.

3. The facet joint implant in combination with the delivery device of claim 1, wherein:
the first facet plate has a first exterior surface with a first plurality of serrations or protrusions; and
the second facet plate has a second exterior surface with a second plurality of serrations or protrusions.

4. The facet joint implant in combination with the delivery device of claim 1, wherein:
the first facet plate has a first interior surface and the second facet plate has a second interior surface;
the wedge has a third exterior surface and a fourth exterior surface; and
when the inner part is moved toward the first distal end portion of the first facet plate and the second distal end portion of the second facet plate, the third exterior surface of the wedge directly engages the first interior surface of the first facet plate, and the fourth exterior surface of the wedge directly engages the second interior surface of the second facet plate.

5. The facet joint implant in combination with the delivery device of claim 1, wherein:
the first facet plate has a first interior surface, the second facet plate has a second interior surface, and the wedge has a third exterior surface and a fourth exterior surface;
the first interior surface of the first facet plate has a first sloped portion;
the second interior surface of the second facet plate has a second sloped portion;
the third exterior surface of the wedge has a third sloped portion adapted to directly engage and move relative to the first sloped portion of the first interior surface of the first facet plate; and
the fourth exterior surface of the wedge has a fourth sloped portion adapted to directly engage and move relative to the second sloped portion of the second interior surface of the second facet plate.

6. The facet joint implant in combination with the delivery device of claim 1, wherein the hinge comprises a living hinge.

7. The facet joint implant in combination with the delivery device of claim 1, wherein:
the facet joint implant has an open state wherein the first distal end portion of the first facet plate and the second distal end portion of the second facet plate are spaced apart by a predetermined distance, and a closed state wherein the first distal end portion of the first facet plate and the second distal end portion of the second facet plate are in close proximity;
the outer part comprises a first set of teeth in contact with the inner part;
the inner part comprises a first set of indents, wherein the first set of indents are located on the inner part so that when the facet joint implant is in the closed state, the first set of teeth is engaged with the first set of indents; and
the inner part comprises a second set of indents, wherein the second set of indents are located on the inner part so that when the facet joint implant is in the open state, the first set of teeth is engaged with the second set of indents.

8. The facet joint implant in combination with the delivery device of claim 1, wherein:
the outer part comprises a first delivery device interface; and
the interface of the inner part comprises a second delivery device interface.

9. The facet joint implant in combination with the delivery device of claim 8, wherein:
the first delivery device interface is connected to the first proximal end portion of the first facet plate and to the second proximal end portion of the second facet plate; and
the second delivery device interface is connected to the third proximal end portion of the wedge.

10. The facet joint implant in combination with the delivery device of claim 8, wherein:
the hinge has a third opening;
the inner part comprises an elongated connector; and
the elongated connector extends between the wedge and the second delivery device interface through the third opening.

11. The facet joint implant in combination with the delivery device of claim 8, wherein the first delivery device interface comprises a first connector configured to receive and to be brought into locked engagement with a corresponding first connector of the delivery device to hold the facet joint implant in a fixed position relative to the delivery device.

12. The facet joint implant in combination with the delivery device of claim 11, wherein the first connector comprises a first bayonet connector and the corresponding first connector of the delivery device comprises a first bayonet.

13. The facet joint implant in combination with the delivery device of claim 8, wherein the second delivery device interface comprises a second connector configured to receive a corresponding second connector of the delivery device.

14. The facet joint implant in combination with the delivery device of claim 13, wherein the second connector comprises a second bayonet connector and the corresponding second connector of the delivery device comprises a second bayonet.

15. The facet joint implant in combination with the delivery device of claim 8, wherein:
the first delivery device interface comprises a first connector;
the second delivery device interface comprises a second connector; and
the first connector extends around the second connector.

16. The facet joint implant in combination with the delivery device of claim 15, wherein the first connector and the second connector are arranged to be substantially concentric.

17. The facet joint implant in combination with the delivery device of claim 8, wherein:
the first delivery device interface of the facet joint implant comprises a first connector and the second delivery device interface of the facet joint implant comprises a second connector;
the delivery device has a distal end portion and a proximal end portion, and comprises:
a corresponding first connector at the distal end portion of the delivery device configured to selectively be brought into engagement with, be inserted in, and be brought into locked engagement with the first connector of the first delivery device interface; and a corresponding second connector at the distal end portion of the delivery device configured to selectively be brought into engagement with, be inserted in, and be brought into locked engagement with the second connector of the second delivery device interface.

18. The facet joint implant in combination with the delivery device of claim 17, wherein:

the first connector of the first delivery device interface comprises a first bayonet connector and the corresponding first connector of the delivery device comprises a first bayonet; and the second connector of the second delivery device interface comprises a second bayonet connector and the corresponding second connector of the delivery device comprises a second bayonet.

19. The facet joint implant in combination with the delivery device of claim 17, wherein:

when the corresponding first connector of the delivery device is brought into locked engagement with the first connector of the first delivery device interface, the facet joint implant is held in a fixed position relative to the delivery device.

20. The facet joint implant in combination with the delivery device of claim 19, wherein:

the delivery device comprises an outer tube that extends between the distal end portion and the proximal end portion, and wherein the outer tube comprises a first key and at least one support surface;

the corresponding first connector of the delivery device is at least partially contained within the outer tube and is movable relative to the outer tube to selectively be brought into engagement with the first connector of the first delivery device interface, be inserted in the first connector of the first delivery device interface, and be brought into locked engagement with the first connector of the first delivery device interface;

the corresponding second connector of the delivery device is at least partially contained within the outer tube and is movable relative to the outer tube and relative to the corresponding first connector to selectively be brought into engagement with the second connector of the second delivery device interface, be inserted into the second connector of the second delivery device interface, and be brought into locked engagement with the second connector of the second delivery device interface;

wherein the first key is configured to allow the corresponding first connector of the delivery device to be brought into engagement with and inserted in the first connector of the first delivery device interface only in proper alignment; and wherein the at least one support surface of the outer tube is configured to be engaged by the first connector of the first delivery device interface when the corresponding first connector of the delivery device is brought into locked engagement with the first connector of the first delivery device interface.

21. The facet joint implant in combination with the delivery device of claim 17, wherein:

the delivery device comprises an outer tube that extends between the distal end portion and the proximal end portion, an inner tube that is at least partially contained within the outer tube and that extends between the distal end portion and the proximal end portion, and an inner shaft that is at least partially contained within the inner tube and that extends between the distal end portion and the proximal end portion;

the inner tube is selectively movable toward the distal end portion, toward the proximal end portion, and rotationally relative to the outer tube;

the inner shaft is selectively movable toward the distal end portion, toward the proximal end portion, and rotationally relative to the inner tube;

the corresponding first connector is connected to the inner tube at the distal end portion of the delivery device; and the corresponding second connector is connected to the inner shaft at the distal end portion of the delivery device.

22. The facet joint implant in combination with the delivery device of claim 21, wherein the inner tube has a window opening, and wherein the corresponding second connector of the delivery device and the second connector of the second delivery device interface are at least partially visible through the window opening when the corresponding second connector of the delivery device is in engagement with the second connector of the second delivery device interface for observing the orientation of the corresponding second connector of the delivery device relative to the second connector of the second delivery device interface.

23. The facet joint implant in combination with the delivery device of claim 21, wherein the corresponding first connector and the corresponding second connector are arranged to be substantially concentric.

24. The facet joint implant in combination with the delivery device of claim 21, wherein the delivery device comprises:

an outer tube control knob located at the proximal end portion of the delivery device, wherein the outer tube control knob is coupled with the outer tube and is operable to selectively move the outer tube into secure engagement with the first connector of the first delivery device interface when the corresponding first connector of the delivery device is brought into engagement with the first connector of the first delivery device interface in proper alignment;

a control handle located at the proximal end portion of the delivery device, wherein the control handle is coupled with the corresponding first connector of the delivery device and is operable to selectively bring the corresponding first connector into locked engagement with the first connector of the first delivery device interface; and a control knob located at the proximal end portion of the delivery device, wherein the control knob is coupled with the corresponding second connector of the delivery device and is operable to selectively bring the corresponding second connector into engagement with the second connector of the second delivery device interface and to selectively insert the corresponding second connector of the delivery device in the second connector of the second delivery device interface.

25. The facet joint implant in combination with the delivery device of claim 24, wherein:

the delivery device comprises a lock switch and a lock; the lock switch and the lock are located at the proximal end portion of the delivery device;

the lock switch is coupled with the corresponding second connector of the delivery device and is operable to selectively rotate the corresponding second connector into and out of locked engagement with the second connector of the second delivery device interface; and the lock is coupled with the corresponding second connector of the delivery device and is operable in response to operation of the lock switch to maintain the corresponding second connector in locked engagement with the second connector of the second delivery device interface.

26. A facet joint implant in combination with a delivery device, wherein:

the facet joint implant comprises:

an outer part, wherein the outer part comprises a first facet plate, a second facet plate, a hinge, a first set of teeth, and a first bayonet connector configured to receive and to be brought into locked engagement with a corresponding first bayonet of the delivery device to hold the facet joint implant in a fixed position relative to the delivery device;

an inner part that is movable relative to the outer part, wherein the inner part comprises a wedge, a first set of indents, a second set of indents, and a second bayonet connector configured to receive and to be brought into locked engagement with a corresponding second bayonet of the delivery device to move the inner part relative to the outer part by pushing the delivery device;

wherein the first facet plate has a first distal end portion and a first proximal end portion;

wherein the second facet plate has a second distal end portion and a second proximal end portion;

wherein the hinge connects the first proximal end portion of the first facet plate and the second proximal end portion of the second facet plate;

wherein the wedge has a third distal end portion and a third proximal end portion;

wherein the first bayonet connector extends around the second bayonet connector;

wherein when the inner part is moved toward the first distal end portion of the first facet plate and the second distal end portion of the second facet plate, the third distal end portion of the wedge engages the first facet plate and the second facet plate so that the first distal end portion of the first facet plate and the second distal end portion of the second facet plate move apart and the first proximal end portion of the first facet plate and the second proximal end portion of the second facet plate rotate on the hinge in a first direction;

wherein when the inner part is moved toward the first proximal end portion of the first facet plate and the second proximal end portion of the second facet plate, the first distal end portion of the first facet plate and the second distal end portion of the second facet plate move toward each other and the first proximal end portion of the first facet plate and the second proximal end portion of the second facet plate rotate on the hinge in a second direction;

wherein the facet joint implant is in an open state when the first distal end portion of the first facet plate and the second distal end portion of the second facet plate are spaced apart by a predetermined distance, and a closed state when the first distal end portion of the first facet plate and the second distal end portion of the second facet plate are in close proximity; and wherein when the facet joint implant is in the closed state, the first set of teeth is engaged with the first set of indents, and when the facet joint implant is in the open state, the first set of teeth is engaged with the second set of indents;

the delivery device comprises:

a distal end portion and a proximal end portion;

an outer tube that extends between the distal end portion and the proximal end portion, an inner tube that is at least partially contained within the outer tube and that extends between the distal end portion and the proximal end portion, and an inner shaft that is at least partially contained within the inner tube and that extends between the distal end portion and the proximal end portion;

wherein the inner tube is selectively movable toward the distal end portion, toward the proximal end portion, and rotationally relative to the outer tube;

wherein the inner shaft is selectively movable toward the distal end portion, toward the proximal end portion, and rotationally relative to the inner tube;

wherein the first bayonet is connected to the inner tube at the distal end portion of the delivery device; and wherein the second bayonet is connected to the inner shaft at the distal end portion of the delivery device;

wherein the inner tube includes a window opening, and wherein the second bayonet and the second bayonet connector are at least partially visible through the window opening when the second bayonet is in engagement with the second bayonet connector;

an outer tube control knob at the proximal end portion, wherein the outer tube control knob is coupled with the outer tube and is operable to selectively move the outer tube into secure engagement with the first bayonet connector when the first bayonet is brought into engagement with the first bayonet connector in proper alignment;

a control handle at the proximal end portion, wherein the control handle is coupled with the first bayonet and is operable to selectively bring the first bayonet into locked engagement with the first bayonet connector; and a control knob at the proximal end portion, wherein the control knob is coupled with the second bayonet and is operable to selectively bring the second bayonet into engagement with the second bayonet connector and to selectively insert the corresponding second bayonet in the second bayonet connector; and a lock switch and a lock at the proximal end portion, wherein the lock switch is coupled with the corresponding second bayonet and is operable to selectively rotate the corresponding second bayonet into and out of locked engagement with the second bayonet connector, and wherein the lock is coupled with the second bayonet and is operable in response to operation of the lock switch to maintain the second bayonet in locked engagement with the second bayonet connector.

* * * * *